US011053297B2

(12) United States Patent
Hedrick et al.

(10) Patent No.: US 11,053,297 B2
(45) Date of Patent: Jul. 6, 2021

(54) MONOCYTE MODULATION AND CONTROL OF TUMOR METASTASIS

(71) Applicant: La Jolla Institute for Allergy and Immunology, La Jolla, CA (US)

(72) Inventors: Catherine C. Hedrick, La Jolla, CA (US); Richard Hanna, San Diego, CA (US)

(73) Assignee: La Jolla Institute for Allergy and Immunology, La Jolla, CA (US)

( * ) Notice: Subject to any disclaimer, the term of this patent is extended or adjusted under 35 U.S.C. 154(b) by 0 days.

(21) Appl. No.: 15/772,388

(22) PCT Filed: Oct. 27, 2016

(86) PCT No.: PCT/US2016/059182
§ 371 (c)(1),
(2) Date: Apr. 30, 2018

(87) PCT Pub. No.: WO2017/075253
PCT Pub. Date: May 4, 2017

(65) Prior Publication Data
US 2018/0312568 A1  Nov. 1, 2018

Related U.S. Application Data

(60) Provisional application No. 62/248,869, filed on Oct. 30, 2015.

(51) Int. Cl.
| *A61K 35/15* | (2015.01) |
| *A61P 35/04* | (2006.01) |
| *A61K 35/00* | (2006.01) |
| *C07K 14/705* | (2006.01) |
| *A61K 38/17* | (2006.01) |
| *A61K 31/704* | (2006.01) |
| *A61K 38/19* | (2006.01) |
| *A61K 47/68* | (2017.01) |
| *A61P 35/00* | (2006.01) |
| *A61K 39/395* | (2006.01) |
| *A61K 45/06* | (2006.01) |
| *A61K 47/02* | (2006.01) |
| *C07K 16/24* | (2006.01) |
| *C07K 16/28* | (2006.01) |
| *A61K 39/00* | (2006.01) |
| *A61N 5/10* | (2006.01) |

(52) U.S. Cl.
CPC ...... *C07K 14/70567* (2013.01); *A61K 31/704* (2013.01); *A61K 35/15* (2013.01); *A61K 38/1783* (2013.01); *A61K 38/195* (2013.01); *A61K 39/3955* (2013.01); *A61K 45/06* (2013.01); *A61K 47/02* (2013.01); *A61K 47/6849* (2017.08); *A61P 35/00* (2018.01); *A61P 35/04* (2018.01); *C07K 16/24* (2013.01); *C07K 16/2857* (2013.01); *A61K 2039/545* (2013.01); *A61N 5/10* (2013.01); *C07K 2317/20* (2013.01); *C07K 2317/21* (2013.01); *C07K 2317/24* (2013.01); *C07K 2319/00* (2013.01); *C07K 2319/30* (2013.01)

(58) Field of Classification Search
CPC .............. C07K 14/70567; A61K 35/15; A61K 47/6849; A61P 35/04; A61P 35/00
USPC ...................................................... 424/134.1
See application file for complete search history.

(56) References Cited

U.S. PATENT DOCUMENTS

2012/0141538 A1* 6/2012 Gorochov .................. 424/278.1
2013/0108602 A1  5/2013 Hedrick et al.

OTHER PUBLICATIONS

Hanna et al., Patrolling monocytes control tumor metastasis to the lung, Science, 2015, pp. 1-9 [online]. <URL: https://www.researchgate.net/profile/Catherine_Hedrick/publication/283209262_Patrolling_monocytes_control_tumor_metastasis_to_the_lung/links/562fd1aa08aea4eec6dddb1d.pdf>.

* cited by examiner

Primary Examiner — Yan Xiao
(74) Attorney, Agent, or Firm — Pillsbury Winthrop Shaw Pittmann LLP

(57) ABSTRACT

Disclosed herein are methods of increasing numbers of monocytes to a tumor or cancer metastasis site in a subject. Non-limiting embodiments include administering or using a Nur77 polypeptide or subsequence thereof; a Nur77 agonist; a CX3CR1 agonist; CD14+ CD16$^+$ monocytes and/or CD14dimCD16$^+$ (CD115$^+$CD11b$^+$ GR1$^-$ (Ly6C-)) monocytes; CD14$^+$ CD16$^+$ monocytes and/or CD14dimCD16$^+$ (CD115$^+$CD11b$^+$GR1$^-$ (Ly6C-)) monocytes contacted with a Nur77 agonist or contacted with a CX3CR1 agonist. Also disclosed herein are methods of increasing, stimulating, activating or promoting monocyte migration to or mobilization against a tumor or cancer metastasis in a subject. Non-limiting embodiments include administering a Nur77 polypeptide or subsequence thereof; a Nur77 agonist; a CX3CR1 agonist; CD14+ CD16+ monocytes and/or CD14dimCD16$^+$ (CD115$^+$CD11b$^+$GR1$^-$ (Ly6C-)) monocytes; or CD14$^+$ CD16$^+$ monocytes and/or CD14dimCD16$^+$ (CD115$^+$CD11b$^+$GR1$^-$ (Ly6C-)) monocytes contacted with a Nur77 agonist or contacted with a CX3CR1 agonist.

12 Claims, 21 Drawing Sheets
Specification includes a Sequence Listing.

A

B

Day 7 After B16F10 Tumor

FIG. 21 Mechanism for regulation of tumor metastasis by patrolling monocytes 1. Induction of vascular damage and inflammation by tumor extravasation
2. Expression of CX3CL1 by endothelial cells
3. Recruitment of patrolling monocytes to site of vascular damage and tumor
4. Uptake of tumor material by patrolling monocytes
5. Release of CCL3/4/5 from patrolling monocytes
6. Recruitment and activation of NK cells
7. NK cells kill tumor

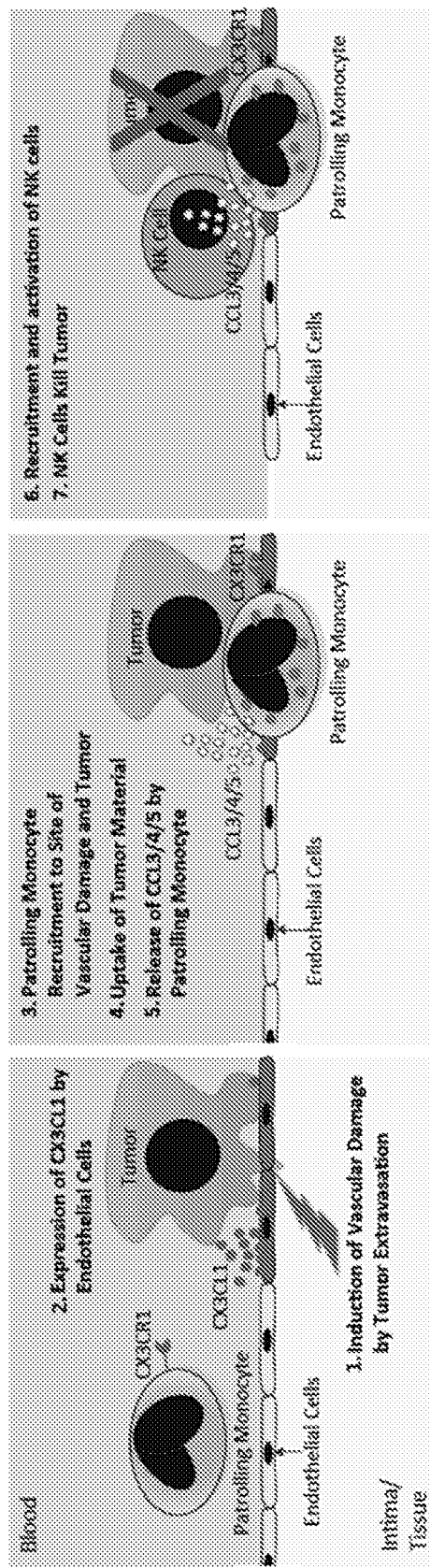

MONOCYTE MODULATION AND CONTROL OF TUMOR METASTASIS

RELATED PATENT APPLICATIONS

This application is the National Phase of International Application No. PCT/US2016/059182, filed Oct. 27, 2016 which designated the U.S. and that International Application was published under PCT Article 21(2) in English, and claims priority to U.S. Provisional Patent Application No. 62/248,869 filed Oct. 30, 2015. The entire contents of the foregoing applications are incorporated herein by reference, including all text, tables and drawings.

GOVERNMENT SUPPORT

This invention was made with support under NIH RO1 HL118765, American Heart Association Scientist Development Grant 12SDG12070005. The government has certain rights in this invention.

SEQUENCE LISTING

The instant application contains a Sequence Listing which has been submitted electronically in ASCII format and is hereby incorporated by reference in its entirety. Said ASCII copy, created on May 14, 2020, is named LIAI0458737_ST25.txt and is 10.845 bytes in size.

INTRODUCTION

The need to develop new strategies for treatment of tumors and metastases is clearly evident when the five year survival rate of cancer patients is considered: Only 10-40% for patients with lung, colorectal, breast and prostate cancer survive if diagnosed with distant metastatic disease.

Nur77, along with Nurr1 and NOR-1, constitute the NR4A subfamily of orphan nuclear receptors in the steroid/thyroid receptor family. Nur77 has been implicated in the differentiation, proliferation, apoptosis, and survival of many different cell types. Nur77 was originally identified as a growth factor inducible gene, and is often over-expressed in a variety of cancer cells including lung, prostate, breast and colon cancers (Lim et al., *Oncogene* 1:263 (1987); Hazel et al., *Proc Natl Acad Sci USA* 85:8444 (1988); Milbrandt, *Neuron* 1:183 (1988); Chang et al., *J Steroid Biochem* 34:391 (1989); Uemura and Chang, *Endocrinology* 139:2329 (1998); Wu et al., *Oncogene* 21:3925 (2002); Jeong et al., *Ann N Y Acad Sci* 1010:171 (2003); Holla et al., *J Biol Chem* 281:2676 (2005); Maddika et al., *J Cell Sci* 118:4485 (2005)).

A number of growth factors and mitogens can potently and rapidly induce the expression of Nur77, suggesting an anti-apoptotic role of Nur77 in mediating growth of cancer cells. Contrarily, Nur77 has been implicated in programmed cell death of T and B lymphocytes (Rajpal et al., *EMBO J.* 22:6526 (2003); Lee et al., *Proc Natl Acad Sci USA* 99:11878 (2002)). Nur77 is rapidly induced by T-cell receptor signals, and dominant negative Nur77 inhibits clonal deletion of developing T cells, indicating a role for Nur77 and its family members in thymocyte apoptosis (Zhou et al., *J Exp Med* 183:1879 (1996); Woronicz et al., *Nature* 367:277 (2004); Cho et al., *J Immunol* 170:10 (2003)). Nur77 mRNA is also rapidly (<1 hour) induced in macrophages in response to a variety of inflammatory stimuli, including LPS, cytokines, and oxidized lipids (Pei et al., *J Biol Chem* 280:29256 (2005)).

Structural and functional studies of Nur77 and other NR4A family members suggest that these nuclear receptor family members do not need to bind small-molecule ligands to be activated (Baker et al., *Cell* 113:731(2003); Wang et al., *Nature* 423:555 (2003)), and instead are regulated by posttranslational modifications such as phosphorylation (Fahrner et al., *Mol Cell Biol* 10:6454 (1990)). Acting as a transcription factor, Nur77 can directly bind specific DNA response elements alone or can heterodimerize with the retinoid X receptor (RXR) (Wilson et al., *Science* 252:1296 (1991); Wallen-Mackenzie et al., *Genes Dev* 17:3036 (2003)). Nur77 binding sites have been identified on the IKBα promoter and have been suggested as a means for regulating NFKB inflammatory signaling (You et al., *Circ Res* 104:742 (2009)). In response to apoptotic stimuli, Nur77 may dimerize with RXR, and translocate from the nucleus to the cytoplasm where it can target mitochondria to induce cytochrome c release and apoptosis (Li et al., *Science* 289:1159 (2000)). Consistent with its role as an apoptotic mediator in T and B cells, Nur77 can target mitochondrial function through its interaction with Bcl-2, converting Bcl-2 from an anti-apoptotic to a pro-apoptotic molecule (Lin et al., *Cell* 116:527 (2004); Thompson and Winoto, *J Exp Med* 205:1029 (2008)).

Little is known about the exact functions of Nur77 in monocyte biology. Nur77 is expressed in human atherosclerotic lesion macrophages, and reduces human macrophage lipid loading and inflammatory responses in atherosclerotic plaques (Bonta et al., *Arterioscler Thromb Vasc Biol* 26:2288 (2006); Arkenbout et al., *Circulation* 106:1530 (2002)). Nur77 expression also inhibits macrophage accumulation and vascular remodeling in mice (Bonta et al., *Cardiovasc Res* 87:561 (2010)). Conneely and colleagues generated a NOR-1−/− Nur77−/− double knockout mouse and observed development of acute myeloid leukemia in the mice, with abnormal expansion of myeloid progenitor cells (Mullican et al., *Nat Med* 13:730 (2007)). However, mice deficient in either Nur77 or NOR-1 have relatively subtle abnormalities and lack overt defects in general physiology, consistent with the idea that NR4A family members have some functional redundancy (Lee et al., *Science* 269:532 (1995)). Interestingly, Nurr1 (also known as NR4A2), a related NR4A family member, has recently demonstrated a regulatory role in maintaining hematopoietic stem cell quiescence (Sirin et al., *Nat Cell Biol* 12:1213 (2010)).

In mice and humans, at least two distinct blood monocyte subsets exist which can be identified as being CD11b+ and CD115+. In mice, Ly6C+, CCR2+, CX3CR1$^{lo}$, CD62L+ monocytes are inflammatory and migrate to injured or infected sites, and Ly6C−, CCR2−, CX3CR1$^{high}$ and CD62L− monocytes patrol the resting vasculature and participate in the resolution of inflammation (Randolph et al., *Curr Opin Lipidol* 19:462 (2008); Tacke et al., *J Exp Med* 203:583 (2006)). Mouse Ly6C+ monocytes correspond to CD14+ CD16− inflammatory monocytes in humans, and Ly6C− mouse monocytes serve as counterparts to CD14$^{dim}$ CD16+ and CD14+CD16+ human patrolling monocytes (Cros et al., *Immunity* 33:375 (2010); Randolph, *J Thromb Haemost* 7:28 (2009)). Ly6C+ monocytes are selectively recruited to inflamed or infected tissues and lymph nodes (Randolph et al., *Curr Opin Lipidol* 19:462 (2008); Geissmann et al. *Immunity* 19:71 (2003); Palframan et al., *J Exp Med* 194:1361 (2001)). Ly6C− monocytes are believed to be monocytes that don't readily migrate in response to inflammation; rather they tend to patrol the resting vasculature, populate normal or inflamed sites, and participate in the resolution of inflammation (Nahrendorf et al., *J Exp Med*

204:3037 (2007); Auffray et al., *Science* 317:666 (2007); Geissmann et al. *Immunity* 19:71 (2003); Tacke et al., *J Clin Invest* 117:185 (2007)).

Monocyte subsets arise from a common macrophage dendritic precursor (MDP) in the bone marrow (Auffray et al., *J Exp Med* 206:595 (2009)). However, the details of the differentiation steps and intermediaries between MDPs and monocytes subsets are unclear. Adoptive transfer studies demonstrate that Ly6C+ monocytes can down-regulate Ly6C expression, and move between blood and bone marrow (Arnold et al., *J Exp Med* 204:1057 (2007); Varol et al., *J Exp Med* 204:171 (2007); Yrlid et al., *J Immunol* 176:4155 (2006)), but whether these are functionally equivalent to patrolling Ly6C- monocytes has been questioned (Geissmann et al., *Science* 327:656 (2010)). In contrast, other groups have demonstrated that distinct populations of monocytes are recruited to inflammation/injury sites (Auffray et al., *Science* 317:666 (2007); Nahrendorf et al., *J Exp Med* 204:3037 (2007); Landsman et al., *J Immunol* 178:2000 (2007)). A number of transcription factors including PU.1, JunB, CEBPα/β, and IRF8 have important roles in myeloid lineage differentiation, but the specific factors that drive differentiation of Ly6C- monocytes are unknown (Auffray et al., *Annu Rev Immuno* 127:669 (2009)).

SUMMARY

Little is known about the physiological function of non-classical patrolling monocytes. As disclosed herein, patrolling monocytes are enriched in the microvasculature of lung and are important in controlling, limiting or preventing initial tumor metastasis to lung. Patrolling monocytes were found to establish early interactions with tumor cells and specifically remove tumor material from the lung vasculature, in a CX3CR1-dependent manner. NR4A1 (Nur77)-deficient mice, which have a unique loss of Ly6C$^-$ patrolling monocytes in the hematopoietic compartment, have significantly increased metastasis of syngeneic tumor cells to the lung. Transfer of Nur77$^-$ proficient patrolling monocytes into Nur77$^-$ deficient hosts in a gain-of-function manner significantly reduces tumor invasion in lung. These studies indicate an important contribution of Nur77-dependent patrolling monocytes in cancer immune surveillance, which will provide cancer immunotherapy.

In accordance with the invention, there are provided methods and uses for directing monocytes to a tumor or cancer metastasis site, or increasing or promote numbers of monocytes in a tumor or cancer metastasis site. In one embodiment, a method or use includes administering a (a) Nur77 polypeptide or subsequence thereof; (b) Nur77 agonist; (c) CX3CR1 agonist; (d) CD14$^+$ CD16$^+$ monocytes and/or CD14$^{dim}$CD16$^+$ (CD115+CD11b$^+$GR1$^-$ (Ly6C–)) monocytes: or (e) CD14$^+$ CD16$^+$ monocytes and/or CD14$^{dim}$CD16$^+$ (CD115+CD11b$^+$GR1$^-$ (Ly6C–)) monocytes contacted with a Nur77 agonist or contacted with a CX3CR1 agonist to a subject in an amount to direct monocytes to a tumor or cancer metastasis site, or to increase or promote numbers of monocytes in the tumor or cancer metastasis site.

In accordance with the invention, there are also provided methods and uses for increasing, stimulating, activating or promoting monocyte migration to or mobilization against a tumor or cancer metastasis. In one embodiment, a method or use includes administering a (a) Nur77 polypeptide or subsequence thereof; (b) Nur77 agonist; (c) CX3CR1 agonist; (d) CD14$^+$ CD16$^+$ monocytes and/or CD14$^{dim}$CD16$^+$ (CD115+CD11b$^+$GR1$^-$ (Ly6C–)) monocytes; or (e) CD14$^+$ CD16$^+$ monocytes and/or CD14$^{dim}$CD16$^+$ (CD115$^+$CD11b$^+$GR1$^-$ (Ly6C–)) monocytes contacted with a Nur77 agonist or contacted with a CX3CR1 agonist, to a subject in an amount that increases, stimulates, activates or promotes monocyte migration to or mobilization against the tumor or cancer metastasis.

In accordance with the invention, there are further provided methods and uses for controlling, limiting, or decreasing metastasis of a tumor or cancer. In one embodiment, a method or use includes administering a (a) Nur77 polypeptide or subsequence thereof; (b) Nur77 agonist; (c) CX3CR1 agonist; (d) CD14$^+$ CD16$^+$ monocytes and/or CD14$^{dim}$CD16$^+$ (CD115$^+$CD11b$^+$GR1$^-$ (Ly6C–)) monocytes; or (e) CD14$^+$ CD16$^+$ monocytes and/or CD14$^{dim}$CD16$^+$ (CD115$^+$CD11b$^+$GR1$^-$ (Ly6C–)) monocytes contacted with a Nur77 agonist or contacted with a CX3CR1 agonist, to a subject in an amount to control, limit, or decrease metastasis of the tumor or cancer in the subject.

In accordance with the invention, there are moreover provided methods and uses for controlling, limiting, or decreasing metastasis of a tumor or cancer from an original site to one or more other sites in a subject. In one embodiment, a method or use includes administering a (a) Nur77 polypeptide or subsequence thereof; (b) Nur77 agonist; (c) CX3CR1 agonist; (d) CD14$^+$ CD16$^+$ monocytes and/or CD14$^{dim}$CD16$^+$ (CD115$^+$CD11b$^+$GR1$^-$ (Ly6C–)) monocytes; or (e) CD14$^+$ CD16$^+$ monocytes and/or CD14$^{dim}$CD16$^+$ (CD115$^+$CD11b$^+$GR1$^-$ (Ly6C–)) monocytes contacted with a Nur77 agonist or contacted with a CX3CR1 agonist, to a subject in an amount to control, limit, or decrease metastasis of the tumor or cancer in the subject.

In accordance with the invention, there are additionally provided methods and uses for controlling, limiting, or decreasing metastasis of a tumor or cancer in a subject. In one embodiment, a method or use includes administering a (a) CX3CR1 agonist; (b) CD14$^+$ CD16$^+$ monocytes and/or CD14$^{dim}$CD16$^+$ (CD115$^+$CD11b$^+$GR1$^-$ (Ly6C–)) monocytes; or (c) CD14$^+$ CD16$^+$ monocytes and/or CD14$^{dim}$CD16$^+$ (CD115$^+$CD11b$^+$GR1$^-$ (Ly6C–)) monocytes contacted with a CX3CR1 agonist, to a subject in an amount to control, limit, or decrease metastasis of the tumor or cancer in the subject.

In accordance with the invention, there are still further provided methods and uses for controlling, limiting, or decreasing metastasis of a tumor or cancer from an original site to one or more other sites in a subject. In one embodiment, a method or use includes administering a (a) Nur77 polypeptide or subsequence thereof; (b) Nur77 agonist; (c) CX3CR1 agonist; (d) CD14$^+$ CD16$^+$ monocytes and/or CD14$^{dim}$CD16$^+$ (CD115$^+$CD11b$^+$GR1$^-$ (Ly6C–)) monocytes; or (e) CD14$^+$ CD16$^+$ monocytes and/or CD14$^{dim}$CD16$^+$ (CD115$^+$CD11b$^+$GR1$^-$ (Ly6C–)) monocytes contacted with a Nur77 agonist or contacted with a CX3CR1 agonist, to a subject in an amount to control, limit, or decrease metastasis of the tumor or cancer in the subject.

Additional embodiments are described in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

GFP$^{high}$ monocytes from the lung of Nur77-GFP mice. Nur77-GFP$^{high}$CD11b$^+$ cells were gated from all Live CD45$^+$CD11c$^{low}$ cells and then examined for CD115 and Ly6C expression. (B) Quantification of Nur77-GFP$^{high}$ patrolling monocytes per μl of blood volume in lung (Untreated), 4 hrs or 24 hrs after IV LLC-RFP transfer (n=5). (C) Quantification of Nur77-GFP$^{high}$ monocyte movement in lung before (Untreated), 4 hrs or 24 hrs after LLC-RFP tumor injection. Monocyte tracks transposed to a common origin from a representative 20 min movie (not shown), and quantification of median speed of monocytes (right, n=3, *=p<0.001). (D) Gating of Nur77-GFP$^{high}$ CD11b$^+$ cells from all LiveCD45$^+$CD11c$^{low}$ cells 24 hrs after IV LLC-RFP transfer. (E) Confocal imaging of Nur77-GFP$^{high}$ monocytes (Green) interacting with LLC-RFP cells (Red) in the lung 7 days after IV LLC-RFP transfer. Immune cells in the vasculature were labeled with IV injected anti-CD45 antibody (Blue). (F) Quantification of free (>100 μm from tumor site) and tumor-associated (<50 μm from tumor site) Nur77-GFP$^{high}$ monocytes in the lung at various time points after tumor injection (n=5).

Figure 2:
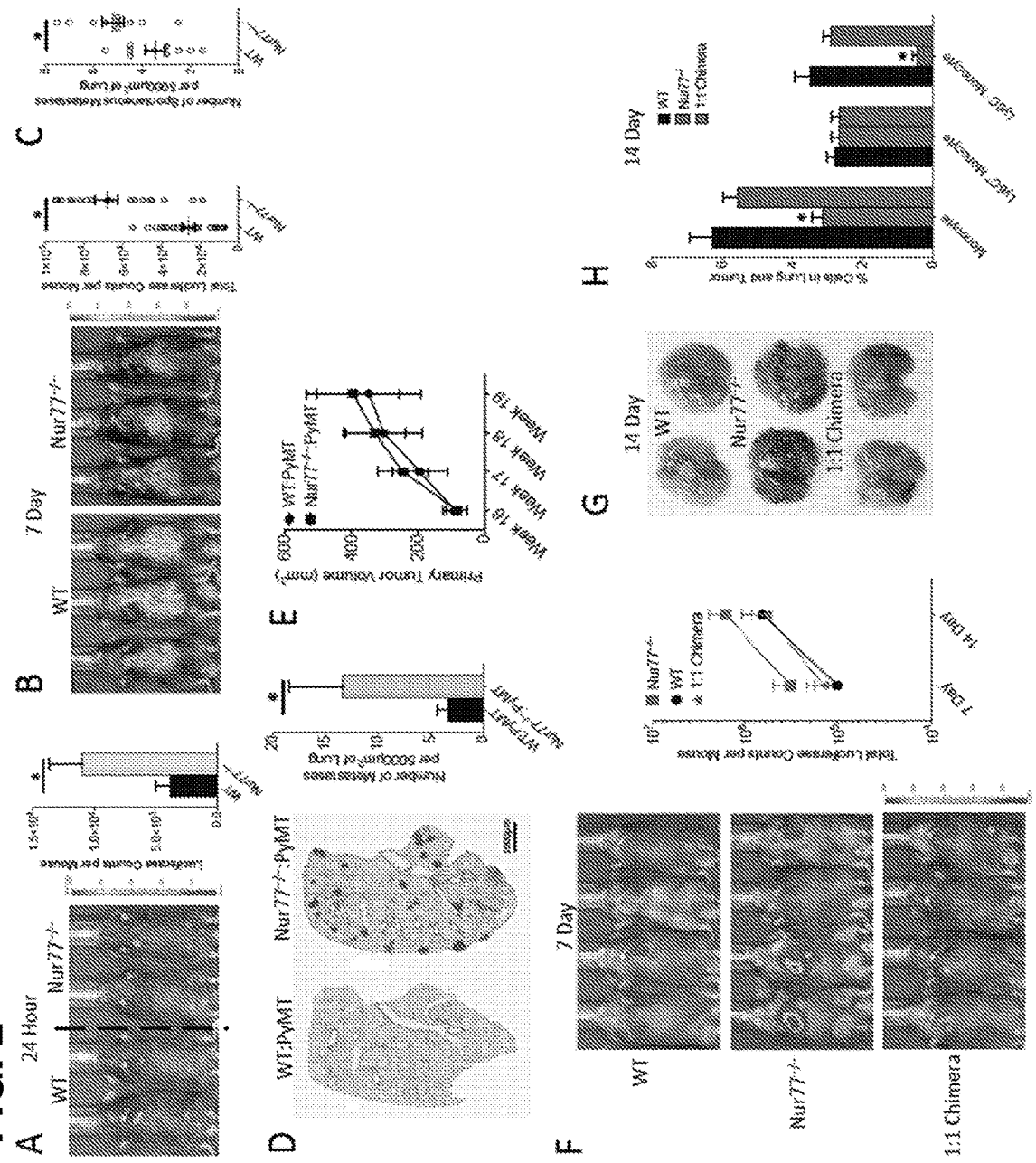

FIG. 2. Increased lung metastasis of tumors in Nur77$^{-/-}$ mice. (A) In vivo luciferase detection in wild-type control (WT) and Nur77$^{-/-}$ mice 24 hrs after IV injection of 5×10$^5$ B16F10 melanoma cells expressing luciferase (Left) and quantification (Right) (*=p<0.01, n=5). (B) In vivo luciferase detection (Left), and quantification (Right), in WT and Nur77$^{-/-}$ mice 7 days after IV injection with 3×10$^5$ B16F10-luciferase cells (*=p<0.001, n=18). (C) Number of spontaneous tumor metastases per 5000 μm$^2$ of lung surface 28 days after SubQ injection of 1×10$^5$ B16F10-YFP cells (*=p<0.01, n=10). (D-E) Lung tumor metastasis in MMTV-PyMT mice reconstituted with WT (WT:PyMT) or Nur77$^{-/-}$ (Nur77$^{-/-}$:PyMT) bone marrow. (D) Representative MMTVPyMT mouse lung histology stained with hematoxylin and eosin (Left), and quantification of number of spontaneous lung metastases per 5000 μm$^2$ of lung surface (Right). (E) Quantification of primary breast tumor growth in MMTV-PyMT mice. (*=p<0.05 n=12 for WT and n=15 for Nur77$^{-/-}$). (F-H) CD45.2 Nur77$^{-/-}$, CD45.1 WT, or 1:1 (CD45.2 Nur77$^{-/-}$:CD45.1 WT) bone marrow was transplanted into irradiated recipient CD45.2 WT mice, and 6 weeks following reconstitution 3×10$^5$ B16F10-luciferase cells were injected IV into the recipients and analyzed (n=5, *=p<0.01). (F) In vivo images of luciferase expression 7 days after tumor transfer (Left), and quantification of luciferase counts at 7 and 14 days after tumor transfer (Right). (G) Representative lung pictures and (H) percentage of CD45+ monocytes associated with lung tumor environment 14 days after IV transfer.

Figure 3:
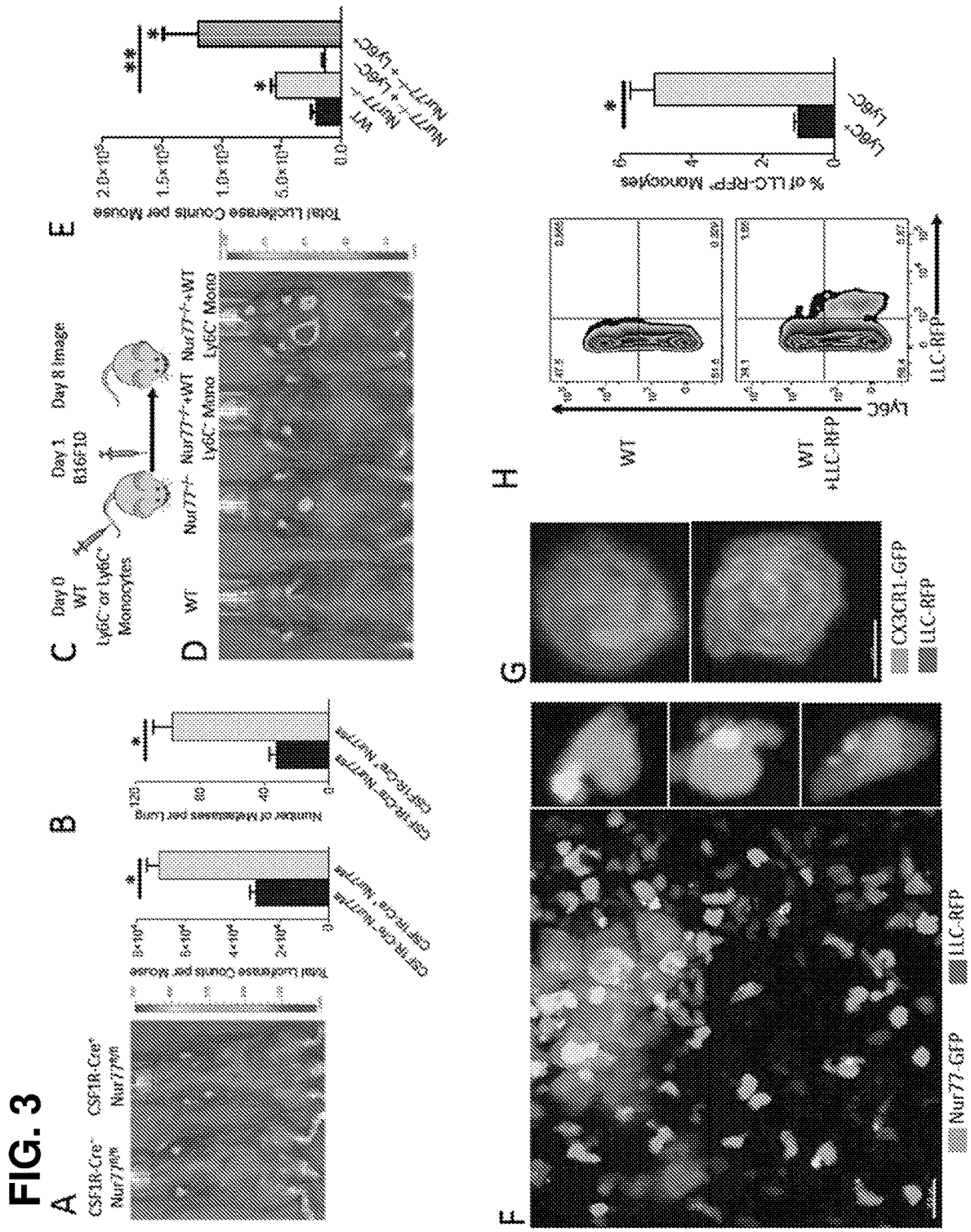

FIG. 3. Myeloid-specific Nur77 deletion increases tumor metastasis, while patrolling monocytes reduce tumor metastasis and engulf tumor material in the lung. (A) In vivo imaging (Left), and quantification (Right) of tumor in lungs of CSF1R-Cre$^-$Nur77$^{fl/fl}$ or CSF1RCre$^+$Nur77$^{fl/fl}$ mice 7 days after IV injection of 3×10$^5$ B16F10-luciferase tumor cells (n=6,*=p<0.01). (B) Quantification of the number of tumor metastases per lungs of CSF1RCre$^-$Nur77$^{fl/fl}$ and CSF1R-Cre$^+$Nur77$^{fl/fl}$ mice 7 days after IV injection of 3×10$^5$ B16F10-YFP tumor cells (n=8, *=p<0.01). (C) Nur77$^{-/-}$ mice were injected IV with 5×10$^5$ wild-type Ly6C$^-$ patrolling monocytes, Ly6C$^+$ inflammatory monocytes, or PBS at day 0. On day 1, 3×10$^5$ B16F10-luciferase tumor cells were injected IV and tumor metastasis and growth was measured by in vivo imaging at day 8. Representative in vivo imaging (D), and quantification (E) of B16F10-luciferase metastasis 8 days after monocyte transfer and 7 days after tumor transfer in wild-type (WT) or Nur77$^{-/-}$ mice. (Data from 5 separate experiment with n=2 per group;*=p<0.01 statistically different than WT; **=p<0.05 statistically different than Nur77$^{-/-}$). (F) Imaging of tumor material uptake in lung by Nur77-GFP$^{high}$ monocytes 24 hrs after IV injection of LLC-RFP tumor cells. Representative higher magnification images to right. (G) Uptake of LLC-RFP tumor material by CX3CR1-GFP$^{high}$Ly6C$^-$ patrolling monocytes after 24 hrs of coculture. (H) Representative flow plot (Left) and quantification (Right) of tumor material uptake by all monocytes in the lung 24 hrs after IV tumor injection of 3×10$^5$ LLC-RFP cells (n=3*=p<0.01).

Figure 4:
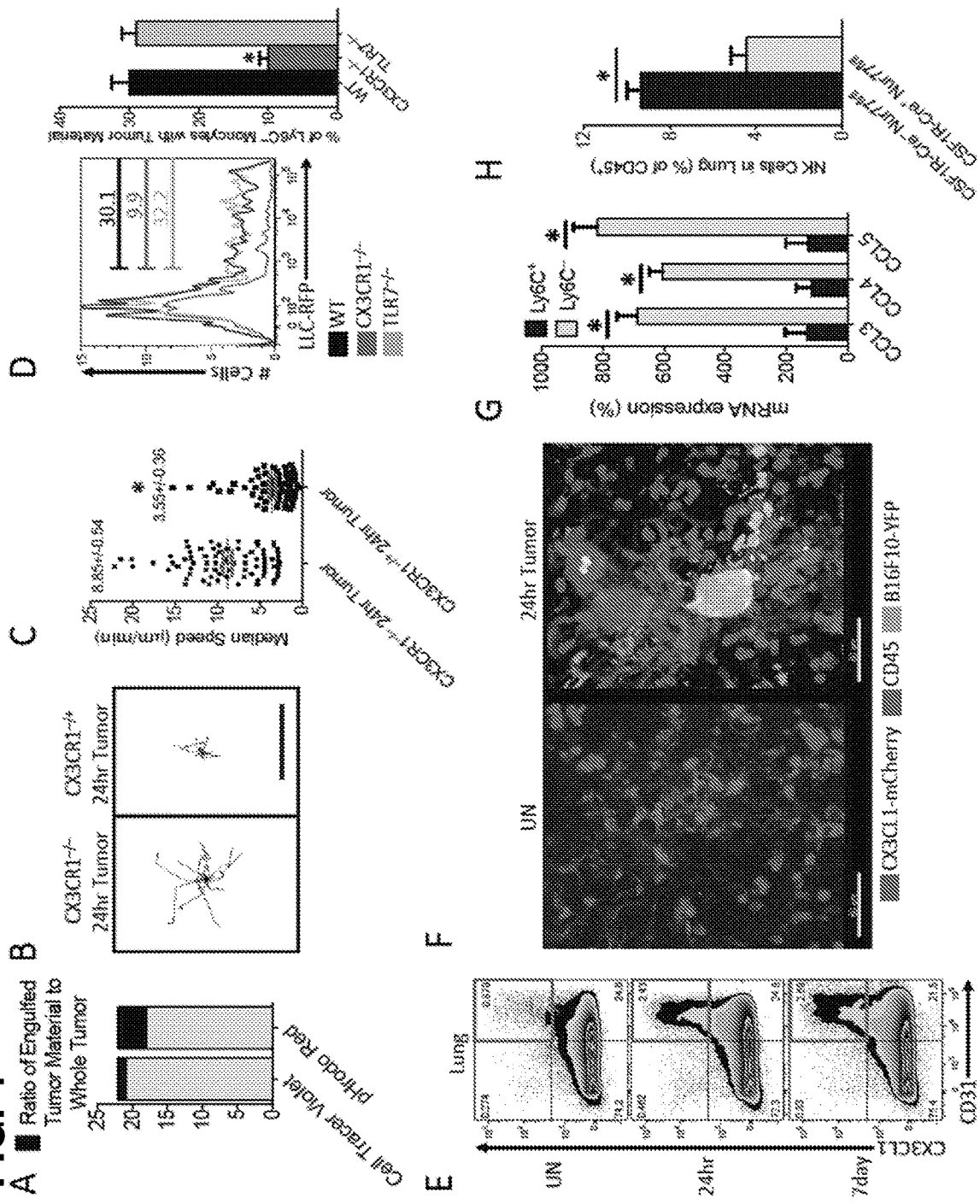

FIG. 4. Patrolling monocytes detect tumor material in a CX3CR1-dependent manner, and produce chemokines that recruit NK cells to the lung tumor environment. (A) Ratio of fluorescent intensity of tumor material engulfed by patrolling monocytes (black) to fluorescent intensity of whole tumor (black and grey) 3 hrs after IV LLC tumor injection. LLC tumors were labeled with either CellTrace Violet or a pH-sensitive pHrodo Red dye and then IV injected in a 1:1 ratio into a wild-type mouse. Tracking (B) and median speed (C) of CX3CR1$^{-/-}$ or CX3CR1$^{-/+}$ monocyte movement 24 hrs after IV tumor injection in the lung. Monocyte tracks transposed to a common origin from representative 20 min movies (scale bar=100 μm, n=3,*=p<0.001). (D) Percentage of Ly6C$^-$ patrolling monocytes containing LLC-RFP tumor material in the lung 3 hrs after IV injection of tumor into wild-type (WT), CX3CR1$^{-/-}$, or TLR7$^{-/-}$ mice. (E) Percentage of CD31$^+$ CX3CL1$^+$ lung endothelial cells isolated from Untreated (UN) or 24 hrs or 7 days after IV injection of B16F10-YFP tumor cells into CX3CL1-mCherry mice. (F) Imaging of CX3CL1-mCherry (Red) expression in lung 24 hrs after IV injection of B16F10-YFP tumor cells (Green) in CX3CL1-mCherry mice. CD45$^+$ immune cells are labeled in blue. (G) Relative chemokine mRNA expression in Ly6C$^+$ or Ly6C$^-$ monocytes isolated from lung by FACS 24 hrs after IV B16F10 tumor injection (n=3, *=p<0.01). (H) Number of natural killer (NK) cells in the lung of CSF1R-Cre$^-$Nur77$^{fl/fl}$ or CSF1R-Cre$^+$Nur77$^{fl/fl}$ mice 7 days after IV injection of 3×10$^5$ B16F10-luciferase tumor cells (n=5, *=p<0.01).

Figure 5:
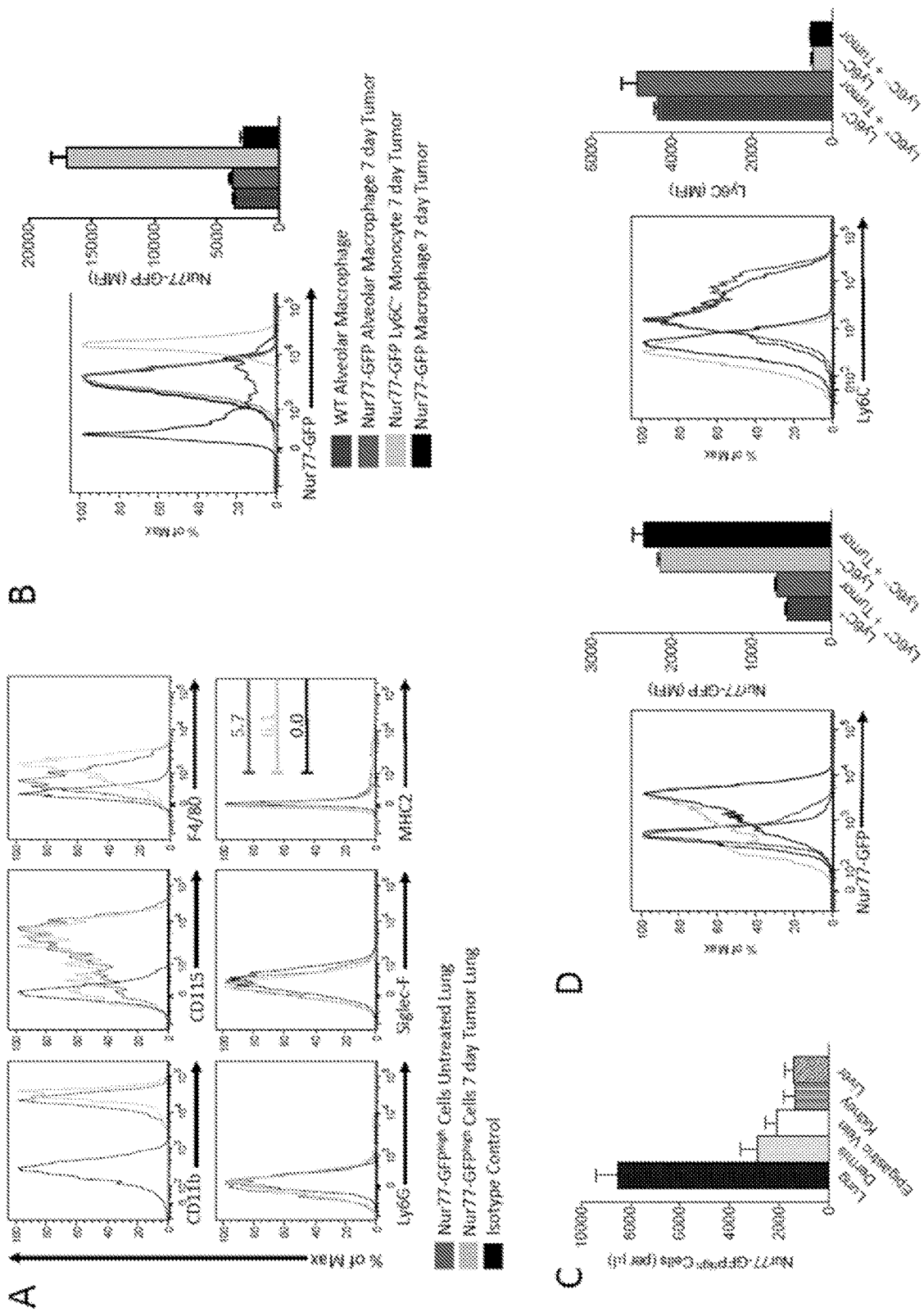

FIG. 5. Identification and quantification of Nur77-GFP$^{high}$ monocytes in the lung. (A) Surface expression of CD11b, CD115, F4/80, Ly6G, Siglec-F and MHC2 on all CD45$^+$CD11c$^{low}$Nur77-GFP$^{high}$ cells isolated from Untreated or 7 day LLC tumor treated lung. Staining was compared to a negative isotype antibody control. Gates for MHC2 provide percentages of positive cells stained above isotype control. (B) CD11c$^{high}$ alveolar macrophages, MHC2$^+$CD11b$^+$ macrophages, and Ly6C$^-$MHC2$^-$CD11b$^+$ patrolling monocytes were isolated from Nur77-GFP or Wild-type (WT) mice 7 day after LLC tumor transfer and compared for GFP expression by flow cytometry. Note: Wild-type (WT) GFP$^-$ alveolar macrophages exhibit autofluorescence in the GFP channel, but no true Nur77-GFP expression. (C) Comparison of Nur77-GFP$^{high}$ patrolling cells per μl of blood volume in various tissues by live confocal microscopy (n=5 fields of view for each tissue). (D) Changes in Nur77-GFP (Left) and Ly6C (Right) expression on Ly6C$^-$ or Ly6C$^+$ monocytes isolated by flow cytometry from Nur77-GFP mice and incubated for 24 hrs with B16F10 melanoma cells.

Figure 6:
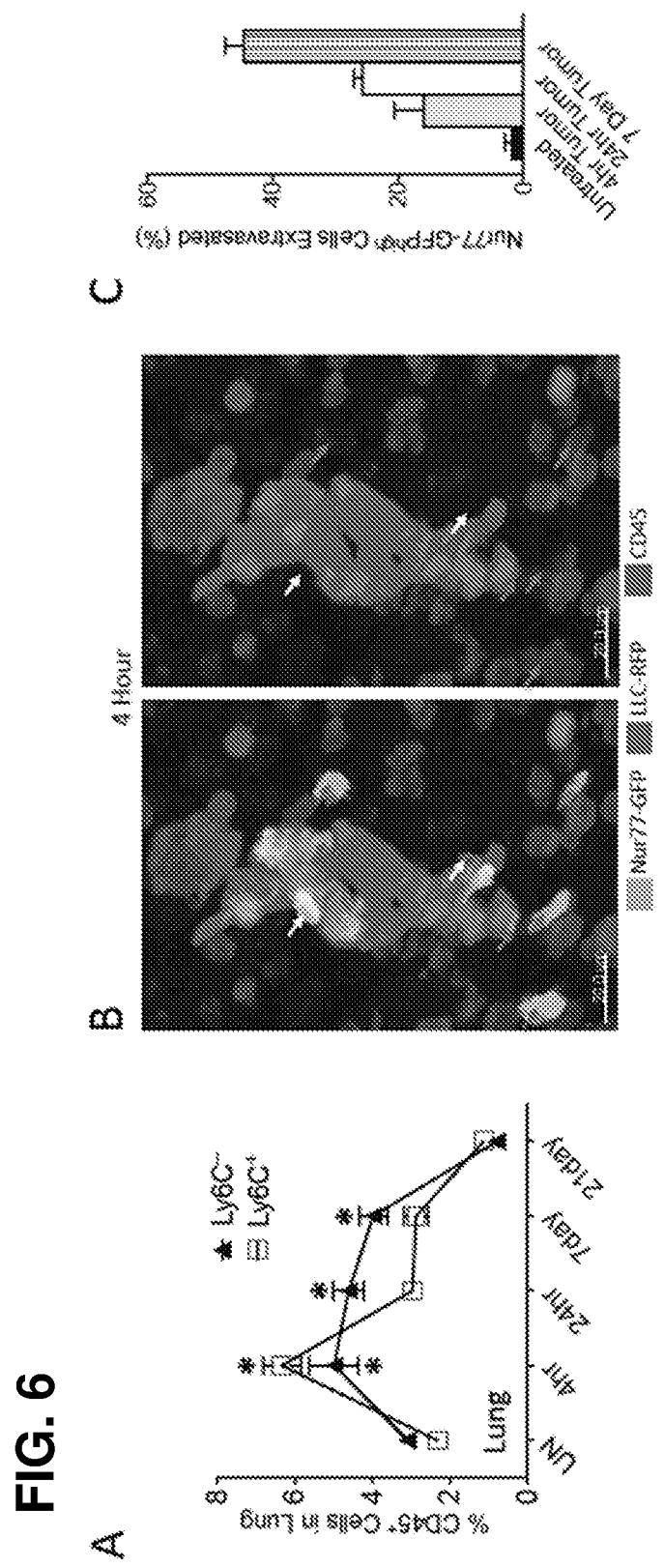

FIG. 6. Monocyte recruitment and extravasation in the lung after tumor inoculation. (A) Percentages of Ly6C$^-$ or Ly6C$^+$ monocytes from all CD45$^+$ immune cells in lungs of Untreated (UN) mice and, 4 hrs, 24 hrs, 7 days or 21 days after LLC-RFP IV transfer (*=p<0.01 different form UN for each group). (B) Imaging of Nur77-GFP$^{high}$ patrolling monocytes (Green) in the lung at 4 hrs after IV injection of Nur77-GFP mice with 3×10$^5$ LLC-RFP (Red) cells. Immune cells in the vasculature were labeled with IV injected anti-CD45 antibody (Blue). Red arrows are Nur77-GFP$^{high}$CD45$^+$ monocytes in the vasculature. White arrows indicate Nur77-GFP$^{high}$CD45$^-$ monocytes that have extravagated out of the vasculature. (C) Quantification of confocal images of the percentages of Nur77-GFP$^{high}$ patrolling monocytes extravagated at tumor sites of lung at 4 hrs, 24 hrs and 7 days after IV LLC-RFP transfer (average of 3 tumor sites from 3 separate mice for each time point).

Figure 7:
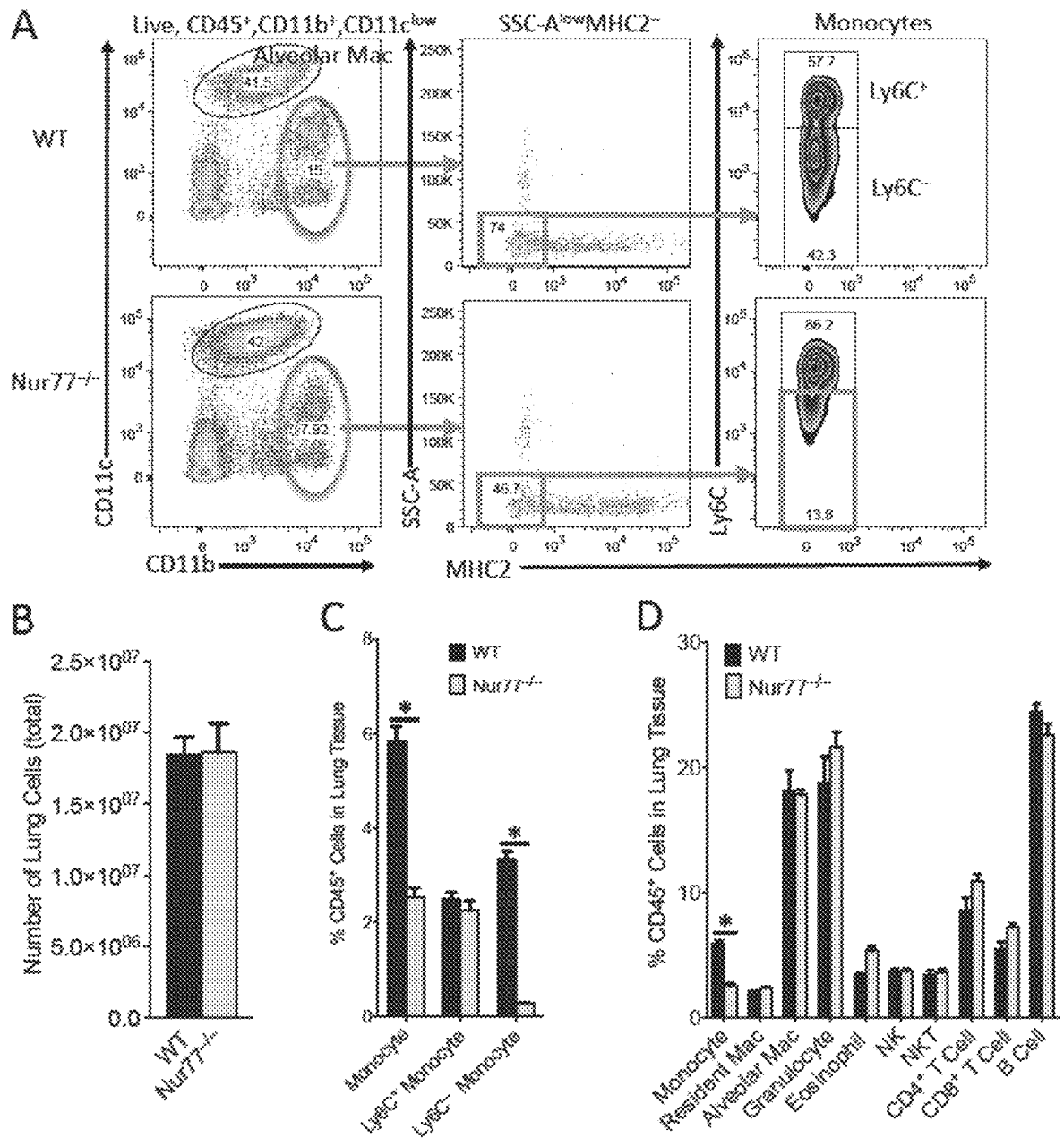

FIG. 7. Ly6C$^-$ monocytes are selectively missing in the lung of Nur77$^{-/-}$ mice. (A) Identification of monocyte and alveolar macrophage populations in control (WT), and Nur77 knockout (Nur77$^{-/-}$) mouse lung by flow cytometry. Samples were pregated on Live CD45+ cells, then CD11b$^+$ CD11c$^{low}$ myeloid cells, then SSC$^{low}$ MCH2$^{low}$ monocytes were examined for Lv6C expression. (B) Total number of lung cells. (C) Percentage of monocytes out of all CD45$^+$ immune cells, and (D) percentage of other immune cell populations in control (WT) and Nur77 knockout (Nur77$^{-/-}$) mouse lung. (n=6 for each group; *=p<0.01)

Figure 8:
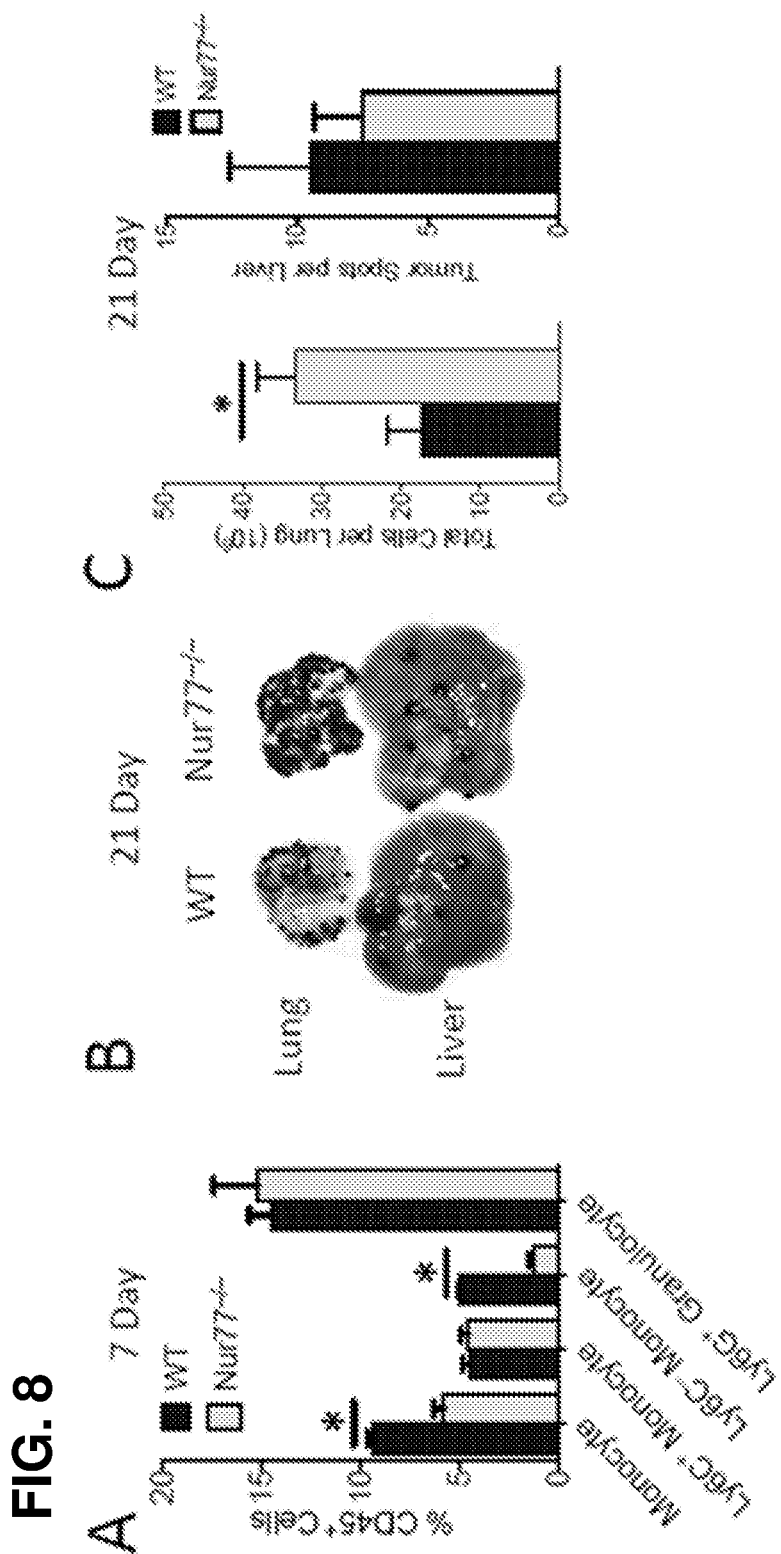

FIG. 8. Increased lung metastasis and growth of B16F10 melanoma in Nur77$^{-/-}$ mice. (A) Percentage of Ly6C$^+$ monocytes, Ly6C$^-$ monocytes, and Ly6G$^+$ granulocytes in the lung tumor environment of wild-type (WT) or Nur77$^{-/-}$ mice 7 days after IV injection of 3×10$^5$ B16F10-luciferase cells. (*=p<0.001 n=6). (B) Representative lung (top) and liver (bottom) at 21 days, (C) quantification of total cells per lung (left), and number of tumor spots per liver (right) at 21 days. (*=p<0.01 n=5)

Figure 9:
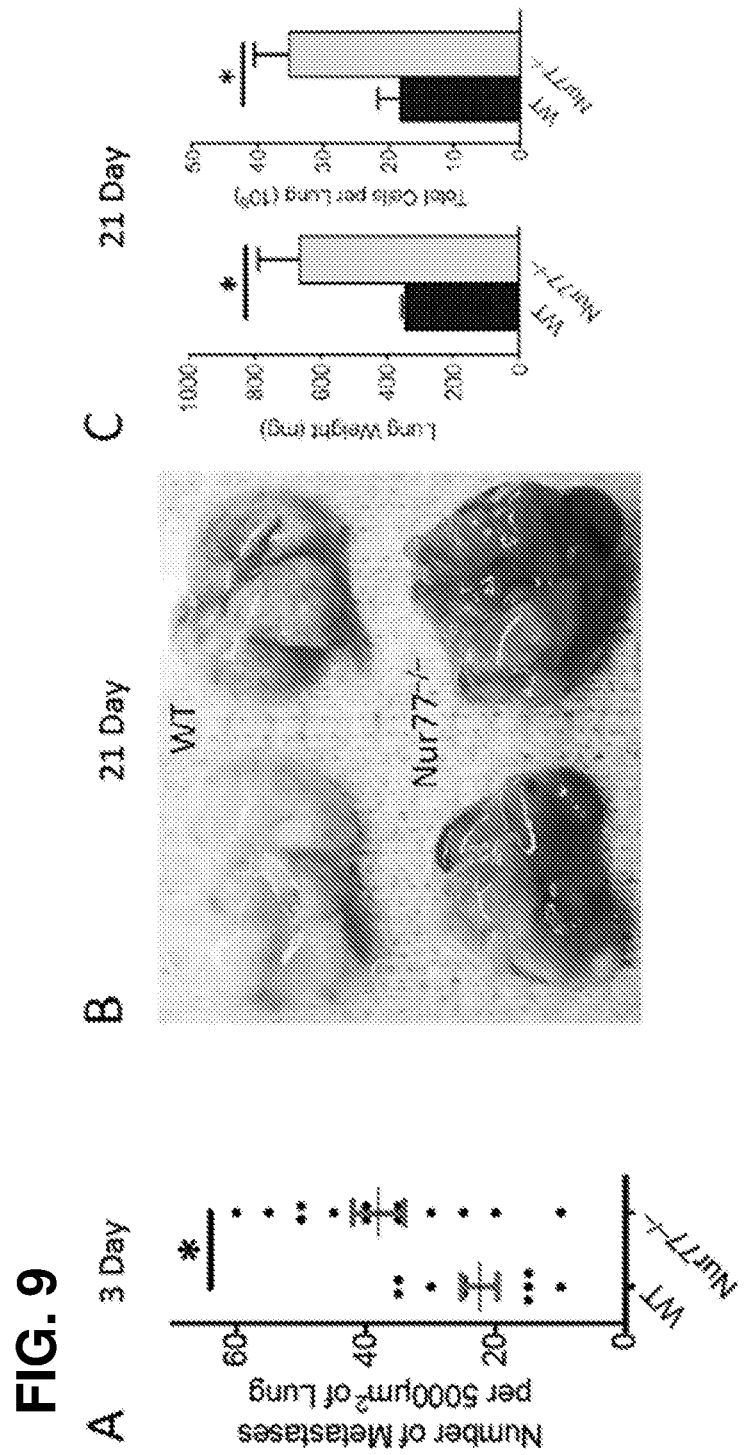

FIG. 9. Increased lung metastasis and growth of Lewis Lung Carcinoma (LLC) in Nur77$^{-/-}$ mice. (A) Number of metastases per 5000 μm$^2$ of lung as measured by confocal imaging of lung surface 3 days after IV injection of 3×10$^5$ LLC-RFP cells in wild-type (WT) or Nur77$^{-/-}$ mice (*=p<0.01 n=10). (B) Representative lung images at 21 days after IV injection of 3×10$^5$ LLC cells. (C) Lung weight (left) and cell number (right) 21 days after IV LLC injection. (*=p<0.01 n=6)

Figure 10:
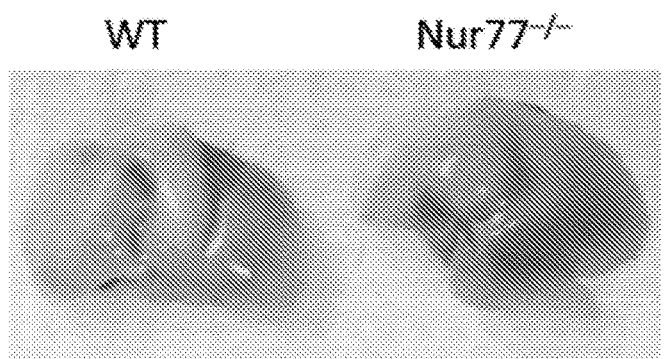
Figure 10:
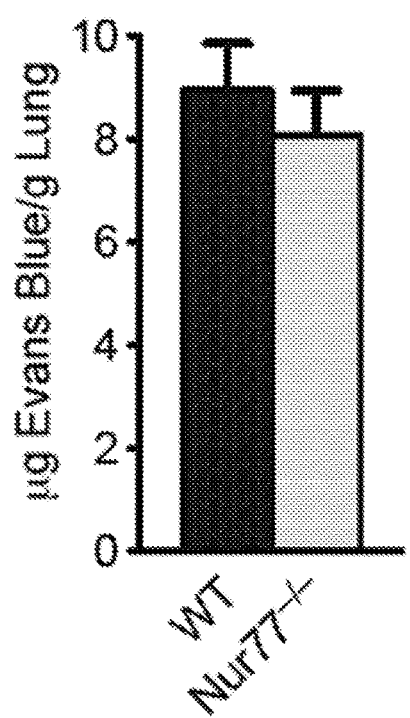

FIG. 10. No difference in vascular permeability between WT or Nur77$^{-/-}$ mice. (A) Representative Evans blue dye staining of lung tissue from wild-type (WT) or Nur77$^{-/-}$ mice. (B) Quantification of Evans blue dye/gram of lung tissue. Mice were injected IV with 30 mg/kg Evans blue dye, dye was allowed to circulate for 30 min, and then mice were sacrificed and analyzed. (n=6)

Figure 11:
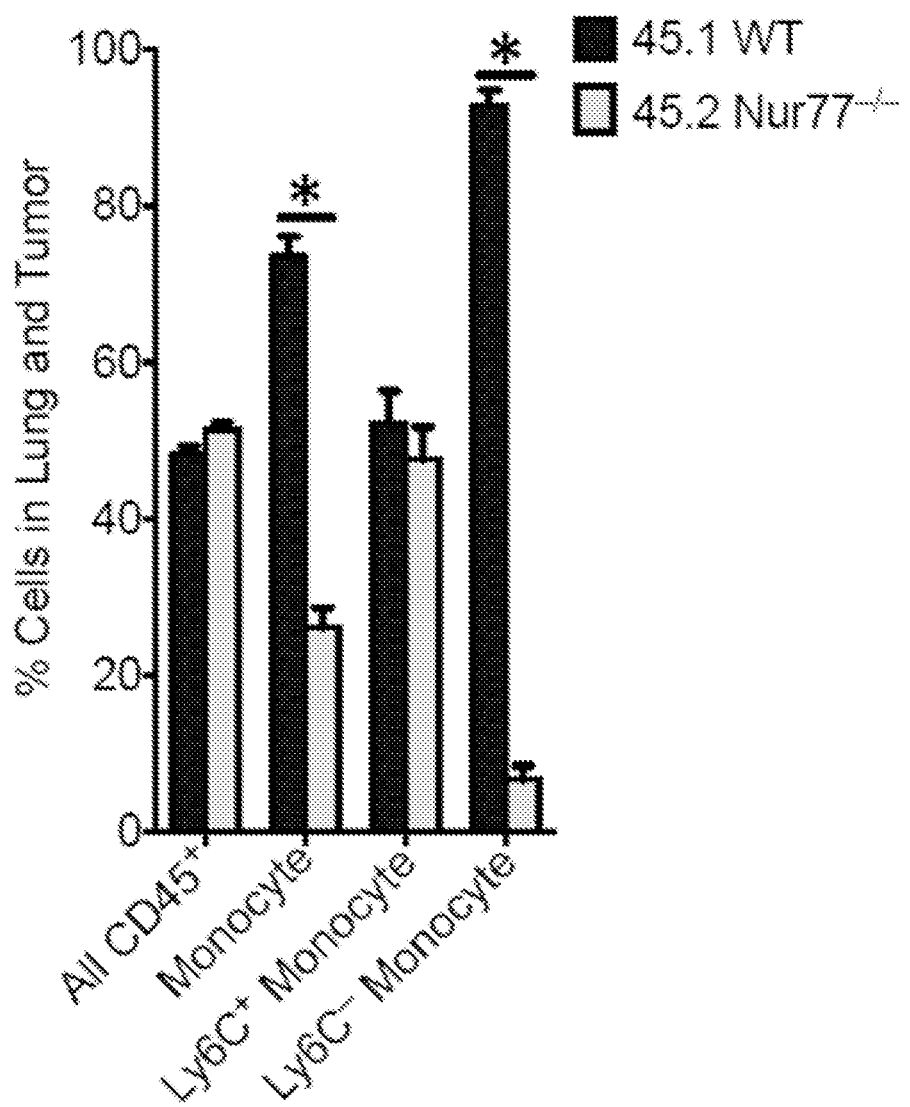

FIG. 11. Immune cell reconstitution in the lung of 1:1 (WT:Nur77$^{-/-}$) mixed chimera mice at 14 days after IV B16F10 tumor cell injection. A 1:1 CD45.2 Nur77$^{-/-}$: CD45.1 wild-type (WT) mixture of bone marrow was transplanted into CD45.2 WT mice, and mice were allowed to reconstitute for 6 weeks. At 6 weeks, 3×10$^5$ luciferase expressing B16F10 melanoma cells were injected IV. Percentages of CD45.2 Nur77$^{-/-}$ and CD45.1 WT immune cells that are present in lung after 14 days of tumor growth.

Figure 12:
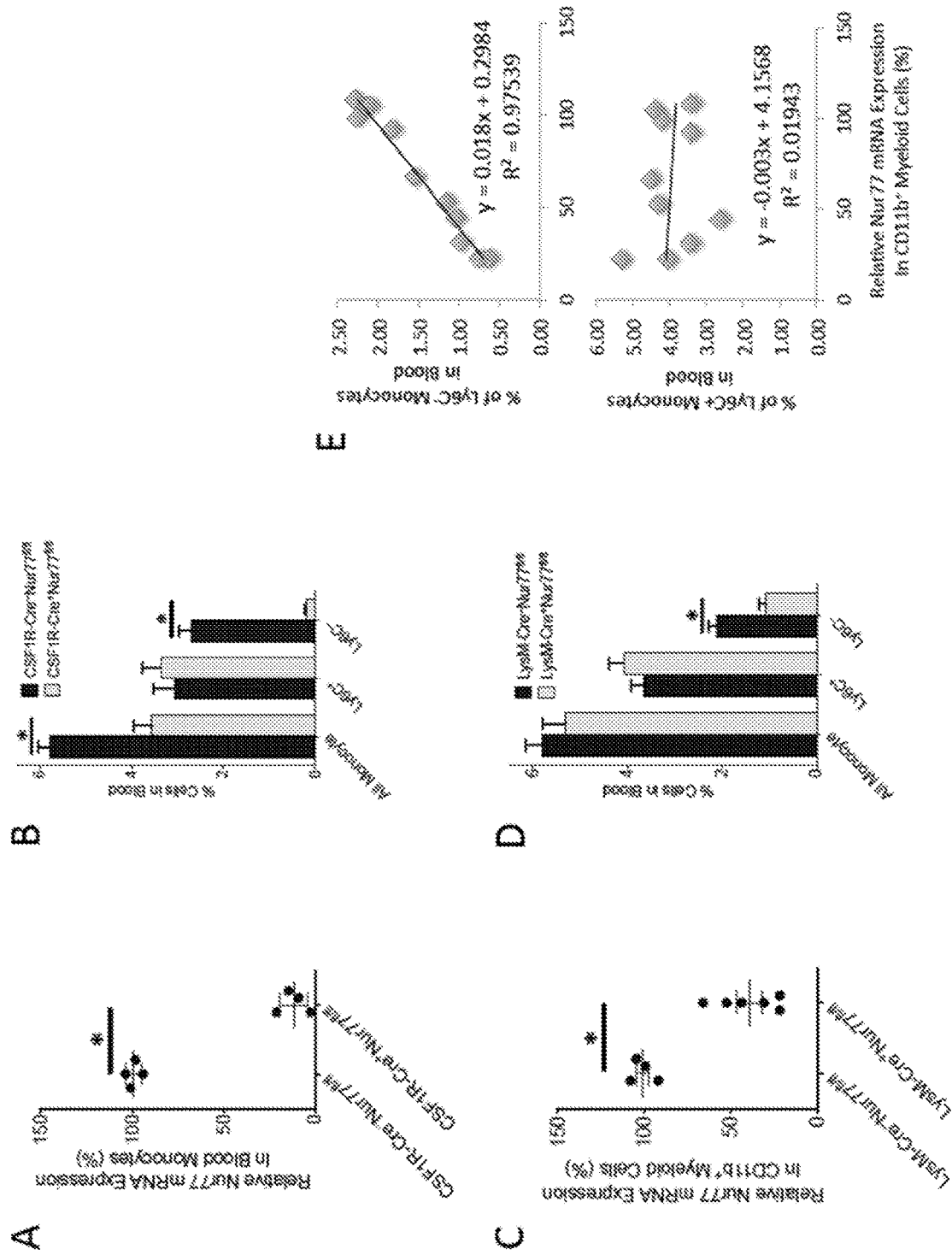

FIG. 12. CSF1R-Cre$^+$Nur77$^{fl/fl}$ and LysM-Cre$^+$Nur77$^{fl/fl}$ mice have reduced Nur77 expression in myeloid cells that directly correlate with reduced Ly6C$^{-/-}$ monocyte populations. (A) Reduced Nur77 mRNA expression levels in blood CD115$^+$ CD11b$^+$ monocytes from CSF1R-Cre$^+$Nur77$^{fl/fl}$ mice. (B) Analysis of monocyte subsets in blood of CSF1R-Cre$^+$Nur77$^{fl/fl}$ mice. (C) Reduced Nur77 mRNA expression in CD11b$^+$ spleen cells from LysM-Cre$^+$Nur77$^{fl/fl}$ mice. (D) Analysis of monocyte subsets in blood of LysM-Cre$^+$ Nur77$^{fl/fl}$ mice. (E) Correlation of Nur77 mRNA expression levels with Ly6C$^-$ (top) or Ly6C$^+$ (bottom) monocyte populations in blood of LysM-Cre$^+$Nur77$^{fl/fl}$ mice.

Figure 13:
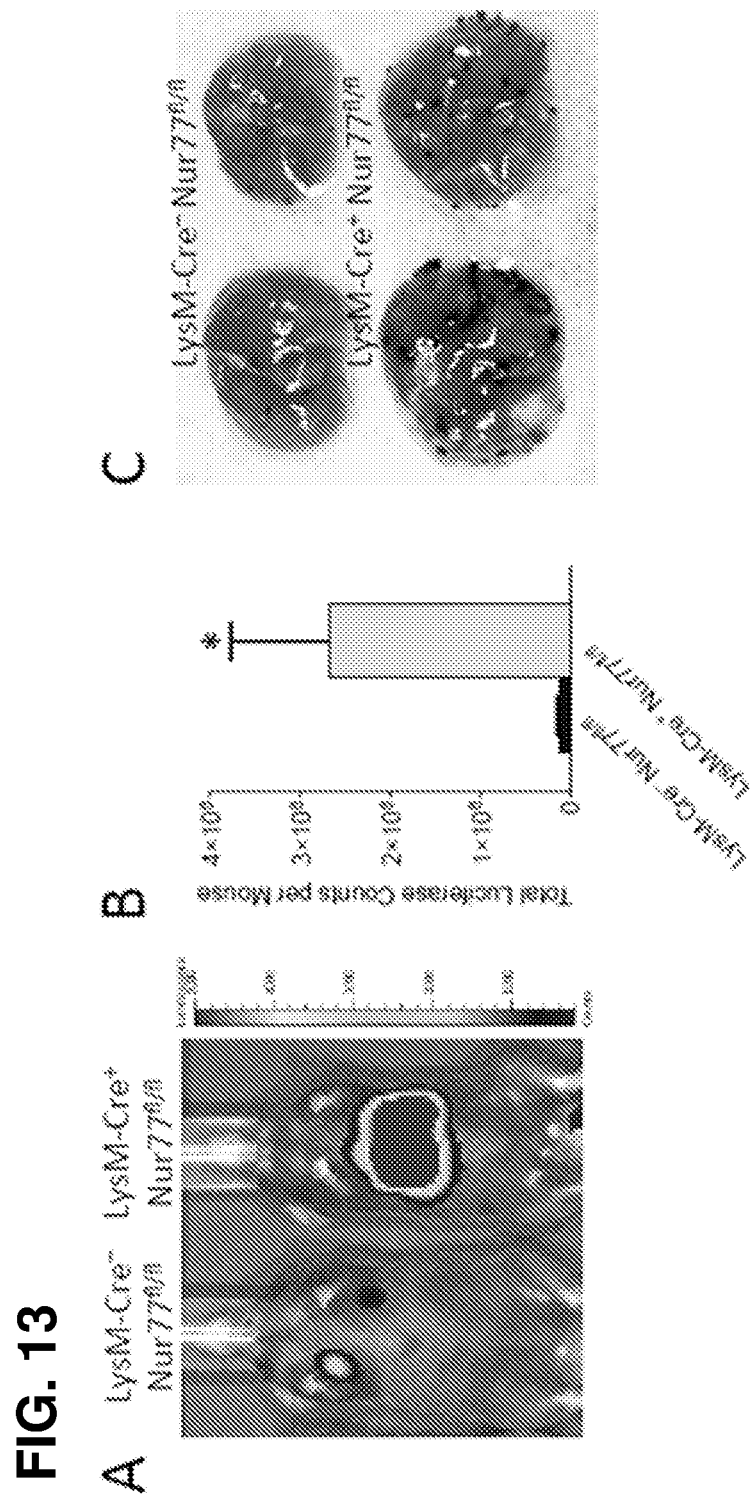

FIG. 13. Increased tumor with myeloid specific Nur77 deletion. In vivo imaging (A), quantification (B), and representative lung images (C) of tumors in lungs of LysM-Cre$^-$Nur77$^{fl/fl}$ or LysM-Cre$^+$Nur77$^{fl/fl}$ mice 14 days after IV injection of 3×10$^5$ B16F10-luciferase tumor cells (n=5. *=p<0.011.

Figure 14:
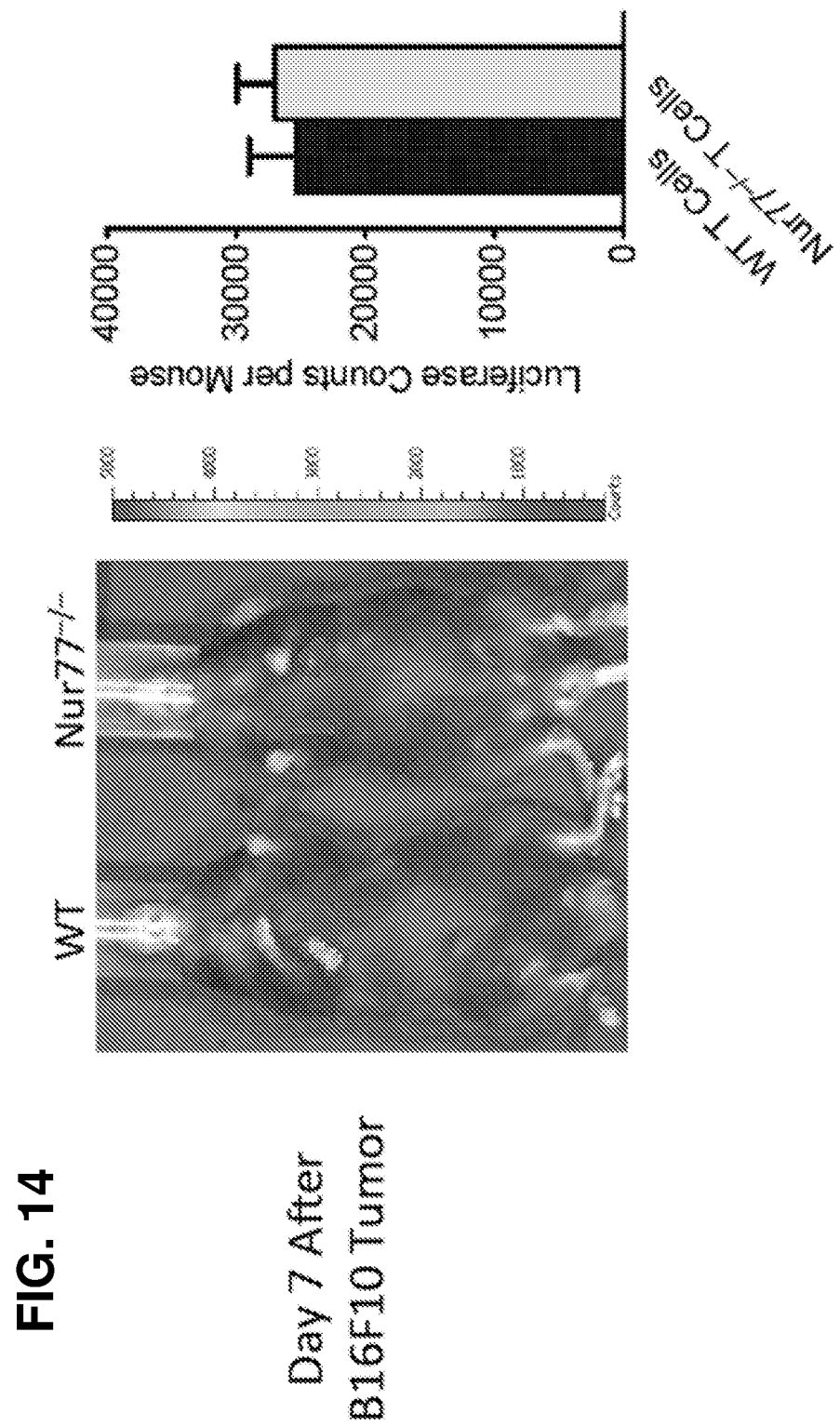

FIG. 14. No difference in B16F10 metastasis and growth in the lung of Rag1$^{-/-}$ mice reconstituted with WT or Nur77$^{-/-}$ T Lymphocytes. Representative imaging (left) and quantification (right) of B16F10 tumor growth 7 days after IV injection of 3×10$^5$ B16F10-luciferase cells in Rag$^{-/-}$ mice reconstituted with either WT or Nur77$^{-/-}$ naïve T cells. (n=5 per group)

Figure 15:
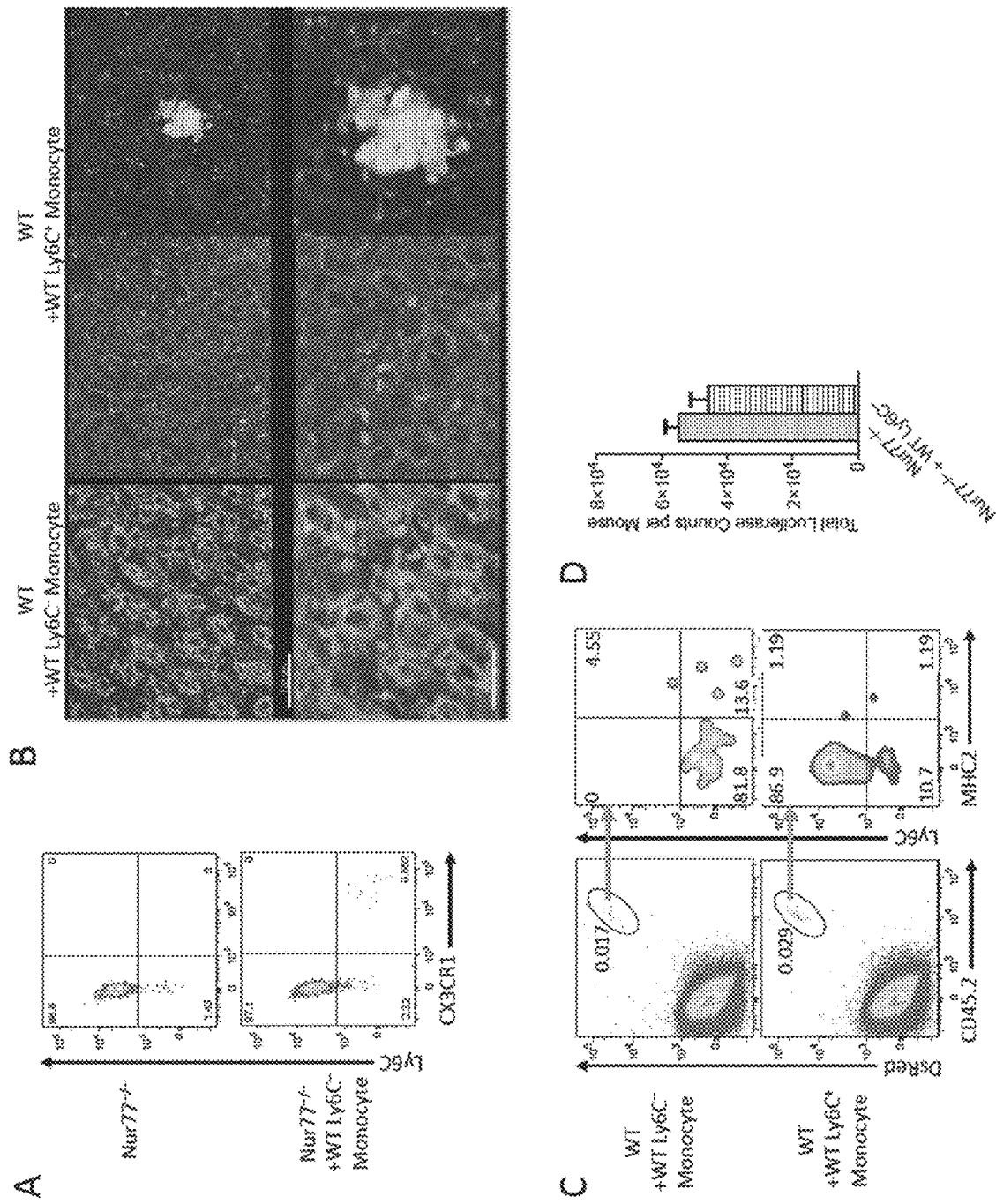

FIG. 15. Identification of transferred monocytes in mouse lung after tumor inoculation. (A) Identification of transferred wild-type (WT) Ly6C$^-$ CX3CR1-GFP$^{high}$ monocytes in the lung of Nur77$^{-/-}$ mice by flow cytometry at 10 days after monocyte injection and 9 days after IV injection of B16F10-luciferase tumor. (B-C) Identification of WT Ly6C$^-$ CD45.2$^+$ DsRed$^+$ or Ly6C$^+$ DsRed$^+$ CD45.2$^+$ monocytes transferred into WT CD45.1$^+$ mice 8 days after monocyte injection and 7 days after IV injection of B16F10-luciferase tumor. (B) Identification of transferred WT Ly6C$^-$ DsRed$^+$ or Ly6C$^+$ DsRed$^+$ monocytes in lung by confocal imaging (Red=Transferred cells, Green=Autofluorescence of collagen-dim and tumor-bright). (C) Identification of transferred Ly6C$^-$ DsRed$^+$ CD45.2$^+$ or Ly6C$^+$ DsRed$^+$ CD45.2$^+$ monocytes in blood by flow cytometry. (D) 7 day B16F10-luciferase tumor metastasis in Nur77$^{-/-}$ mice when 5×10$^5$ WT Ly6C$^-$ patrolling monocytes are transferred 24 hrs after tumor inoculation (n=7).

Figure 16:
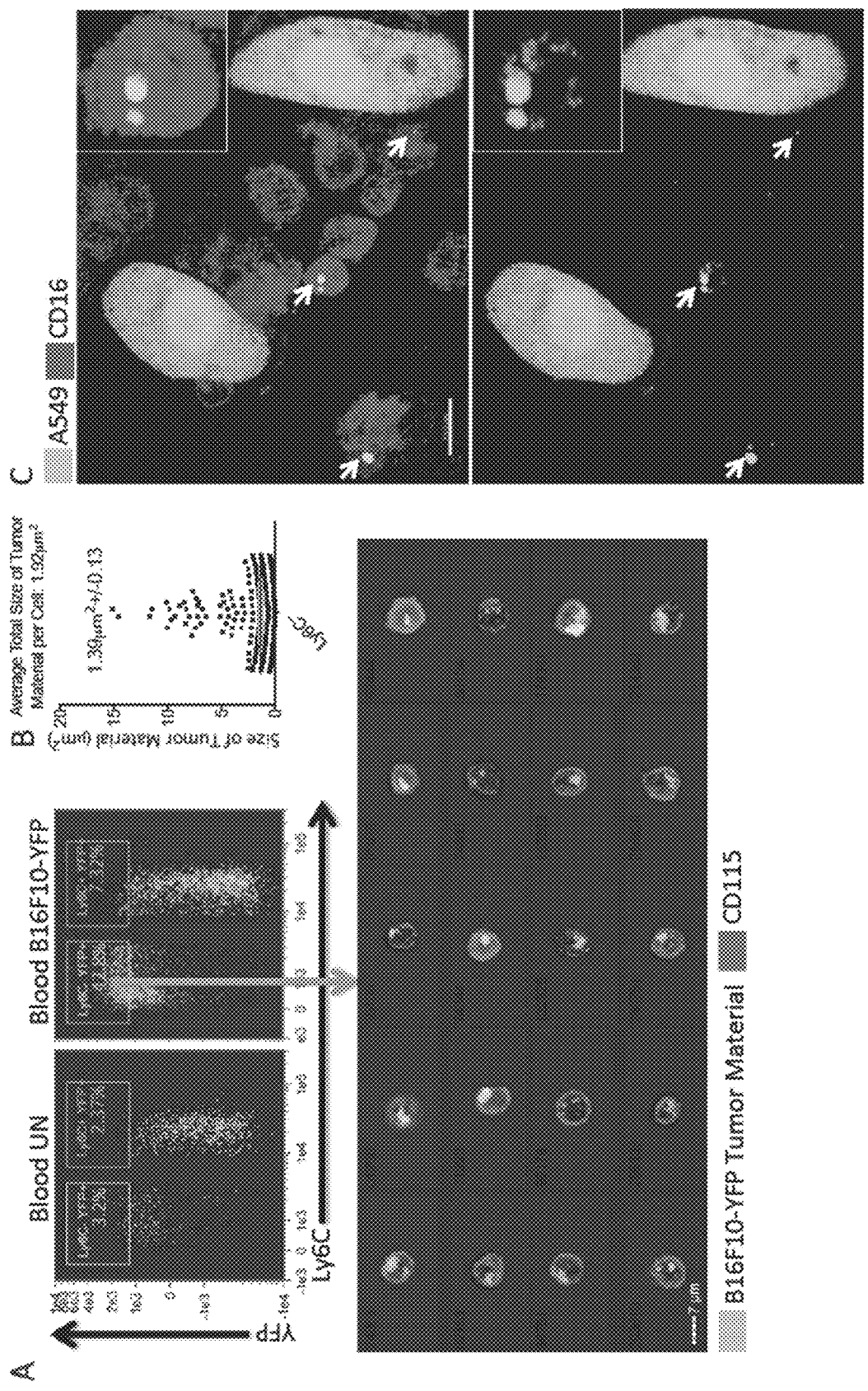

FIG. 16. Tumor material uptake by patrolling monocytes. (A) Analysis of B16F10-YFP tumor material uptake in Ly6C$^-$ or Ly6C$^+$ monocytes analyzed by ImageStream imaging cytometry. Monocytes were gated on Lin$^-$CD115$^+$ CD11b$^+$SSC$^{low}$ in-focus cells, and then gated on Ly6C$^-$ and Ly6C$^+$ populations from blood 24 hrs after IV injection of 5×10$^5$ B16F10-YFP tumor cells. Representative images of B16F10-YFP tumor material (Green) in CD115$^+$(Purple) Ly6C$^-$ monocytes transferred with B16F10-YFP tumor (Lower Panel). (B) Quantification of average size of B16F10-YFP tumor material and total size of tumor material per Ly6C$^-$ monocyte. (C) Imaging of A549 human lung carcinoma material uptake by CD14$^{dim}$CD16+ human monocytes after 24 hrs of coculture. Monocytes are labeled with CD16 (blue) and tumor/tumor material is labeled with CellTracker Green (arrows mark monocyte uptake of tumor, high magnification image of representative monocyte in upper right corner).

Figure 17:
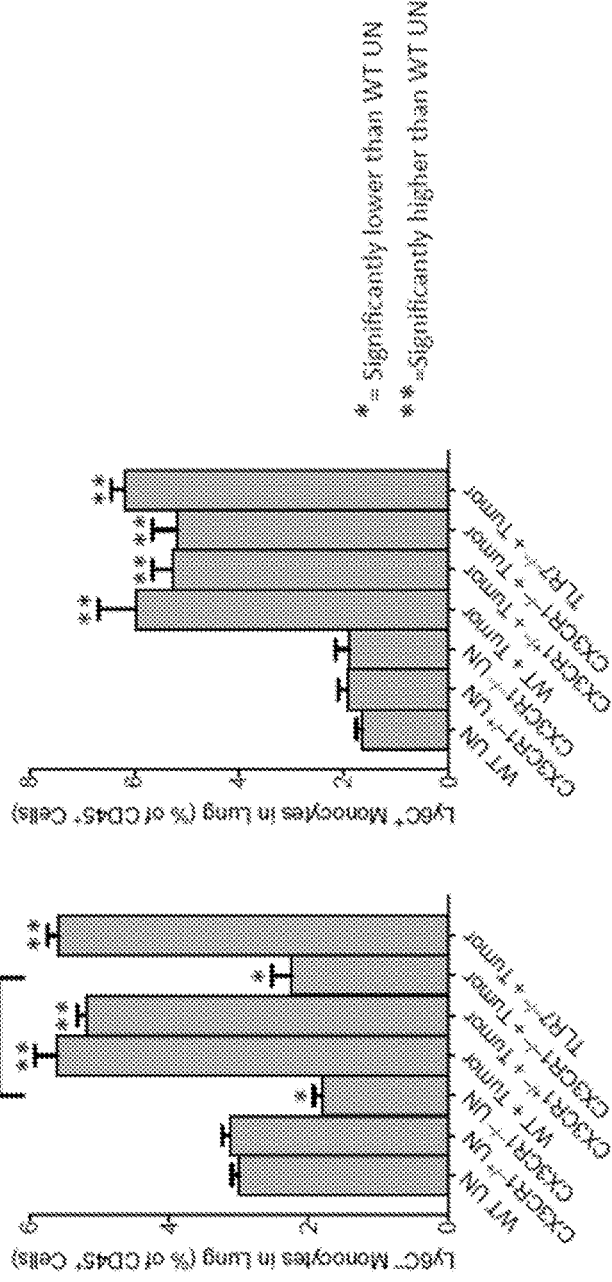
Figure 17:
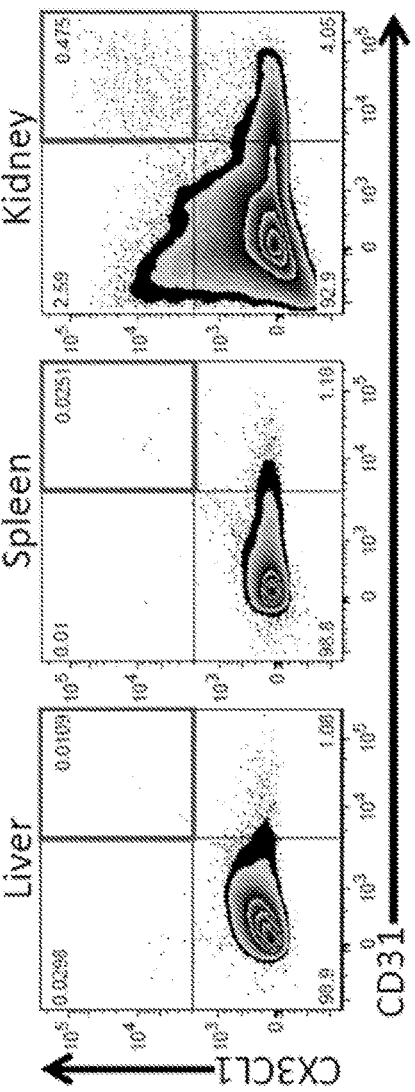

FIG. 17. CX3CR1-dependent recruitment of Ly6C$^-$ monocytes to the lung in response to tumor. (A) Change in the percentages of Ly6C$^-$ (Left) or Ly6C$^+$ (Right) monocytes in the lung of wild-type (WT), CX3CR1$^{-/-}$, CX3CR1$^{+/-}$ or TLR7$^{-/-}$ mice either untreated (UN) or at 24 hrs after IV injection of 3×10$^5$ LLC-RFP tumor cells (+ Tumor). (B) Percentages of CD31$^+$ CX3CL1$^+$ lung endothelial cells in CX3CL1-mCherry mouse liver, spleen or kidney in untreated mice.

Figure 18:
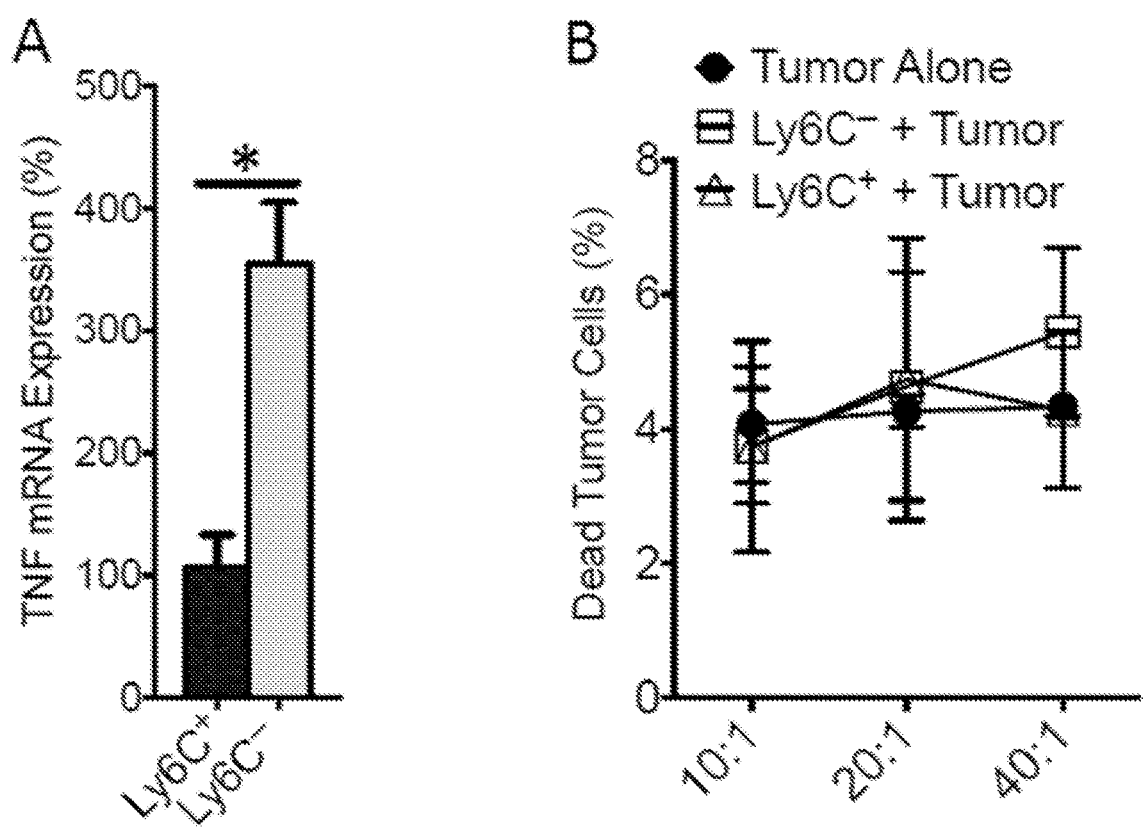

FIG. 18. Elevated TNFα production by Ly6C$^-$ monocytes, but no direct tumor killing ability. (A) Relative TNFα (TNF) mRNA expression in Ly6C$^+$ or Ly6C$^-$ monocyte isolated from lung by FACS 24 hrs after IV B16F10 tumor injection (n=3, *=p<0.01). (B) Direct tumor killing ability of Lv6C$^-$ or Ly6C+ monocyte subsets isolated by flow cytometry from Nur77$^-$ GFP mice stimulated for 24 hrs with LPS/IFNγ, and then co-cultured for 24 hrs with B16F10 melanoma cells at 10:1, 20:1 or 40:1 monocyte to tumor cell ratios (n=3 per group).

Figure 19:
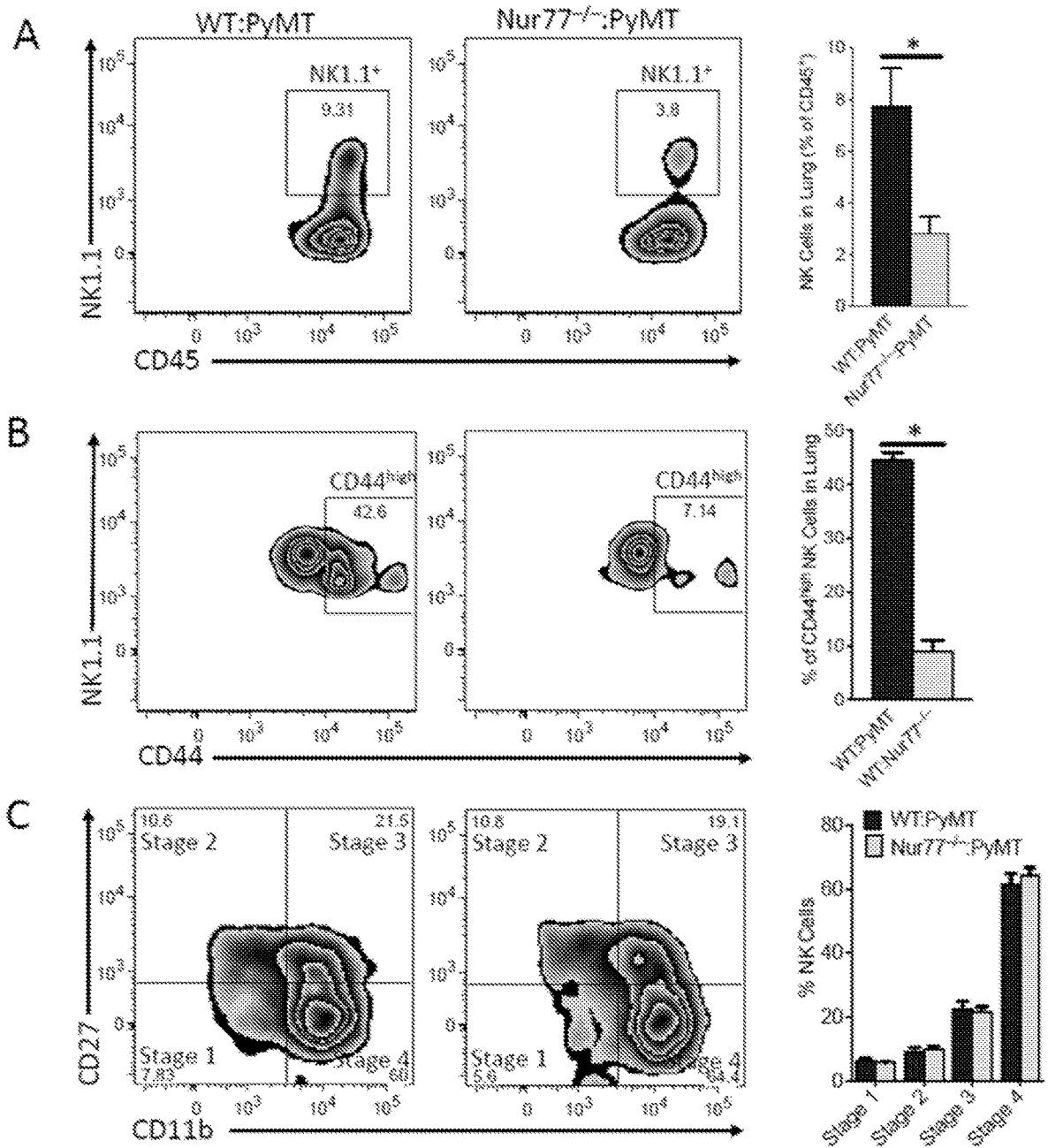

FIG. 19. Reduced Natural Killer cells recruitment and activation in the lung of MMTV-PyMT mice receiving Nur77-deficient bone marrow. (A) Percentage of NK1.1+ Natural Killer (NK) cells out of all CD45+ immune cells in the lung of MMTV-PyMT mice reconstituted with WT (WT:PyMT) or Nur77−/− (Nur77−/−:PyMT) bone marrow (n=5, *p=0.02). (B) Percentage of CD44$^{high}$NK1.1+ NK cells isolated from the lung of MMTV-PyMT mice reconstituted with WT (WT:PyMT) or Nur77−/− (Nur77−/−:PyMT) bone marrow (n=5, *p=0.005). (C) Developmental stages of NK1.1+ NK cell populations as measured by CD11 b and CD27 expression in the lung of MMTV-PyMT mice reconstituted with WT (WT:PyMT) or Nur77−/− (Nur77−/−:PyMT) bone marrow.

Figure 20:
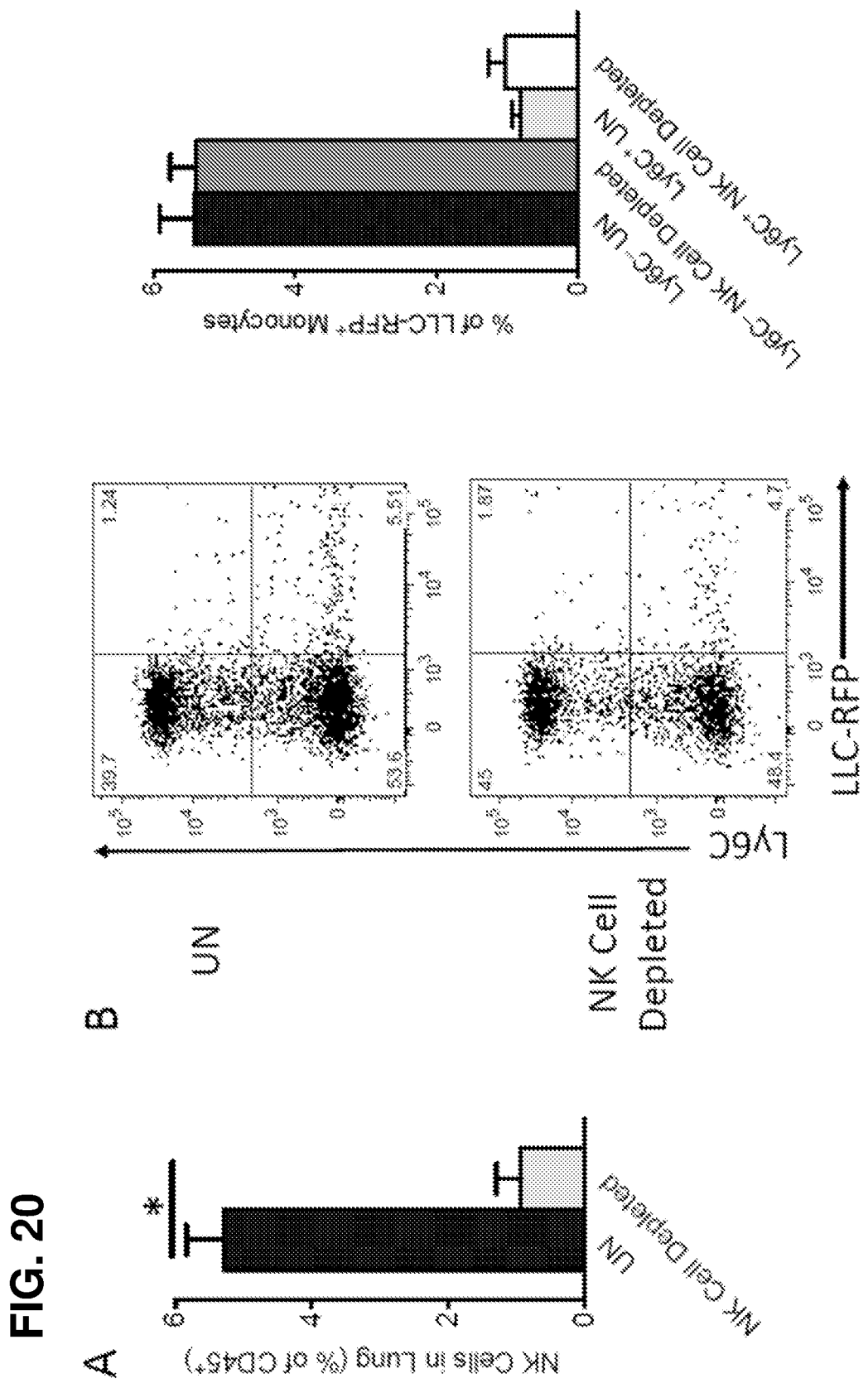

FIG. 20. Natural Killer cell depletion does not affect tumor material uptake by monocytes. (A) Quantification of Natural Killer (NK) cell depletion in the lung 48 hrs after IV anti-NK1.1 antibody depletion. (B) Representative flow plots (Left) and quantification (right) or LLC-RFP tumor material uptake by with Ly6C− and Ly6C+ monocyte populations 24 hrs after IV tumor injection and 48 hours after IV anti-NK1.1 antibody depletion (n=4 p<0.01).

FIG. 21. Mechanism for regulation of tumor metastasis by patrolling monocytes 1. Induction of vascular damage and inflammation by tumor extravasation. 2. Expression of CX3CL1 by endothelial cells. 3. Recruitment of patrolling monocytes to site of vascular damage and tumor. 4. Uptake of tumor material by patrolling monocytes. 5. Release of CCL3/4/5 from patrolling monocytes. 6. Recruitment and activation of NK cells. 7. NK cells kill tumor

DETAILED DESCRIPTION

The invention provides, inter alia, methods and uses of Nur77 polypeptides and subsequences, Nur77 agonists, CX3CR1 agonists, Nur77 regulated monocytes (e.g., CD14+ CD16+ or CD14$^{dim}$CD16+ (CD115+CD11b+GR1− (Ly6C−)) monocytes, or CD14+ CD16+ monocytes or CD14$^{dim}$CD16+ (CD115+CD11b+GR1− (Ly6C−)) monocytes contacted with a Nur77 agonist or contacted with a CX3CR1 agonist. Methods and uses include, for example, treatment of a condition or disorder in which modulation of patrolling monocytes provides a beneficial effect. Non-limiting examples include neoplasia, tumor, cancer, malignancy or metastases. Methods and uses can lead to suppression, inhibition, control or limiting neoplasia, tumor, cancer, malignancy or metastasis in a subject. For example, suppression, inhibition, control or limit an original (primary) site of neoplasia, tumor, cancer or malignancy to metastasis to a second or other site in a subject.

In accordance with the invention, there are provided methods and uses of reducing or inhibiting metastasis of a neoplasia, tumor, cancer or malignancy to one or more other sites, or formation or establishment of metastatic neoplasia, tumor, cancer or malignancy at other sites distinct and/or distal from a primary neoplasia, tumor, cancer or malignancy. In various embodiments, a method or use includes administering to a subject an amount of a Nur77 polypeptide, subsequence, Nur77 agonist, CX3CR1 agonist, Nur77 regulated monocytes (e.g., CD14+ CD16+ or CD14$^{dim}$CD16+ (CD115+CD11b+GR1− (Ly6C−)) monocytes, or CD14+ CD16+ monocytes or CD14$^{dim}$CD16+ (CD115+CD11b+GR1− (Ly6C−)) monocytes contacted with a Nur77 agonist or contacted with a CX3CR1 agonist to reduce or inhibit metastasis of the neoplasia, tumor, cancer or malignancy to other sites, or formation or establishment of metastatic neoplasia, tumor, cancer or malignancy at other sites distinct and/or distal from the primary neoplasia, tumor, cancer or malignancy.

Compositions, methods and uses of the invention include Nur77 polypeptides and subsequences and fragments of Nur77 polypeptides. Exemplary full length human Nur77 polypeptide sequences, as disclosed herein, have an amino acid length of about 611 and 598 amino acid residues (SEQ ID NO:1 and 2) as follows: Human NR4A1 protein sequence (*Homo sapiens* nuclear receptor subfamily 4, group A, member 1 (NR4A1), TR3, NGFIB) (SEQ ID NO:1):

```
>NP_001189162 length = 611
MWLAKACWSIQSEMPCIQAQYGTPAPSPGPRDHLASDPLTPEFIKPTMDL
ASPEAAPAAPTALPSFSTFMDGYTGEFDTFLYQLPGTVQPCSSASSSASS
TSSSSATSPASASFKFEDFQVYGCYPGPLSGPVDEALSSSGSDYYGSPCS
APSPSTPSFQPPQLSPWDGSFGHFSPSQTYEGLRAWTEQLPKASGPPQPP
AFFSFSPPTGPSPSLAQSPLKLFPSQATHQLGEGESYSMPTAFPGLAPTS
PHLEGSGILDTPVTSTKARSGAPGGSEGRCAVCGDNASCQHYGVRTCEGC
KGFFKRTVQKNAKYICLANKDCPVDKRRRNRCQFCRFQKCLAVGMVKEVV
RTDSLKGRRGRLPSKPKQPPDASPANLLTSLVRAHLDSGPSTAKLDYSKF
QELVLPHFGKEDAGDVQQFYDLLSGSLEVIRKWAEKIPGFAELSPADQDL
LLESAFLELFILRLAYRSKPGEGKLIFCSGLVLHRLQCARGFGDWIDSIL
AFSRSLHSLLVDVPAFACLSALVLITDRHGLQEPRRVEELQNRIASCLKE
HVAAVAGEPQPASCLSRLLGKLPELRTLCTQGLQRIFYLKLEDLVPPPPI
IDKIFMDTLPF
```

*Homo sapiens* nuclear receptor subfamily 4, group A, member 1 (NR4A1), with representative amino acid polymorphisms illustrated by bold/underlining (SEQ ID NO: 2):

```
>NP_002126 length = 598 > NP_775180 length = 598
MPCIQAQYGTPAPSPGPRDHLASDPLTPEFIKPTMDLASPEAAPAAPTAL
PSFSTFMDGYTGEFDTFLYQLPGTVQPCSSASSSASSTSSSATSPASAS
FKFEDFQVYGCYPGPLSGPVDEALSSSGSDYYGSPCSAPSPSTPSFQPPQ
LSPWDGSFGHFSPSQTYEGLRAWTEQLPKASGPPQPPAFFSFSPPTGPSP
SLAQSPLKLFPSQATHQLGEGESYSMPTAFPGLAPTSPHLEGSGILDTPV
TSTKARSGAPGGSEGRCAVCGDNASCQHYGVRTCEGCKGFFKRTVQKNAK
YICLANKDCPVDKRRRNRCQFCRFQKCLAVGMVKEVVRTDSLKGRRGRLP
SKPKQPPDASPANLLTSLVRAHLDSGPSTAKLDYSKFQELVLPHFGKEDA
GDVQQFYDLLSGSLEVIRKWAEKIPGFAELSPADQDLLLESAFLELFILR
LAYRSKPGEGKLIFCSGLVLHRLQCARGFGDWIDSILAFSRSLHSLLVDV
PAFACLSALVLITDRHGLQEPRRVEELQNRIASCLKEHVAAVAGEPQPAS
FYLKLEDLVPPPPIIDKIFMDTLPF
```

Representative Nur77 polymorphisms include one or more of the following seven amino acid substitutions of Nur77:

1) SNP rs1882118—(L) Leu to (V) Val at aa position 26
2) SNP rs113544195—(D) Asp to (G) Gly at aa position 36
3) SNP rs75476334—(T) Thr to (I) Ile at aa position 74
4) SNP rs61734310—(S) Ser to (L) Leu at aa position 137
5) SNP rs1042315—(G) Gly to (R) Arg at aa position 262
6) SNP rs1042316—(G) Gly to (A) Ala at aa position 262
7) SNP rs61751044—(A) Ala to (D) Asp at aa position 400.

Such full length mammalian (human) Nur77 polypeptide sequences, fragments/subsequences, polymorphisms and modified forms and variants as set forth herein, are also included as invention compositions, methods and uses.

A "polypeptide" refers to two, or more, amino acids linked by an amide or equivalent bond. A polypeptide can also be referred to herein, inter alia, as a protein, peptide, or an amino acid sequence. Polypeptides can form intra or intermolecular disulfide bonds. Polypeptides can also form higher order structures, such as multimers or oligomers, with the same or different polypeptide, or other molecules.

A Nur77 polypeptide refers to full length polypeptide sequence, as well as subsequences, fragments or portions, polymorphisms, variants and modified forms of Nur77 polypeptide, unless the context indicates otherwise. Such Nur77 subsequences, fragments, polymorphisms, variants and modified forms have at least a part of, a function or activity of an unmodified or reference Nur77 protein. In particular embodiments, a polymorphism, variant or modified form retains, at least a part of, a function or activity of a reference Nur77 protein.

A "functional polypeptide" or "active polypeptide" refers to a polymorphic, variant or modified polypeptide or subsequence thereof that possesses at least one partial function or activity (e.g., biological activity) characteristic of a native wild type or full length counterpart polypeptide. For example, Nur77 polypeptides of SEQ ID NOs:1 or 2, as disclosed herein, which function or activity can be identified through an assay. Polymorphisms, variants and modified forms of Nur77 polypeptide sequences, and such subsequences, polymorphisms, variants or modified forms typically retain, at least a part of, one or more functions or activities of a reference or an unmodified Nur77 polypeptide sequence are applicable in the invention Particular non-limiting examples of a function or activity of Nur77 polypeptide is to direct monocytes, in vitro and/or in vivo, to a tumor or cancer metastasis site, or increase or promote numbers of monocytes in a tumor or cancer metastasis site. Additional particular non-limiting examples of a function or activity of Nur77 polypeptide is to increase, stimulate, activate or promote, in vitro and/or in vivo, monocyte migration to or mobilization against a tumor or cancer metastasis. Further non-limiting examples of a function or activity of Nur77 polypeptide is to control, limit or decrease, in vitro and/or in vivo, metastasis of a tumor or cancer. Still further non-limiting examples of a function or activity of Nur77 polypeptide is to control, limit, or decrease metastasis of a tumor or cancer from an original site to one or more other sites, in vitro and/or in vivo.

Such functions and activities are also desirable and therefore also applicable to Nur77 agonists, CX3CR1 agonists, Nur77 regulated monocytes (e.g., CD14$^+$ CD16$^+$ or CD14$^{dim}$CD16$^+$ (CD115$^+$CD11b$^+$GR1$^-$ (Ly6C−)) monocytes, or CD14$^+$ CD16$^+$ monocytes or CD14$^{dim}$CD16$^+$ (CD115$^+$CD11b$^+$GR1$^-$ (Ly6C−)) monocytes contacted with a Nur77 agonist or contacted with a CX3CR1 agonist. Accordingly, Nur77 polypeptide sequences, Nur77 agonists, CX3CR1 agonists, Nur77 regulated monocytes (e.g., CD14$^+$ CD16$^+$ or CD14$^{dim}$CD16$^+$ (CD115$^+$CD11b$^+$GR1$^-$ (Ly6C−)) monocytes, or CD14$^+$ CD16$^+$ monocytes or CD14$^{dim}$CD16$^+$ (CD115$^+$CD11b$^+$GR1$^-$ (Ly6C−)) monocytes contacted with a Nur77 agonist or contacted with a CX3CR1 agonist can have one or more of the foregoing functions or activities.

Compositions, methods and uses of the invention also include Nur77 agonists, as such agonists can promote, stimulate, enhance, or increase activity, function or expression of Nur77 polypeptide. Accordingly, Nur77 agonists can function as Nur77 polypeptide sequences, fragments/subsequences, polymorphisms, variants and modified forms, and as such be used in accordance with the invention compositions, methods and uses.

Non-limiting exemplary Nur77 agonists include 9-cis-retinoic acid; 1-di(3-indolyl)-1-(4-X-phenyl)methanes; etoposide; 5,8-diacetoxyl-6-(1'-acetoxy-4'-methyl-3'-pentenyl)-1,4-naphthaquinones; 12-O-tetradecanoylphorbol-13-acetate; diindolylmethane analogs (C-DIMs), such as 1,1-bis(3'-indolyl)-1-(p-methoxyphenyhmethane (DIM-C-pPhOCH3); 6-mercaptopurine; and panobinostat ((2E)-N-hydroxy-3-[4-({[2-(2-methyl-1H-indol-3-yl)ethyl]amino}methyl)phenyl]acrylamide). Additional Nur77 agonists include octaketide Cytosporone B (Csn-B) and derivatives thereof, such as n-amyl 2-[3,5-dihydroxy-2-(1-nonanoyl)phenyl]acetate or a compound having a structure set forth in Table 1.

TABLE 1

Structures of exemplary Csn-B derived Nur77 agonists (compounds 1-15)

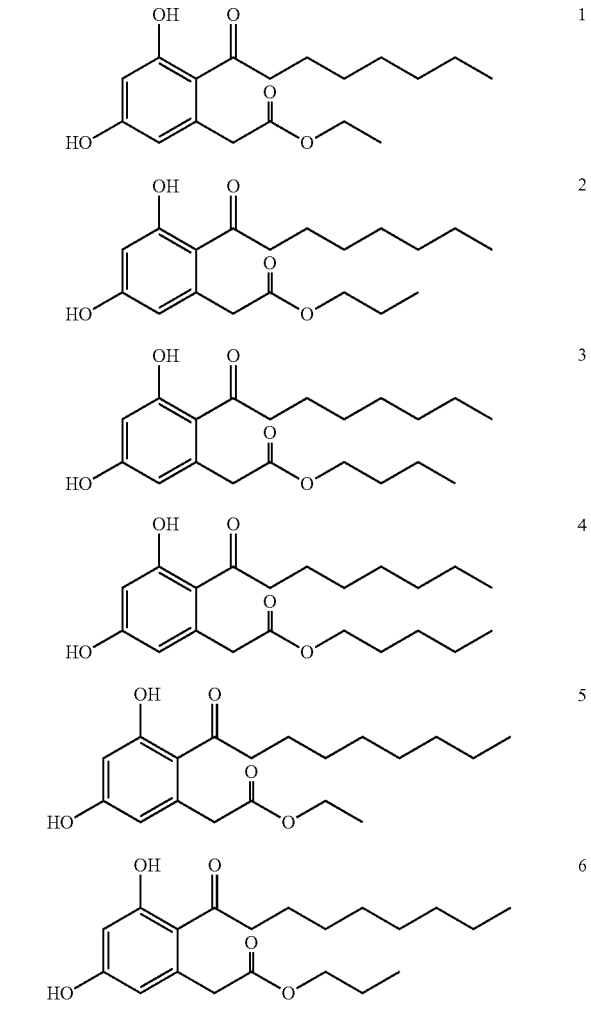

TABLE 1-continued

Structures of exemplary Csn-B derived Nur77 agonists (compounds 1-15)

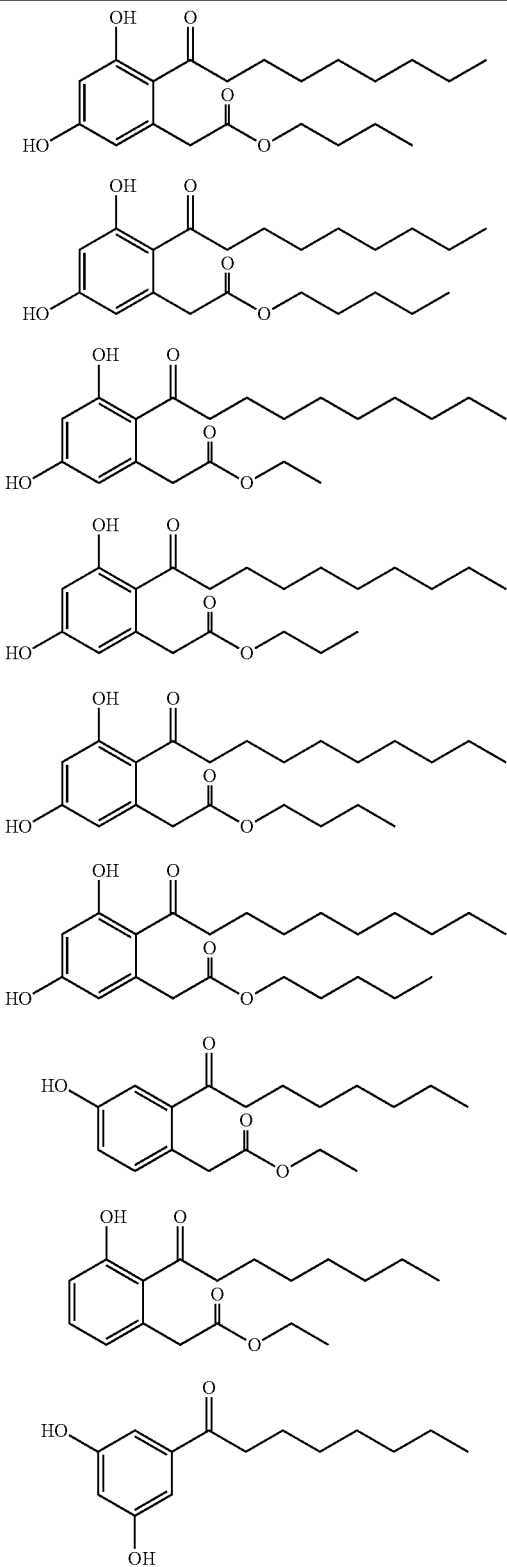

Compositions, methods and uses of the invention also include CX3CR1 agonists, as such agonists can promote, stimulate, enhance, or increase activity, function or expression of CX3CR1 polypeptide. Accordingly, CX3CR1 agonists can be used in accordance with the invention compositions, methods and uses.

Non-limiting exemplary CX3CR1 ligands (e.g., agonists) include CX3CL1 (also known as Fractalkine; Imai et al. 1997, Cell 91(4):521-30), Eotaxin-3/CC chemokine ligand 26 (CCL26; (Nakayama et al. 2010, J Immunol 185(11): 6472-9). Potential ligands include: CCL3, CCL4, RANTES, GRGDSP, and Linoleic Acid. Proteins such as vMIP-II encoded by Kaposi's sarcoma-associated herpesvirus (Kledal et al. 1997, Science 277(5332): 1656-9; Chen et al. 1998, J Exp Med 188(1):193-8) and the RSV G protein (Harcourt et al. 2006, J Immunol 176(3): 1600-8) bind to CX3CR1 and/or CX3CL1 and modulate their activity.

As used herein, the term "modify" and grammatical variations thereof, means that the composition deviates from a reference composition. Modifications include, for example, substitutions additions, insertions, deletions and other variations to the amino acid sequences set forth herein, which can be referred to as "variants." The invention compositions, methods and uses include such variant Nur77 polypeptides, including Nur77 polymorphisms.

Exemplary sequence substitutions, additions, and insertions include a full length or a portion of a sequence with one or more amino acids substituted, added or inserted. For example, a variant Nur77 polypeptide has one or more functions or activities of wild type Nur77, including without limitation one or more functions or activities of Nur77 as set forth herein. Such exemplary variant Nur77 polypeptide sequences include Nur77 polymorphisms. Exemplary Nur77 polymorphisms include one or more of the following amino acid substitutions, without limitation: (L) Leu to (V) Val at aa position 26; (D) Asp to (G) Gly at aa position 36; (T) Thr to (I) Ile at aa position 74; (S) Ser to (L) Leu at aa position 137; (G) Gly to (R) Arg at aa position 262; (G) Gly to (A) Ala at aa position 262; and (A) Ala to (D) Asp at aa position 400.

Additional non-limiting examples of variant polypeptides include, for example, non-conservative and conservative substitutions of Nur77 polypeptide sequences. In particular embodiments, a variant Nur77 protein has one or a few (e.g., 1-5%, 5-10%, 10-20% or 20-30% of the residues of total protein length, or 2-10, 10-20, 20-30, 30-40, 40-50, 50-60, 60-75, 75-100 residues, substituted) conservative or non-conservative substitutions.

As used herein, the term "conservative substitution" denotes the replacement of an amino acid residue by another, chemically or biologically similar residue. Biologically similar means that the substitution does not destroy a biological activity or function. Structurally similar means that the amino acids have side chains with similar length, such as alanine, glycine and serine, or a similar size. Chemical similarity means that the residues have the same charge or are both hydrophilic or hydrophobic. Particular examples of conservative substitutions include the substitution of a hydrophobic residue such as isoleucine, valine, leucine or methionine for another, the substitution of a polar residue for another, such as the substitution of arginine for lysine, glutamic for aspartic acids, or glutamine for asparagine, and the like. The term "conservative substitution" also includes the use of a substituted amino acid in place of an unsubstituted parent amino acid.

Modified proteins also include one or more D-amino acids substituted for L-amino acids (and mixtures thereof), structural and functional analogues, for example, peptidomimetics having synthetic or non-natural amino acids or amino acid analogues and derivatized forms. Modifications include cyclic structures such as an end-to-end amide bond between the amino and carboxy-terminus of the molecule or intra- or inter-molecular disulfide bond.

Modified forms further include "chemical derivatives," in which one or more amino acids have a side chain chemically altered or derivatized. Such derivatized polypeptides include, for example, amino acids in which free amino groups form amine hydrochlorides, p-toluene sulfonyl groups, carobenzoxy groups; the free carboxy groups form salts, methyl and ethyl esters: free hydroxl groups that form O-acyl or O-alkyl derivatives as well as naturally occurring amino acid derivatives, for example, 4-hydroxyproline, for proline, 5-hydroxylysine for lysine, homoserine for serine, ornithine for lysine etc. Also included are amino acid derivatives that can alter covalent bonding, for example, the disulfide linkage that forms between two cysteine residues that produces a cyclized polypeptide. Further modified forms include sugars, or glycosylated proteins.

As set forth herein, variant and modified forms include additions and insertions. For example, an addition can be one or more amino acid residues, or a covalent or non-covalent attachment of any type of molecule to a protein (e.g., Nur77) or other composition (e.g., Nur77 or CX3CR1 agonists). Particular examples of additions and insertions are entities that confer a complementary or a distinct function or activity.

Exemplary additions and insertions include fusion or chimeric polypeptide sequence constructs, which is a sequence having one or more molecules not normally present in a reference native (wild type) sequence (e.g., Nur77) covalently attached to the sequence. The terms "fusion" or "chimeric" and grammatical variations thereof, when used in reference to a molecule, such as a Nur77 or a Nur77 or CX3CR1 agonist, means that a portions or part of the molecule contains a different entity distinct from the molecule (e.g., Nur77 or CX3CR1 agonist) as they do not typically exist together in nature. That is, for example, one portion of the fusion or chimera includes or consists of a portion that does not exist together in nature, and is structurally distinct. A particular example is an amino acid sequence of another protein (e.g., immunoglobulin such as an Fc domain, or antibody) attached to Nur77 or Nur77 or CX3CR1 agonist to produce a fusion, or a chimeric polypeptide, to impart a distinct function (e.g., multifunctional, increased solubility, in vivo half-life, etc.).

Additions and insertions also include a label or a tag, which can be used to provide an agent that is detectable or that is useful for isolating the tagged entity (e.g., Nur77, Nur77 or CX3CR1 agonist). A detectable label can be attached, for example, to (e.g., linked conjugated) Nur77, or Nur77 or CX3CR1 agonist, or be within or be one or more atoms that comprise the molecule.

Non-limiting exemplary detectable labels include contrast agents (e.g., gadolinium; manganese; barium sulfate; an iodinated or noniodinated agent; an ionic agent or nonionic agent); magnetic and paramagnetic agents (e.g., iron-oxide chelate); nanoparticles; an enzyme (horseradish peroxidase, alkaline phosphatase, β-galactosidase, or acetylcholinesterase); a prosthetic group (e.g., streptavidin/biotin and avidin/biotin); a fluorescent material (e.g., umbelliferone, fluorescein, fluorescein isothiocyanate, rhodamine, dichlorotriazinylamine fluorescein, dansyl chloride or phycoerythrin); a luminescent material (e.g., luminol); or a bioluminescent material (e.g., luciferase, luciferin, aequorin).

Additional non-limiting examples of detectable labels and/or tags include enzymes (horseradish peroxidase, urease, catalase, alkaline phosphatase, beta-galactosidase, chloramphenicol transferase); enzyme substrates; ligands (e.g., biotin); receptors (avidin); GST-, T7-, His-, myc-, HA- and FLAG-tags; electron-dense reagents; energy transfer molecules; paramagnetic labels; fluorophores (fluorescein, fluorescamine, rhodamine, phycoerythrin, phycocyanin, allophycocyanin); chromophores; chemi-luminescent (imidazole, luciferase, acridinium, oxalate); and bio-luminescent agents.

As set forth herein, a tag or detectable label can be linked or conjugated (e.g., covalently) to the molecule (e.g., Nur77, Nur77 or CX3CR1 agonist). In various embodiments a detectable label, such as a radionuclide or metal or metal oxide can be bound or conjugated to the agent, either directly or indirectly. A linker or an intermediary functional group can be used to link the molecule to a detectable label or tag. Linkers include amino acid or peptidomimetic sequences inserted between the molecule and a label or tag so that the two entities maintain, at least in part, a distinct function or activity. Linkers may have one or more properties that include a flexible conformation, an inability to form an ordered secondary structure or a hydrophobic or charged character which could promote or interact with either domain. Amino acids typically found in flexible protein regions include Gly, Asn and Ser. The length of the linker sequence may vary without significantly affecting a function or activity.

Linkers further include chemical moieties, conjugating agents, and intermediary functional groups. Examples include moieties that react with free or semi-free amines, oxygen, sulfur, hydroxy or carboxy groups. Such functional groups therefore include mono and bifunctional cross-linkers, such as sulfo-succinimidyl derivatives (sulfo-SMCC, sulfo-SMPB), in particular, disuccinimidyl suberate (DSS), BS3 (Sulfo-DSS), disuccinimidyl glutarate (DSG) and disuccinimidyl tartrate (DST). Non-limiting examples include diethylenetriaminepentaacetic acid (DTPA) and ethylene diaminetetracetic acid.

Additional non-limiting examples of amino acid modifications and variants include protein subsequences and fragments. A subsequence, fragment or portion of Nur77 polypeptide means one or more amino acids fewer than the full length reference sequence, which is typically a native full length Nur77 polypeptide sequence. Deletion of one or more amino acids can result in a modification of the structure of the resultant polypeptide without significantly altering a biological function or activity. Exemplary subsequences and fragments therefore include a Nur77 polypeptide fragment or a portion thereof that promotes, stimulates, enhances, activates or increases in vitro and/or in vivo, monocyte migration to or mobilization against a tumor or cancer metastasis. Further non-limiting examples of such Nur77 polypeptide subsequences is to control, limit or decrease, in vitro and/or in vivo, metastasis of a tumor or cancer. Still further non-limiting examples of such Nur77 polypeptide subsequences is to control, limit, or decrease metastasis of a tumor or cancer from an original site to one or more other sites, in vitro and/or in vivo.

Non-limiting subsequences of full length Nur77 include amino acids having a length of about 10-20, 20-25, 25-50, 50-100, 100-150, 150-200, 200-250, 250-300, 300-350, 350-400, 400-500, 500-600 or more amino acids in length, but less than a full length Nur77 polypeptide sequence, e.g., a native (naturally occurring) sequence. As disclosed herein, Nur77 subsequences, fragments and portions can retain all or a part of a function or activity of full length Nur77 polypeptide.

Modified and variant Nur77 polypeptide sequences and subsequences of the invention may have an activity or function greater or less than 2-5, 5-10, 10-100, 100-1000 or 1000-10,000-fold activity or function than a comparison Nur77 polypeptide sequence or subsequence (e.g., SEQ ID NOs:1 or 2). For example, a modified Nur77 polypeptide sequences or subsequence could have an activity or function greater or less than 2-5, 5-10, 10-100, 100-1000 or 1000-10,000-fold activity or function of a reference Nur77 to promote, stimulate, enhance, activate or increase in vitro and/or in vivo, monocyte migration to or mobilization against a tumor or cancer metastasis; to control, limit or decrease, in vitro and/or in vivo, metastasis of a tumor or cancer; or to control, limit, or decrease metastasis of a tumor or cancer from an original site to one or more other sites, in vitro and/or in vivo.

Nur77 polypeptide variants also include sequences having less than 100% identity to a reference Nur77 polypeptide sequence. Such Nur77 polypeptide sequences can have at least about 60%, 65%, 70%, 75%, 80%, 85%, 90%, 95%, 96%, 97%, 98%, 99% or more identity (homology) to a reference Nur77 polypeptide sequence (e.g., a mammalian Nur77 polypeptide sequence, such as human Nur77 polypeptide sequence set forth as SEQ ID NOs:1 or 2). Such Nur77 polypeptide sequences with at least about 60%, 65%, 70%, 75%, 80%, 85%, 90%, 95%, 96%, 97%, 98%, 99% or more identity (homology) to a reference Nur77 sequence can have sufficient identity to retain all or a part of a function or activity of a reference Nur77 polypeptide.

The term "identity" and grammatical variations thereof, mean that two or more referenced entities are the same. Thus, where two polypeptide sequences (e.g., Nur77 polypeptide sequences) are identical, they have the same amino acid sequence, at least within the referenced region or portion. The identity can be over a defined area (region or domain) of the sequence. An "area of identity" refers to a portion of two or more referenced entities that are the same. Thus, where two protein sequences are identical over one or more sequence regions they share identity within that region.

The percent identity can extend over the entire sequence length of the polypeptide (e.g., a Nur77 polypeptide sequence). In particular aspects, the length of the sequence sharing the percent identity is 5 or more contiguous amino acids, e.g., 5, 6, 7, 8, 9, 10, 11, 12, 13, 14, 15, 16, 17, 18, 19, 20, 21, 22, 23, 24, 25, etc. contiguous amino acids. In additional particular aspects, the length of the sequence sharing the percent identity is 25 or more contiguous amino acids, e.g., 26, 27, 28, 29, 30, 31, 32, 33, 34, 35, etc. contiguous amino acids. In further particular aspects, the length of the sequence sharing the percent identity is 35 or more contiguous amino acids, e.g., 35, 36, 37, 38, 39, 40, 41, 42, 43, 44, 45, 45, 47, 48, 49, 50, etc., contiguous amino acids. In yet additional particular aspects, the length of the sequence sharing the percent identity is 50 or more contiguous amino acids, e.g., 50-55, 55-60, 60-65, 65-70, 70-75, 75-80, 80-85, 85-90, 90-95, 95-100, 100-110, etc. contiguous amino acids.

The extent of identity (homology) between two sequences can be ascertained using a computer program and mathematical algorithm known in the art. Such algorithms that calculate percent sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Modifications and variants can be produced using methods known in the art (e.g., PCR based site-directed, deletion and insertion mutagenesis, chemical modification and mutagenesis, cross-linking, etc.), or may be spontaneous or naturally occurring (e.g. random mutagenesis). For example, naturally occurring Nur77 polypeptide sequence allelic variants can occur by alternative RNA splicing, polymorphisms, or spontaneous mutations of a nucleic acid encoding Nur77 polypeptide. Additions and deletions of one or more amino acids can also be produced using molecular genetic techniques known to the skill artisan.

Invention compositions, methods and uses include isolated and purified Nur77 polypeptides, variants and modified forms, such as subsequences and fragments and polymorphisms of Nur77 polypeptides, Nur77 agonists, CX3CR1 agonists, Nur77 regulated monocytes (e.g., $CD14^+$ $CD16^+$ or $CD14^{dim}CD16^+$ ($CD115^+CD11b^+GR1^-$ (Ly6C−)) monocytes, or $CD14^+$ $CD16^+$ monocytes or $CD14^{dim}CD16^+$ ($CD115^+CD11b^+GR1^-$ (Ly6C−)) monocytes contacted with a Nur77 agonist or contacted with a CX3CR1 agonist. The term "isolated," when used as a modifier of a composition, means that the composition is made by the hand of man or are separated, completely or at least in part, from their naturally occurring in vivo environment. The term "isolated" does not exclude alternative physical forms of the composition, such as fusions/chimeras, multimers/oligomers, modifications (e.g., phosphorylation, glycosylation, lipidation) or derivatized forms, or forms expressed in host cells produced by the hand of man.

An "isolated" composition (e.g., Nur77 polypeptides, subsequences, Nur77 agonists, CX3CR1 agonists, Nur77 regulated monocytes (e.g., $CD14^+$ $CD16^+$ or $CD14^{dim}CD16^+$ ($CD115^+CD11b^+GR1^-$ (Ly6C−)) monocytes, or $CD14^+$ $CD16^+$ monocytes or $CD14^{dim}CD16^+$ ($CD115^+CD11b^+GR1^-$ (Ly6C−)) monocytes contacted with a Nur77 agonist or contacted with a CX3CR1 agonist) can also be "substantially pure" or "purified" when free of most or all of the materials with which it typically associates with in nature. Generally, isolated compositions are substantially free of one or more materials with which they normally associate with in nature, for example, one or more protein, nucleic acid, lipid, carbohydrate, cell membrane. Thus, an isolated sequence that also is substantially pure or purified does not include polypeptides or polynucleotides present among millions of other sequences, such as antibodies of an antibody library or nucleic acids in a genomic or cDNA library, for example. Typically, purity can be at least about 50%, 60% or more by mass. The purity can also be about 70% or 80% or more, and can be greater, for example, 90% or more. Purity can be determined by any appropriate method, including, for example, UV spectroscopy, chromatography (e.g., HPLC, gas phase), gel electrophoresis and sequence analysis (nucleic acid and peptide), and is typically relative to the amount of impurities, which typically does not include inert substances, such as water.

A "substantially pure" or "purified" composition can be combined with one or more other molecules. Thus, "substantially pure" or "purified" does not exclude combinations of compositions, such as combinations of Nur77 polypeptide sequences, subsequences, variants/modified forms (e.g., polymorphisms), or Nur77 or CX3CR1 agonists. For example, a composition can include a combination of Nur77 polypeptide, and/or a Nur77 or CX3CR1 agonist, and/or an anti-cell proliferative, anti-tumor or anti-cancer drug or agent.

As used herein, the term "recombinant," when used as a modifier of polypeptides, means that the compositions have been manipulated (i.e., engineered) in a fashion that generally does not occur in nature (e.g., in vitro). A particular example of a recombinant polypeptide would be where a Nur77 polypeptide is expressed by a cell transfected with a polynucleotide encoding the Nur77 polypeptide. Another example of a recombinant polypeptide is a hybrid or fusion sequence, such as a chimeric or fusion Nur77 polypeptide sequence comprising and a second sequence, such as a heterologous functional domain (e.g., an immunoglobulin sequence, such as an Fc domain).

Invention compositions, methods and uses that include Nur77 polypeptides and subsequences, Nur77 agonists, CX3CR1 agonists, Nur77 regulated monocytes (e.g., CD14$^+$ CD16$^+$ or CD14$^{dim}$CD16$^+$ (CD115$^+$CD11b$^+$GR1$^-$ (Ly6C–)) monocytes, or CD14$^+$ CD16$^+$ monocytes or CD14$^{dim}$CD16$^+$ (CD115$^+$CD11b$^+$GR1$^-$ (Ly6C–)) monocytes contacted with a Nur77 agonist or contacted with a CX3CR1 agonist can include any amount or dose of Nur77 polypeptides and subsequences, Nur77 agonists, CX3CR1 agonists, Nur77 regulated monocytes (e.g., CD14$^+$ CD16$^+$ or CD14$^{dim}$CD16$^+$ (CD115$^+$CD11b$^+$GR1$^-$ (Ly6C–)) monocytes, or CD14$^+$ CD16$^+$ monocytes or CD14$^{dim}$CD16$^+$ (CD115$^+$CD11b$^+$GR1$^-$ (Ly6C–)) monocytes contacted with a Nur77 agonist or contacted with a CX3CR1 agonist. In particular embodiments, such Nur77 polypeptides, Nur77 subsequences, Nur77 agonists, CX3CR1 agonists, is in a concentration range of about 1 µg/ml to 1 mg/ml, or in a range of about 10 µg/ml to 100 mg/ml, or in a range of about 100 µg/ml to 1,000 mg/ml, or at a concentration of about 0.1 mg/ml, 1 mg/ml or 10 mg/ml. In further particular embodiments, Nur77 is in an amount of 10-1,000 milligrams, or an amount of 10-100 milligrams.

In particular embodiments, doses of Nur77 regulated monocytes (e.g., CD14$^+$ CD16$^+$ or CD14$^{dim}$CD16$^+$ (CD115$^+$CD11b$^+$GR1$^-$ (Ly6C–)) monocytes, or CD14$^+$ CD16$^+$ monocytes or CD14$^{dim}$CD16$^+$ (CD115$^+$CD11b$^+$ GR1$^-$ (Ly6C–)) monocytes contacted with a Nur77 agonist or contacted with a CX3CR1 agonist that can be delivered for therapy range from about 0.5 to 2.5×10^8 monocytes. Such doses can be based, for example, on the number of monocyte cells found in normal circulation.

Nur77 polypeptides, subsequences, variants and modified forms (e.g., modified or unmodified full length native mammalian, such as human Nur77 polypeptide sequences), Nur77 agonists, CX3CR1 agonists, Nur77 regulated monocytes (e.g., CD14$^+$ CD16$^+$ or CD14$^{dim}$CD16$^+$ (CD115$^+$CD11b$^+$GR1$^-$ (Ly6C–)) monocytes, or CD14$^+$ CD16$^+$ monocytes or CD14$^{dim}$CD16$^+$ (CD115$^+$CD11b$^+$GR1$^-$ (Ly6C–)) monocytes contacted with a Nur77 agonist or contacted with a CX3CR1 agonist are useful in various treatment methods and uses. Such Nur77 polypeptides and subsequences, Nur77 agonists, CX3CR1 agonists, Nur77 regulated monocytes (e.g., CD14$^+$ CD16$^+$ or CD14$^{dim}$CD16$^+$ (CD115$^+$CD11b$^+$GR1$^-$ (Ly6C–)) monocytes, or CD14$^+$ CD16$^+$ monocytes or CD14$^{dim}$CD16$^+$ (CD115$^+$CD11b$^+$GR1$^-$ (Ly6C–)) monocytes contacted with a Nur77 agonist or contacted with a CX3CR1 agonist and compositions thereof are applicable to uses and treatment methods for numerous disorders and diseases, both chronic and acute.

Methods and uses in accordance with the invention include, but are not limited to increasing numbers of monocytes to a tumor or cancer metastasis site in a subject. Methods and uses in accordance with the invention also include, but are not limited to increasing, stimulating, activating or promoting monocyte migration to or mobilization against a tumor or cancer metastasis in a subject. Methods and uses in accordance with the invention further include, but are not limited to, controlling, limiting, or decreasing metastasis of a tumor or cancer in a subject. Methods and uses in accordance with the invention additionally include, but are not limited to, controlling, limiting, or decreasing metastasis of a tumor or cancer from an original site to one or more other sites in a subject. Methods and uses in accordance with the invention still further include, but are not limited to, controlling, limiting, or decreasing metastasis of a tumor or cancer in a subject. Methods and uses in accordance with the invention moreover include, but are not limited to, controlling, limiting, or decreasing metastasis of a tumor or cancer from an original site to one or more other sites in a subject.

In accordance with the invention, there are provided compositions, methods and uses for treating acute and chronic responses, disorders and diseases in which a subject would benefit from (e.g., is in need of treatment with) any of Nur77 polypeptides or subsequences, Nur77 agonists, CX3CR1 agonists, Nur77 regulated monocytes (e.g., CD14$^+$ CD16$^+$ or CD14$^{dim}$CD16$^+$ (CD115$^+$CD11b$^+$GR1$^-$ (Ly6C–)) monocytes, or CD14$^+$ CD16$^+$ monocytes or CD14$^{dim}$CD16$^+$ (CD115$^+$CD11b$^+$GR1$^-$ (Ly6C–)) monocytes contacted with a Nur77 agonist or contacted with a CX3CR1 agonist In various non-limiting embodiments of such methods and uses, a Nur77 polypeptide and/or subsequence, Nur77 agonist, CX3CR1 agonist, Nur77 regulated monocyte (e.g., CD14$^+$ CD16$^+$ or CD14$^{dim}$CD16$^+$ (CD115$^+$CD11b$^+$GR1$^-$ (Ly6C–)) monocytes, or CD14$^+$ CD16$^+$ monocytes or CD14$^{dim}$CD16$^+$ (CD115$^+$CD11b$^+$GR1$^-$ (Ly6C–)) monocytes contacted with a Nur77 agonist or contacted with a CX3CR1 agonist is administered to a subject in an amount intended to achieve a desired effect.

Methods and uses of the invention include uses and administering to or contact of a subject with Nur77 regulated monocytes (e.g., CD14$^+$ CD16$^+$ or CD14$^{dim}$CD16$^+$ (CD115$^+$CD11b$^+$GR1$^-$ (Ly6C–)) monocytes, or CD14$^+$ CD16$^+$ monocytes or CD14$^{dim}$CD16$^+$ (CD115$^+$CD11b$^+$ GR1$^-$ (Ly6C–)) monocytes contacted with a Nur77 agonist or contacted with a CX3CR1 agonist (cell based therapy). Accordingly, methods of the invention include administration to a subject and uses of Nur77 regulated monocytes (e.g., CD14$^+$ CD16$^+$ or CD14$^{dim}$CD16$^+$ (CD115$^+$CD11b$^+$ GR1$^-$ (Ly6C–)) monocytes, or CD14$^+$ CD16$^+$ monocytes or CD14$^{dim}$CD16$^+$ (CD115$^+$CD11b$^+$GR1$^-$ (Ly6C–)) monocytes contacted with a Nur77 agonist or contacted with a CX3CR1 agonist in order to achieve a desired result in a subject or to effect treatment of a subject. Such cells (monocytes) can be administered or delivered or used, for example, to decrease, reduce, inhibit, suppress, limit or control metastasis of a tumor or cancer.

In various embodiments of the invention, a method results in increasing the amount Nur77 polypeptide sequence in the subject, thereby effecting treatment of the subject in accordance with the invention uses and methods. An increase in Nur77 can be achieved by introduction of Nur77 or a nucleic acid encoding Nur77, or an agonist of Nur77 that increases or stimulates expression of Nur77 (e.g., endogenous Nur77 expression). Accordingly, methods and uses of the invention include administration of Nur77 or a nucleic acid encoding Nur77, or an agonist of Nur77 that increases or stimulates expression of Nur77. Amounts desired may vary depending upon the subject, the desired effect, and the disorder or disease, or risk of disorder or disease, to be treated.

The term "contacting" means direct or indirect binding or interaction between two or more entities (e.g., between a Nur77 polypeptide sequence or Nur77 or CX3CR1 agonist and a target). A particular example of direct interaction is binding (e.g., Nur77 agonist binding to Nur77 polypeptide target or CX3CR1 agonist binding to CX3CR1 target). A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration, or delivery.

In methods and uses of the invention, Nur77 polypeptides and subsequences, Nur77 agonists, CX3CR1 agonists, Nur77 regulated monocytes (e.g., $CD14^+$ $CD16^+$ or $CD14^{dim}CD16^+$ ($CD115^+CD11b^+GR1^-$ (Ly6C−)) monocytes, or $CD14^+$ $CD16^+$ monocytes or $CD14^{dim}CD16^+$ ($CD115^+CD11b^+GR1^-$ (Ly6C−)) monocytes contacted with a Nur77 agonist or contacted with a CX3CR1 agonist or a composition thereof can be administered prior to, substantially contemporaneously with or following establishment of a tumor or cancer, prior to or after tumor or cancer metastasis. Thus, methods and uses of the invention may be practiced prior to (i.e. prophylaxis), concurrently with or after evidence of the tumor or cancer, or metastasis of a tumor or cancer.

Administering Nur77 polypeptides and subsequences, Nur77 agonists, CX3CR1 agonists, Nur77 regulated monocytes (e.g., $CD14^+$ CD16+ or $CD14^{dim}CD16^+$ ($CD115^+CD11b^+GR1^-$ (Ly6C−)) monocytes, or $CD14^+$ $CD16^+$ monocytes or $CD14^{dim}CD16^+$ ($CD115^+CD11b^+GR1^-$ (Ly6C−)) monocytes contacted with a Nur77 agonist or contacted with a CX3CR1 agonist, or a composition thereof prior to, concurrently with or immediately following tumor or cancer establishment, or prior to, concurrently with or immediately following metastasis to one or more other sites, e.g., organs or tissues.

The invention provides combinations of Nur77 polypeptides and subsequences, Nur77 agonists, CX3CR1 agonists, Nur77 regulated monocytes (e.g., $CD14^+$ $CD16^+$ or $CD14^{dim}CD16^+$ ($CD115^+CD11b^+GR1^-$ (Ly6C−)) monocytes, or $CD14^+$ $CD16^+$ monocytes or $CD14^{dim}CD16^+$ ($CD115^+CD11b^+GR1^-$ (Ly6C−)) monocytes contacted with a Nur77 agonist or contacted with a CX3CR1 agonist, and a second agent or drug, and methods and uses of such combinations. In one embodiment, a composition includes a Nur77 polypeptide and/or subsequence, and/or Nur77 agonist, and/or CX3CR1 agonist, and/or Nur77 regulated monocytes (e.g., $CD14^+$ $CD16^+$ or $CD14^{dim}CD16^+$ ($CD115^+CD11b^+GR1^-$ (Ly6C−)) monocytes, and/or $CD14^+$ $CD16^+$ monocytes and/or $CD14^{dim}CD16^+$ ($CD115^+CD11b^+GR1^-$ (Ly6C−)) monocytes contacted with a Nur77 agonist and/or contacted with a CX3CR1 agonist, and an anti-cell proliferative, anti-tumor or anti-cancer agent, drug or treatment. Nur77 polypeptides and subsequences, Nur77 agonists, CX3CR1 agonists, Nur77 regulated monocytes (e.g., $CD14^+$ $CD16^+$ or $CD14^{dim}CD16^+$ ($CD115^+CD11b^+GR1^-$ (Ly6C−)) monocytes, or $CD14^+$ $CD16^+$ monocytes or $CD14^{dim}CD16^+$ ($CD115^+CD11b^+GR1^-$ (Ly6C−)) monocytes contacted with a Nur77 agonist or contacted with a CX3CR1 agonist or a composition thereof can be administered in combination with a second agent, drug or treatment. According to the invention, Nur77 polypeptides and/or subsequences, Nur77 agonists, CX3CR1 agonists, Nur77 regulated monocytes (e.g., $CD14^+$ $CD16^+$ or $CD14^{dim}CD16^+$ ($CD115^+CD11b^+GR1^-$ (Ly6C−)) monocytes, or $CD14^+$ $CD16^+$ monocytes or $CD14^{dim}CD16^+$ ($CD115^+CD11b^+GR1^-$ (Ly6C−)) monocytes contacted with a Nur77 agonist or contacted with a CX3CR1 agonist, or a composition thereof, can be administered prior to, substantially contemporaneously with or following administering a second agent, drug or treatment, such as an anti-cell proliferative, anti-tumor, anti-cancer or, immune enhancing/stimulating agent, drug or treatment.

Non-limiting examples of agents, drugs or treatments include surgical resection, chemotherapy, immunotherapy, radiotherapy, ionizing or chemical radiation therapy, chemotherapy, immunotherapy, local or regional thermal (hyperthermia) therapy, or vaccination. Such treatments or therapies can be administered prior to, substantially contemporaneously with (separately or in a mixture), or following administration of a Nur77 polypeptide and/or subsequence, and/or Nur77 agonist, and/or CX3CR1 agonist, and/or Nur77 regulated monocytes (e.g., $CD14^+$ $CD16^+$ or $CD14^{dim}CD16^+$ ($CD115^+CD11b^+GR1^-$ (Ly6C−)) monocytes, and/or $CD14^+$ $CD16^+$ monocytes and/or $CD14^{dim}CD16^+$ (CD115+$CD11b^+GR1^-$ (Ly6C−)) monocytes contacted with a Nur77 agonist and/or contacted with a CX3CR1 agonist.

Accordingly, invention methods and uses include administering an anti-cell proliferative, anti-neoplastic, anti-tumor, anti-cancer or immune-enhancing treatment or therapy. In particular embodiments, a method or use includes administering an alkylating agent, anti-metabolite, plant extract, plant alkaloid, nitrosourea, hormone, nucleoside or nucleotide analog; cyclophosphamide, azathioprine, cyclosporin A, prednisolone, melphalan, chlorambucil, mechlorethamine, busulphan, methotrexate, 6-mercaptopurine, thioguanine, 5-fluorouracil, cytosine arabinoside, 5-azacytidine (5-AZC) and 5-azacytidine related compounds, bleomycin, actinomycin D, mithramycin, mitomycin C, carmustine, lomustine, semustine, streptozotocin, hydroxyurea, cisplatin, carboplatin, oxiplatin, mitotane, procarbazine, dacarbazine, a taxane (e.g., taxol or paclitaxel), vinblastine, vincristine, doxorubicin or dibromomannitol, topoisomerase inhibitors, (irinotecan, topotecan, etoposide, teniposide), gemcitabine, pemetrexed etc. Cell or immunotherapies include lymphocytes, plasma cells, macrophages, dendritic cells, T-cells, NK cells or B-cells; an antibody, a cell growth factor, a cell survival factor, a cell differentiative factor, a cytokine or a chemokine.

Additional agents that are applicable in compositions, methods or uses of the invention include targeted biologicals or drugs, such as antibodies (monoclonal) or small molecules. Non-limiting examples of monoclonal antibodies include rituximab (Rituxan®), trastuzumab (Herceptin®), pertuzumab (Perjeta®)), bevacizumab (Avastin®), ranibizumab (Lucentis®), cetuximab (Erbitux®), alemtuzumab (Campath®), panitumumab (Vectibix®), ibritumomab tiuxetan (Zevalin®), tositumomab (Bexxar®), ipilimumab, zalutumumab, dalotuzumab, figitumumab, ramucirumab, galiximab, farletuzumab, ocrelizumab, ofatumumab (Arzerra®), tositumumab, ibritumomab, 2F2 (HuMax-CD20), 7D8, IgM2C6, IgG1 2C6, 11B8, B1, 2H7, LT20. 1F5 or AT80 daclizumab (Zenapax®) which can be used in combination with a Nur77 polypeptide and/or subsequence, and/or Nur77 agonist, and/or CX3CR1 agonist, and/or Nur77 regulated monocytes (e.g., CD14$^+$ CD16$^+$ or CD14$^{dim}$ CD16$^+$ (CD115$^+$CD11b$^+$GR1$^-$ (Ly6C–)) monocytes, and/or CD14$^+$ CD16$^+$ monocytes and/or CD14$^{dim}$CD16$^+$ (CD115$^+$CD11b$^+$GR1$^-$ (Ly6C–)) monocytes contacted with a Nur77 agonist and/or contacted with a CX3CR1 agonist.

Other targeted drugs that are applicable for use with a Nur77 polypeptide and/or subsequence, and/or Nur77 agonist, and/or CX3CR1 agonist, and/or Nur77 regulated monocytes (e.g., CD14$^+$ CD16$^+$ or CD14$^{dim}$CD16$^+$ (CD115$^+$CD11b$^+$GR1$^-$ (Ly6C–)) monocytes, and/or CD14$^+$ CD16$^+$ monocytes and/or CD14$^{dim}$CD16$^+$ (CD115$^+$CD11b$^+$GR1$^-$ (Ly6C–)) monocytes contacted with a Nur77 agonist and/or contacted with a CX3CR1 agonist are kinase inhibitors e.g., imatinib (Gleevec®), gefitinib (Iressa®), bortzomib (Velcade®), lapatinib (Tykerb®), sunitinib (Sutent®), sorafenib (Nevaxar®), nilotinib (Tasigna®) etc. Non-limiting examples of cell growth factors, cell survival factors, cell differentiative factors, cytokines and chemokines include IL-2, IL-1α, IL-1β, IL-3, IL-6, IL-7, granulocyte-macrophage-colony stimulating factor (GMCSF), IFN-γ, IL-12, TNF-α, TNFβ, MIP-1α, MIP-1β, RANTES, SDF-1, MCP-1, MCP-2, MCP-3, MCP-4, eotaxin, eotaxin-2, I-309/TCA3, ATAC, HCC-1, HCC-2, HCC-3, LARC/MIP-3α, PARC, TARC, CKβ, CKβ6, CKβ7, CKβ8, CKβ9, CKβ11, CKβ12, C10, IL-8, GROα, GROβ, ENA-78, GCP-2, PBP/CTAPIIIβ-TG/NAP-2, Mig, PBSF/SDF-1 and lymphotactin.

Accordingly, the invention includes combinations of a Nur77 polypeptide and/or subsequence, and/or Nur77 agonist, and/or CX3CR1 agonist, and/or Nur77 regulated monocytes (e.g., CD14$^+$ CD16$^+$ or CD14$^{dim}$CD16$^+$ (CD115$^+$CD11b$^+$GR1$^-$ (Ly6C–)) monocytes, and/or CD14$^+$ CD16$^+$ monocytes and/or CD14$^{dim}$CD16$^+$ (CD115$^+$CD11b$^+$GR1$^-$ (Ly6C–)) monocytes contacted with a Nur77 agonist and/or contacted with a CX3CR1 agonist with other agents, drugs and treatments, and methods and uses of such combinations. The invention also provides methods and uses of such a Nur77 polypeptide and/or subsequence, and/or Nur77 agonist, and/or CX3CR1 agonist, and/or Nur77 regulated monocytes (e.g., CD14$^+$ CD16$^+$ or CD14$^{dim}$CD16$^+$ (CD115$^+$CD11b$^+$GR1$^-$ (Ly6C–)) monocytes, and/or CD14$^+$ CD16$^+$ monocytes and/or CD14$^{dim}$CD16$^+$ (CD115$^+$CD11b$^+$GR1$^-$ (Ly6C–)) monocytes contacted with a Nur77 agonist and/or contacted with a CX3CR1 agonist which are administered prior to, substantially contemporaneously with or following administering a second agent, drug or treatment.

As used herein, the terms "neoplasia" and "tumor" refer to a cell or population of cells whose growth, proliferation or survival is greater than growth, proliferation or survival of a normal counterpart cell, e.g. a cell proliferative or differentiative disorder. A tumor is a neoplasia that has formed a distinct mass or growth. A "cancer" or "malignancy" refers to a neoplasia or tumor that can invade adjacent spaces, tissues or organs. A "metastasis" refers to a neoplasia, tumor or cancer that has disseminated or spread from its primary site to one or more secondary sites, distinct or distal sites, locations or regions within the subject, in which the sites, locations or regions are distinct from the primary tumor or cancer.

Neoplasia, tumor, cancer and malignancy treatable in accordance with the invention include metastatic, and non-metastatic or benign forms. Non-limiting examples include a solid cellular mass, hematopoietic cells, or a carcinoma, sarcoma (e.g. lymphosarcoma, liposarcoma, osteosarcoma, chondrosarcoma, leiomyosarcoma, rhabdomyosarcoma or fibrosarcoma), lymphoma, leukemia, adenoma, adenocarcinoma, melanoma, glioma, glioblastoma, meningioma, neuroblastoma, retinoblastoma, astrocytoma, oligodendrocytoma, mesothelioma, reticuloendothelial, lymphatic or haematopoietic (e.g., myeloma, lymphoma or leukemia) neoplasia, tumor, cancer or malignancy.

Neoplastic, tumor, and cancer cells (metastatic or non-metastatic) include dormant or residual neoplastic, tumor, and cancer cells. Such cells typically consist of remnant tumor cells that are not dividing (G0-G1 arrest). These cells can persist in a primary site or as disseminated neoplastic, tumor, or cancer cells as a minimal residual disease. These dormant neoplastic, tumor, or cancer cells remain asymptomatic, but can develop severe symptoms and death once these dormant cells proliferate. Invention methods and uses can be used to reduce or inhibit proliferation of dormant neoplastic, tumor, or cancer cells, which can in turn inhibit or reduce tumor or cancer relapse, or tumor or cancer metastasis or progression.

The metastatic or non-metastatic tumor, cancer, or neoplasia may be in any stage, e.g., early or advanced, such as a stage I, II, III, IV or V tumor. The metastatic or non-metastatic tumor, cancer, or neoplasia may have been subject to a prior treatment or be stabilized (non-progressing) or in remission.

In terms of metastasis, invention methods and uses can be used to reduce or inhibit metastasis of a primary tumor or cancer to other sites, or the formation or establishment of metastatic tumors or cancers at other sites, locations or regions distinct and/or distal from the primary tumor or cancer thereby inhibiting or reducing tumor or cancer relapse or tumor or cancer progression. Thus, methods of the invention include, among other things, 1) reducing or inhibiting growth, proliferation, mobility or invasiveness of tumor or cancer cells that potentially or do develop metastases (e.g., disseminated tumor cells, DTC); 2) reducing or inhibiting formation or establishment of metastases arising from a primary tumor or cancer to one or more other sites, locations or regions distinct from the primary tumor or cancer; 3) reducing or inhibiting growth or proliferation of a metastasis at one or more other sites, locations or regions distinct from the primary tumor or cancer after a metastasis has formed or has been established; and 4) reducing or inhibiting formation or establishment of additional metastasis after the metastasis has been formed or established.

Cells of a metastatic or non-metastatic tumor, cancer, malignancy or neoplasia may be aggregated in a "solid" cell mass or be dispersed or diffused. A "solid" tumor refers to cancer, neoplasia or metastasis that typically aggregates together and forms a mass.

Neoplasia, tumor, cancer and malignancy treatable can be present in or affect a lung (small cell lung or non-small cell lung cancer), thyroid, head or neck, nasopharynx, throat, nose or sinuses, brain, spine, adrenal gland, pituitary gland, breast, ovarian, uterine, cervical, gastrointestinal (mouth, esophagus, stomach, duodenum, ileum, jejunum (small intestine), colon, rectum), lung, genito-urinary tract (uterus, ovary, cervix, endometrial, bladder, testicle, penis, prostate), glial, hematologic, endometrial, lymph, blood, muscle, dermal (e.g., melanocytes) or skin cell, kidney, pancreas, liver, bone, bone marrow, Wilm's tumors, biliary tract, B-ALL (B-cell lymphoblastic leukemia), stem cell, or hematologic neoplasia, tumor, cancer, or malignancy. Specific non-limiting examples include lung, breast, ovarian, uterine, cervical, stomach, gastric, colon, bladder, glial, dermal (e.g., melanocytes) and endometrial tumors/cancers.

Carcinomas, which refer to malignancies of epithelial or endocrine tissue, include respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from the uterus, cervix, lung, prostate, breast, head and neck, colon, pancreas, testes, adrenal, kidney, esophagus, stomach, liver and ovary. The term also includes carcinosarcomas, e.g., which include malignant tumors composed of carcinomatous and sarcomatous tissues.

Adenocarcinoma includes a carcinoma of a glandular tissue, or in which the tumor forms a gland like structure.

Sarcomas refer to malignant tumors of mesenchymal cell origin. Exemplary sarcomas include for example, lymphosarcoma, liposarcoma, osteosarcoma, chondrosarcoma, leiomyosarcoma, rhabdomyosarcoma and fibrosarcoma.

Neural neoplasias include glioma, glioblastoma, meningioma, neuroblastoma, retinoblastoma, astrocytoma and oligodendrocytoma.

A "liquid tumor," which refers to neoplasia that is dispersed or is diffuse in nature, as they do not typically form a solid mass. Particular examples include neoplasia of the reticuloendothelial or hematopoietic system, such as lymphomas, myelomas and leukemias. Non-limiting examples of leukemias include acute and chronic lymphoblastic, myeloblastic and multiple myeloma. Typically, such diseases arise from poorly differentiated acute leukemias, e.g., erythroblastic leukemia and acute megakaryoblastic leukemia. Specific myeloid disorders include, but are not limited to, acute promyeloid leukemia (APML), acute myelogenous leukemia (AML) and chronic myelogenous leukemia (CML). Lymphoid malignancies include, but are not limited to, acute lymphoblastic leukemia (ALL), which includes B-lineage ALL (B-ALL) and T-lineage ALL (T-ALL), chronic lymphocytic leukemia (CLL), prolymphocytic leukemia (PLL), hairy cell leukemia (HLL) and Waldenstroem's macroglobulinemia (WM). Specific malignant lymphomas include, non-Hodgkin lymphoma and variants, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Invention compositions, methods and uses, such as treatment methods and uses, can provide a detectable or measurable therapeutic benefit or improvement to a subject. A therapeutic benefit or improvement is any measurable or detectable, objective or subjective, transient, temporary, or longer-term benefit to the subject or improvement in the response, disorder or disease, or one or more adverse symptoms, disorders, illnesses, pathologies, diseases, or complications. In particular embodiments, a method of treatment results in partial or complete destruction of the neoplastic, tumor, cancer or metastatic cell mass, volume, size or numbers of cells; stimulating, inducing or increasing neoplastic, tumor, cancer or metastasis cell necrosis, lysis or apoptosis; reducing neoplasia, tumor, cancer or metastasis volume size, cell mass; inhibiting or preventing establishment, progression or an increase in neoplasia, tumor, cancer or metastasis volume, mass, size or cell numbers; or prolonging lifespan.

Compositions, methods and uses of the invention, in which a therapeutic benefit or improvement is a desired outcome, a composition such as a Nur77 polypeptide and/or subsequence, and/or Nur77 agonist, and/or CX3CR1 agonist, and/or Nur77 regulated monocytes (e.g., $CD14^+$ $CD16^+$ or $CD14^{dim}CD16^+$ ($CD115^+CD11b^+GR1^-$ (Ly6C-)) monocytes, and/or $CD14^+$ $CD16^+$ monocytes and/or $CD14^{dim}CD16^+$ ($CD115^+CD11b^+GR1^-$ (Ly6C-)) monocytes contacted with a Nur77 agonist and/or contacted with a CX3CR1 agonist, can be administered in a sufficient or effective amount to a subject in need thereof. An "effective amount" or "sufficient amount" refers to an amount that provides, in single or multiple doses, alone or in combination, with one or more other compositions (therapeutic agents such as a drug), treatments, protocols, or therapeutic regimens agents, a detectable response of any duration of time (long or short term), an expected or desired outcome in or a benefit to a subject of any measurable or detectable degree or for any duration of time (e.g., for minutes, hours, days, months, years, or cured).

Accordingly, methods and uses of the invention, such as treatment methods and uses, can provide a detectable or measurable therapeutic benefit or improvement to a subject. A therapeutic benefit or improvement is any measurable or detectable, objective or subjective, transient, temporary, or longer-term benefit to the subject or improvement in the condition, disorder or disease, an adverse symptom, consequence or underlying cause, of any degree, in a tissue, organ, cell or cell population of the subject.

Therapeutic benefits and improvements include, but are not limited to, reducing or decreasing occurrence, frequency, severity, progression, or duration of one or more symptoms or complications associated with a disorder, disease or condition, or an underlying cause or consequential effect of the disorder, disease or condition. For example, a sufficient amount of a Nur77 polypeptide and/or subsequence, and/or Nur77 agonist, and/or CX3CR1 agonist, and/or Nur77 regulated monocytes (e.g., $CD14^+$ $CD16^+$ or $CD14^{dim}CD16^+$ ($CD115^+CD11b^+GR1^-$ (Ly6C-)) monocytes, and/or $CD14^+$ $CD16^+$ monocytes and/or $CD14^{dim}CD16^+$ ($CD115^+CD11b^+GR1^-$ (Ly6C-)) monocytes contacted with a Nur77 agonist and/or contacted with a CX3CR1 agonist, or a composition thereof, is considered as having a therapeutic effect if administration results in a decreased, reduced, inhibited, controls or limits tumor or cancer metastasis.)

An "amount sufficient" or "amount effective" refers to an amount that is anticipated to provide, in single or multiple doses, alone or in combination, with one or more other compositions (therapeutic agents such as a chemotherapeutic or immune stimulating drug), treatments, protocols, or therapeutic regimens agents, a detectable response of any duration of time (long or short term), a desired outcome in or a benefit to a subject of any measurable or detectable degree or for any duration of time (e.g., for hours, days, months, years, or cured). The doses or "sufficient amount" or "effective amount" for treatment (e.g., to provide a therapeutic benefit or improvement) typically are effective to ameliorate a disorder, disease or condition, or one, multiple or all adverse symptoms, consequences or complications of the disorder, disease or condition, to a measurable extent, although reducing or inhibiting a progression or worsening of the disorder, disease or condition or a symptom, is considered a satisfactory outcome.

The term "ameliorate" means a detectable objective or subjective improvement in a subject's condition. A detectable improvement includes a subjective or objective reduction in the occurrence, frequency, severity, progression, or duration of a symptom caused by or associated with a disorder, disease or condition, an improvement in an underlying cause or a consequence of the disorder, disease or condition, or a reversal of the disorder, disease or condition.

Treatments or uses can therefore result in inhibiting, reducing or preventing a disorder, disease or condition, or an associated symptom or consequence, or underlying cause; inhibiting, reducing or preventing a progression or worsening of a disorder, disease, condition, symptom or consequence, or underlying cause; or further deterioration or occurrence of one or more additional symptoms of the disorder, disease condition, or symptom. Thus, a successful treatment outcome leads to a "therapeutic effect," or "benefit" or inhibiting, reducing or preventing the occurrence, frequency, severity, progression, or duration of one or more symptoms or underlying causes or consequences of a condition, disorder, disease or symptom in the subject. Treatment methods and uses affecting one or more underlying causes of the condition, disorder, disease or symptom are therefore considered to be beneficial. Stabilizing or inhibiting progression or worsening of a disorder or condition is also a successful treatment outcome.

A therapeutic benefit or improvement therefore need not be complete ablation of any one, most or all symptoms, complications, consequences or underlying causes associated with the condition, disorder or disease. Thus, a satisfactory endpoint is achieved when there is a stabilization or an incremental improvement in a subject's condition, or a partial reduction in the occurrence, frequency, severity, progression, or duration, or inhibition or reversal, of one or more associated adverse symptoms or complications or consequences or underlying causes, worsening or progression (e.g., stabilizing one or more symptoms or complications of the condition, disorder or disease), of one or more of the physiological, biochemical or cellular manifestations or characteristics of the disorder or disease, over a short or long duration of time (hours, days, weeks, months, etc.).

In particular embodiments, a method or use of treatment results in partial or complete destruction of a metastatic or non-metastatic tumor, cancer, or neoplastic cell mass; volume, size or numbers of tumor or cancer metastatic cells; stimulating, inducing or increasing metastatic or non-metastatic tumor, cancer, or neoplastic cell necrosis, lysis or apoptosis; reducing metastatic or non-metastatic tumor, cancer, or neoplastic volume, size, cell mass; inhibiting or preventing establishment, progression or an increase in metastatic or non-metastatic tumor, cancer, or neoplastic volume, mass, size or cell numbers; inhibiting or decreasing the spread or dissemination of cells (e.g., metastasis) to other (secondary) distinct or distal sites, regions, tissues or organs in a subject, or establishment of cells (e.g., metastasis) at other (secondary) distinct or distal sites, regions, tissues or organs in a subject; or prolongs lifespan of the subject. In additional particular embodiments, a method or use of treatment results in reducing or decreasing severity, duration or frequency of an adverse symptom or complication associated with or caused by the metastatic or non-metastatic tumor, cancer, malignancy or neoplasia.

An amount sufficient or an amount effective can but need not be provided in a single administration or dose and, can but need not be, administered alone or in combination with another composition (e.g., chemotherapeutic or immune enhancing or stimulating agent), treatment, protocol or therapeutic regimen. For example, the amount may be proportionally increased as indicated by the need of the subject, status of the disorder, disease or condition treated or the side effects of treatment. In addition, an amount sufficient or an amount effective need not be sufficient or effective if given in single or multiple doses without a second composition (e.g., chemotherapeutic or immune stimulating agent), treatment, protocol or therapeutic regimen, since additional doses, amounts or duration above and beyond such doses, or additional compositions (e.g., chemotherapeutic or immune stimulating agents), treatments, protocols or therapeutic regimens may be included in order to be considered effective or sufficient in a given subject. Amounts considered sufficient also include amounts that result in a reduction of the use of another treatment, therapeutic regimen or protocol.

An amount sufficient or an amount effective need not be effective in each and every subject treated, prophylactically or therapeutically, nor a majority of treated subjects in a given group or population. As is typical for treatment or therapeutic methods, some subjects will exhibit greater or less response to a given treatment, therapeutic regimen or protocol. An amount sufficient or an amount effective refers to sufficiency or effectiveness in a particular subject, not a group or the general population. Such amounts will depend in part upon the condition treated, such as the type or stage of a metastatic or non-metastatic tumor, cancer, malignancy or neoplasia, the therapeutic effect desired, as well as the individual subject (e.g., the bioavailability within the subject, gender, age, etc.).

Particular non-limiting examples of therapeutic benefit or improvement for a metastatic or non-metastatic neoplasia, tumor, cancer or malignancy include a reduction in cell size, mass or volume, inhibiting an increase in cell size, mass or volume, a slowing or inhibition of worsening or progression, stimulating cell necrosis, lysis or apoptosis, reducing or inhibiting neoplastic or tumor metastasis, reducing mortality, and prolonging lifespan of a subject. Thus, inhibiting or delaying an increase in cell size, mass, volume or metastasis (stabilization) can increase lifespan (reduce mortality) even if only for a few days, weeks or months, even though complete ablation of the metastatic or non-metastatic neoplasia, tumor, cancer or malignancy has not occurred. Adverse symptoms and complications associated with a metastatic or non-metastatic neoplasia, tumor, cancer or malignancy that can be reduced or decreased include, for example, pain, nausea, discomfort, lack of appetite, lethargy and weakness. A reduction in the occurrence, frequency, severity, progression, or duration of a metastatic or non-metastatic neoplasia, tumor, cancer or malignancy, such as an improvement in subjective feeling (e.g., increased energy, appetite, reduced nausea, improved mobility or psychological well being, etc.), are therefore all examples of therapeutic benefit or improvement.

The term "subject" refers to animals, typically mammalian animals, such as humans, non human primates (apes, gibbons, chimpanzees, orangutans, macaques), domestic animals (dogs and cats), farm animals (horses, cows, goats, sheep, pigs) and experimental animal (mouse, rat, rabbit, guinea pig). Subjects include animal disease models, for example, animal models of a metastatic or non-metastatic tumor, cancer, malignancy or neoplasia.

Subjects appropriate for treatment include those having or at risk of having a metastatic or non-metastatic tumor, cancer, or neoplastic cell, those undergoing as well as those who are undergoing or have undergone metastatic or non-metastatic neoplasia, tumor, cancer or malignancy therapy, including subjects where the cancer or tumor is in remission. "At risk" subjects typically have risk factors associated with undesirable or aberrant cell proliferation, development of hyperplasia (e.g., a tumor or cancer).

Treatment can therefore result in decreasing, reducing, inhibiting, suppressing, limiting, controlling or preventing a response, disorder or disease, or an associated adverse symptom or consequence, or underlying cause; decreasing, reducing, inhibiting, suppressing, limiting, controlling or preventing a progression or worsening of a response, disorder or disease, symptom or consequence, or underlying cause; or further deterioration or occurrence of one or more additional adverse symptoms of the response, disorder or disease. Thus, a successful treatment outcome can lead to a "therapeutic effect," or "benefit" of decreasing, reducing, inhibiting, suppressing, limiting, controlling or preventing the occurrence, frequency, severity, progression, or duration. Treatment methods affecting one or more underlying causes of the response, disorder or disease or adverse symptom are therefore considered to be beneficial. Stabilizing a response, disorder or disease, or an adverse symptom thereof, is also a successful treatment outcome.

An effective amount or a sufficient amount can but need not be provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the response, disorder, or disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered sufficient also include amounts that result in a reduction of the use of another treatment, therapeutic regimen or protocol.

An effective amount or a sufficient amount need not be effective in each and every subject treated, prophylactically or therapeutically, nor a majority of treated subjects in a given group or population. An effective amount or a sufficient amount means effectiveness or sufficiency in a particular subject, or an amount presumed to be effective based upon effectiveness or sufficiency in similarly matched subjects, but not a group or the general population. As is typical for such methods and uses, some subjects will exhibit a greater response, or less or no response to a treatment method or use.

As is typical for treatment or therapeutic methods, some subjects will exhibit greater or less response to a given treatment, therapeutic regimen or protocol. Thus, appropriate amounts will depend upon the response, disorder or disease treated (e.g., the type, status, extent or severity of neoplasia, tumor, cancer or malignancy and metastases), the therapeutic effect desired, as well as the individual subject (e.g., overall health, the bioavailability, gender, age, etc.).

Nur77 polypeptides and subsequences, Nur77 agonists, CX3CR1 agonists, Nur77 regulated monocytes (e.g., CD14$^+$ CD16$^+$ or CD14$^{dim}$CD16$^+$ (CD115$^+$CD11b$^+$GR1$^-$ (Ly6C-)) monocytes, or CD14$^+$ CD16$^+$ monocytes or CD14$^{dim}$CD16$^+$ (CD115$^+$CD11b$^+$GR1$^-$ (Ly6C-)) monocytes contacted with a Nur77 agonist or contacted with a CX3CR1 agonist, and compositions thereof may be contacted or provided in vitro, ex vivo or administered or delivered in vivo. Nur77 polypeptides and subsequences, Nur77 agonists, CX3CR1 agonists, Nur77 regulated monocytes (e.g., CD14$^+$ CD16$^+$ or CD14$^{dim}$CD16$^+$ (CD115$^+$CD11b$^+$GR1$^-$ (Ly6C-)) monocytes, or CD14$^+$ CD16$^+$ monocytes or CD14$^{dim}$CD16$^+$ (CD115$^+$CD11b$^+$GR1$^-$ (Ly6C-)) monocytes contacted with a Nur77 agonist or contacted with a CX3CR1 agonist, and compositions thereof can be administered or delivered to provide the intended effect, as single or multiple dosages, for example, in an effective or sufficient amount.

Single or multiple doses can be administered on the same or consecutive days, alternating days or intermittently. For example, a Nur77 polypeptides and subsequences, Nur77 agonists, CX3CR1 agonists, Nur77 regulated monocytes (e.g., CD14$^+$CD16$^+$ or CD14$^{dim}$ CD16$^+$ (CD115$^+$CD11b$^+$ GR1$^-$ (Ly6C-)) monocytes, or CD14$^+$ CD16$^+$ monocytes or CD14$^{dim}$CD16$^+$ (CD115$^+$CD11b$^+$GR1$^-$ (Ly6C-)) monocytes contacted with a Nur77 agonist or contacted with a CX3CR1 agonist, or composition thereof can be administered one, two, three, four or more times daily, on alternating days, bi-weekly, weekly, monthly, bi-monthly, or annually. Nur77 polypeptides and subsequences, Nur77 agonists, CX3CR1 agonists, Nur77 regulated monocytes (e.g., CD14$^+$ CD16$^+$ or CD14$^{dim}$CD16$^+$ (CD115$^+$CD11b$^+$GR1$^-$ (Ly6C-)) monocytes, or CD14$^+$ CD16$^+$ monocytes or CD14$^{dim}$CD16$^+$ (CD115$^+$CD11b$^+$GR1$^-$ (Ly6C-)) monocytes contacted with a Nur77 agonist or contacted with a CX3CR1 agonist, and compositions thereof can be administered for any appropriate duration, for example, for period of 1 hour, or less, e.g., 30 minutes or less, 15 minutes or less, 5 minutes or less, or 1 minute or less.

Exemplary doses range from about 25-250, 250-500, 500-1000, 1000-2500 or 2500-5000, 5000-25,000, 5000-50,000 pg/kg; from about 50-500, 500-5000, 5000-25,000 or 25,000-50,000 ng/kg; and from about 25-250, 250-500, 500-1000, 1000-2500 or 2500-5000, 5000-25,000, 5000-50,000 mg/kg, on consecutive days, alternating days or intermittently.

Nur77 polypeptides and subsequences, Nur77 agonists, CX3CR1 agonists, Nur77 regulated monocytes (e.g., CD14$^+$ CD16$^+$ or CD14$^{dim}$CD16$^+$ (CD115$^+$CD11b$^+$GR1$^-$ (Ly6C-)) monocytes, or CD14$^+$ CD16$^+$ monocytes or CD14$^{dim}$CD16$^+$ (CD115$^+$CD11b$^+$GR1$^-$ (Ly6C-)) monocytes contacted with a Nur77 agonist or contacted with a CX3CR1 agonist and compositions thereof can be administered to a subject and methods may be practiced substantially contemporaneously with, or within about 1-60 minutes, hours (e.g., within 1, 2, 3, 4 or 5 hours), or days of the onset of a neoplasia, tumor, cancer, malignancy or metastasis.

Nur77 polypeptides and subsequences, Nur77 agonists, CX3CR1 agonists, Nur77 regulated monocytes (e.g., CD14$^+$ CD16$^+$ or CD14$^{dim}$CD16$^+$ (CD115$^+$CD11b$^+$GR1$^-$ (Ly6C-)) monocytes, or CD14$^+$ CD16$^+$ monocytes or CD14$^{dim}$CD16$^+$ (CD115$^+$CD11b$^+$GR1$^-$ (Ly6C-)) monocytes contacted with a Nur77 agonist or contacted with a CX3CR1 agonist and compositions thereof can be administered and methods and uses may be practiced via systemic, regional or local administration, by any route. For example, a Nur77 polypeptide, subsequence, Nur77 agonist, CX3CR1 agonist, Nur77 regulated monocytes (e.g., CD14$^+$ CD16$^+$ or CD14$^{dim}$CD16$^+$ (CD115$^+$CD11b$^+$GR1$^-$ (Ly6C-)) monocytes, or CD14$^+$ CD16$^+$ monocytes or CD14$^{dim}$CD16$^+$ (CD115$^+$CD11b$^+$ GR1$^-$ (Ly6C-)) monocytes contacted with a Nur77 agonist or contacted with a CX3CR1 agonist or composition thereof may be administered systemically, regionally or locally (e.g., into a region or site of inflammation) via injection, via infusion, by catheter, enema, intravenously, intraarterially, orally (e.g., ingestion or intranasal or inhalation), intramuscularly, intraperitoneally, intradermally, subcutaneously, intracavity, intrarectally, intracranially, topically, transdermally, optically, parenterally, e.g. transmucosally. Methods and uses of the invention including pharmaceutical formulations can be administered via a (micro) encapsulated delivery system or packaged into an implant for administration.

Nur77 polypeptides and subsequences, Nur77 agonists, CX3CR1 agonists, Nur77 regulated monocytes (e.g., CD14$^+$ CD16$^+$ or CD14$^{dim}$CD16$^+$ (CD115$^+$CD11b$^+$GR1$^-$ (Ly6C–)) monocytes, or CD14$^+$ CD16$^+$ monocytes or CD14$^{dim}$CD16$^+$ (CD115$^+$CD11b$^+$GR1$^-$ (Ly6C–)) monocytes contacted with a Nur77 agonist or contacted with a CX3CR1 agonist alone, or in combination with other drugs or agents, and methods and uses also include pharmaceutical compositions, which refer to "pharmaceutically acceptable" and "physiologically acceptable" carriers, diluents or excipients. As used herein, the term "pharmaceutically acceptable" and "physiologically acceptable," when referring to carriers, diluents or excipients includes solvents (aqueous or non-aqueous), detergents, solutions, emulsions, dispersion media, coatings, isotonic and absorption promoting or delaying agents, compatible with pharmaceutical administration and with the other components of the formulation. Such formulations include liquids (e.g., water and saline), such as an emulsion, suspension, syrup or elixir, and solid forms such as a tablet (coated or uncoated), capsule (hard or soft), powder, granule, crystal, or microbead.

Pharmaceutical compositions can be formulated to be compatible with a particular route of administration. Compositions for parenteral, intradermal, or subcutaneous administration can include a sterile diluent, such as water, saline solution, fixed oils, polyethylene glycols, glycerine, propylene glycol or other synthetic solvents. The preparation may contain one or more preservatives to prevent microorganism growth (e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose).

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and polyethylene glycol), and suitable mixtures thereof. Fluidity can be maintained, for example, by the use of a coating such as lecithin, or by the use of surfactants. Antibacterial and antifungal agents include, for example, parabens, chlorobutanol, phenol, ascorbic acid and thimerosal. Including an agent that delays absorption, for example, aluminum monostearate and gelatin can prolong absorption of injectable compositions.

For transmucosal or transdermal administration, penetrants appropriate to the barrier to be permeated are used in the formulation. Such penetrants are known in the art, and include, for example, for transmucosal administration, detergents, bile salts, and fusidic acid derivatives. Transmucosal administration can be accomplished through the use of nasal sprays, inhalation devices (e.g., aspirators) or suppositories. For transdermal administration, the active compounds are formulated into ointments, salves, gels, creams or patches.

Additional pharmaceutical formulations and delivery systems are known in the art and are applicable in the methods of the invention (see, e.g., Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms, Technonic Publishing Co., Inc., Lancaster, Pa., (1993); and Poznansky, et al., Drug Delivery Systems, R. L. Juliano, ed., Oxford, N.Y. (1980), pp. 253-315).

The Nur77 polypeptides and subsequences, Nur77 agonists, CX3CR1 agonists, Nur77 regulated monocytes (e.g., CD14$^+$ CD16$^+$ or CD14$^{dim}$CD16$^+$ (CD115$^+$CD11b$^+$GR1$^-$ (Ly6C–)) monocytes, or CD14$^+$ CD16$^+$ monocytes or CD14$^{dim}$CD16$^+$ (CD115$^+$CD11b$^+$GR1$^-$ (Ly6C–)) monocytes contacted with a Nur77 agonist or contacted with a CX3CR1 agonist and compositions thereof used in accordance with the invention, including proteins, treatments, therapies, agents, drugs and pharmaceutical formulations can be packaged in dosage unit form for ease of administration and uniformity of dosage. "Dosage unit form" as used herein refers to physically discrete units suited as unitary dosages treatment; each unit contains a quantity of the composition in association with the carrier, excipient, diluent, or vehicle calculated to produce the desired treatment or therapeutic (e.g., beneficial) effect. The unit dosage forms will depend on a variety of factors including, but not necessarily limited to, the particular composition employed, the effect to be achieved, and the pharmacodynamics and pharmacogenomics of the subject to be treated.

The invention provides kits including compositions of the invention (e.g., Nur77 polypeptides and subsequences, Nur77 agonists, CX3CR1 agonists, Nur77 regulated monocytes (e.g., CD14$^+$ CD16$^+$ or CD14$^{dim}$CD16$^+$ (CD115$^+$CD11b$^+$GR1$^-$ (Ly6C–)) monocytes, or CD14$^+$ CD16$^+$ monocytes or CD14$^{dim}$CD16$^+$ (CD115$^+$CD11b$^+$GR1$^-$ (Ly6C–)) monocytes contacted with a Nur77 agonist or contacted with a CX3CR1 agonist, etc.), combination compositions and pharmaceutical formulations thereof, packaged into suitable packaging material. Kits can be used to practice various methods and for various uses.

A kit typically includes a label or packaging insert including a description of the components or instructions for use in vitro, in vivo, or ex vivo, of the components therein. A kit can contain a collection of such components, e.g., Nur77 polypeptides and subsequences, Nur77 agonists, CX3CR1 agonists, Nur77 regulated monocytes (e.g., CD14$^+$ CD16$^+$ or CD14$^{dim}$ CD16$^+$ (CD115$^+$CD11b$^+$GR1$^-$ (Ly6C–)) monocytes, or CD14$^+$ CD16$^+$ monocytes or CD14$^{dim}$CD16$^+$ (CD115$^+$CD11b$^+$GR1$^-$ (Ly6C–)) monocytes contacted with a Nur77 agonist or contacted with a CX3CR1 agonist alone, or in combination with another therapeutically useful composition.

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., hard disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a response, disorder, or disease, or adverse symptom, for which a kit component may be used. Labels or inserts can include instructions for the clinician or for a subject for using one or more of the kit components in a method, treatment protocol or therapeutic regimen, or use. Instructions can include dosage amounts, frequency or duration, and instructions for practicing any of the methods, treatment protocols or therapeutic regimes and uses set forth herein. Exemplary instructions include, instructions for treating a neoplasia, tumor, cancer, malignancy or metastasis. Kits of the invention therefore can additionally include labels or instructions for practicing any of the methods of the invention described herein including treatment methods.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "a Nur77 polypeptide sequence" or a "Nur77 agonist" includes a plurality of such Nur77 polypeptide sequences (or subsequences or variants thereof) or agonists, and reference to "a Nur77 polypeptide activity or function" can include reference to one or more Nur77 polypeptide activities or functions, and so forth.

As used herein, numerical values are often presented in a range format throughout this document. The use of a range format is merely for convenience and brevity and should not be construed as an inflexible limitation on the scope of the invention. Accordingly, the use of a range expressly includes all possible subranges, all individual numerical values within that range, and all numerical values or numerical ranges including integers within such ranges and fractions of the values or the integers within ranges unless the context clearly indicates otherwise. This construction applies regardless of the breadth of the range and in all contexts throughout this document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100% also includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

In addition, reference to a range of 2-10 (e.g., amino acids) includes 2, 3, 4, 5, 6, 7, 8, 9, 10, as well as 1.1, 1.2, 1.3, 1.4, 1.5, etc., 2.1, 2.2, 2.3, 2.4, 2.5, etc., and any numerical range within such a ranges, such as 2-3, 2-4, 2-6, 3-6, 3-7, 4-8, 5-9, 5-10, etc. In a further example, reference to a range of 2-10, 10-20, 20-30, 30-40, 40-50, 50-60, 60-75, 75-100 includes any numerical value or range within or encompassing such values.

As also used herein a series of ranges are disclosed throughout this document. The use of a series of ranges includes combinations of the upper and lower ranges to provide another range. This construction applies regardless of the breadth of the range and in all contexts throughout this document. Thus, for example, reference to a series of ranges such as 2-10, 10-20, 20-30, 30-40, 40-50, 50-60, 60-75, 75-100, includes ranges such as 2-20, 2-30, 5-20, 5-30, 5-40, 5-50, 5-60, 10-30, 10-40, 10-50, and 20-40, 20-30, 20-40, 20-50, 30-50, 30-60, 30-100, and 40-60, 40-70, 40-100, 50-75, 50-100, 60-100, and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

The examples set forth below illustrate certain embodiments and do not limit the technology.

Example 1: Patrolling Monocytes Control Tumor Metastasis to the Lung

Monocytes and derived macrophages are important regulators of the tumor immune environment. In early stage tumors, tumor-promoting myeloid cells arise from reservoirs of progenitors in the spleen and bone marrow that require signaling of the chemokine receptor CCR2. Recruited CCR2/CCL2 dependent classical "inflammatory" monocytes (characterized as $CCR2^{high}Ly6C^+$ in mouse, and $CCR2^{high}CD14^+CD16^-$ in humans) contribute greatly to the tumor macrophage content, and promote growth and metastasis of primary tumors. However, very little is known about the role of nonclassical "patrolling" monocytes ($CX3CR1^{high}Ly6C^-$ in mouse, and $CX3CR1^{high}CD14^{dim}CD16^+$ in humans) in the growth and metastasis of tumors. Patrolling monocytes are involved in the resolution of inflammation and exhibit unique properties such as actively patrolling the vasculature, and acting as "intravascular housekeepers" that scavenge microparticles and remove cellular debris. We determined that the orphan nuclear receptor NR4A1 (Nur77) is a master regulator for the differentiation and survival of patrolling $Ly6C^-$ monocytes. Nur77 is most highly expressed in $Ly6C^-$ patrolling monocytes compared to other immune cells, and patrolling monocytes are specifically missing in Nur77 knockout mice.

Figure 1:
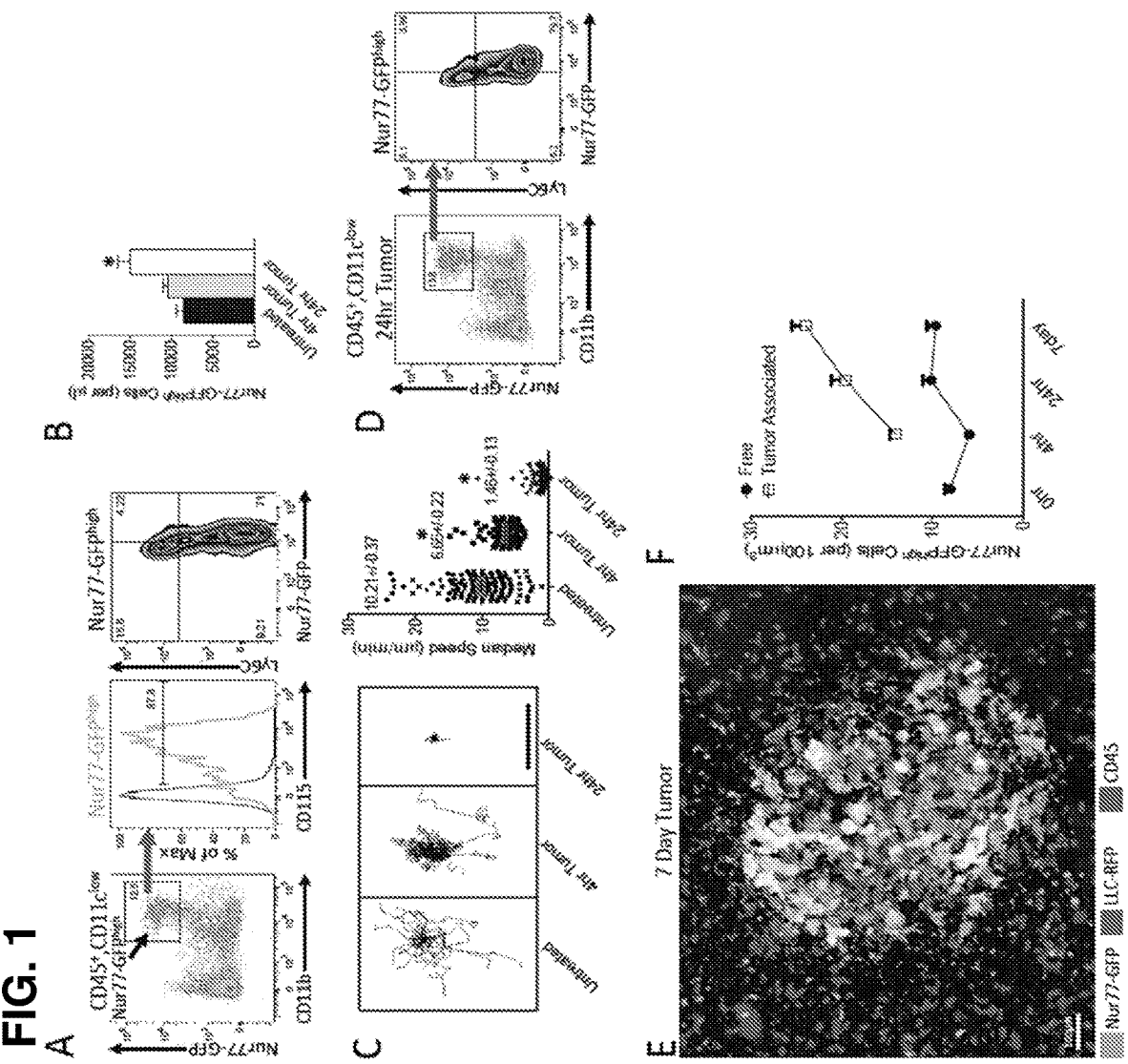
FIG. 1. Nur77-GFP$^{high}$ monocytes patrol the vasculature, and interact with tumor in the lung. (A) Gating of Nur77-

To investigate the interactions of $Ly6C^-$ patrolling monocytes in the tumor immune environment, were utilized mice expressing green fluorescent protein (GFP) under control of the Nur77 promoter (Nur77-GFP mice), which specifically labels Ly6C⁻ patrolling monocytes with high GFP intensity in the hematopoietic compartment. We focused our studies on the immune environment of the lung, which is a common site of primary tumor metastasis and is an important site of patrolling monocyte activities. We confirmed that Nur77-GFP$^{high}$ cells in the lung were Ly6C⁻CD11b⁺CD115⁺ (SSC$^{low}$MHC2⁻CD11c$^{low}$F4/80$^{low}$) patrolling monocytes by flow cytometry (FIG. 1A and FIG. 5A-B). Alveolar macrophages (CD11 C$^{high}$CD11b$^{low}$), which have low GFP-like autofluorescence but no detectable levels of Nur77-GFP expression (FIG. 5B), were gated out of this analysis. Live imaging and tracking of Nur77-GFP$^{high}$ cells by confocal imaging in the lungs identified a large number of Nur77-GFP$^{high}$ monocytes patrolling the microvasculature (FIG. 1B). Consistent with an important role of patrolling monocytes in the lung vasculature, we found a 3-4 fold enrichment of Nur77-GFP$^{high}$ patrolling monocytes in the lung compared to other tissues (FIG. 5C).

To examine the cellular interactions of patrolling monocytes with tumor in vivo, we imaged Nur77-GFP$^{high}$ patrolling monocytes in the lung after intravenous (IV) injection of Lewis Lung Carcinoma cells expressing red fluorescent protein (LLC-RFP). The number of Nur77-GFP$^{high}$ monocytes in the lung increased significantly 24 hrs following injection of LLC-RFP cells, implying that patrolling monocytes are being actively recruited to the lung tumor environment (FIG. 1B). Within 4 hrs after tumor injection, most Nur77-GFP$^{high}$ monocytes decreased patrolling speed in the vasculature, and at 24 hrs they were arrested near lung tumor sites (FIG. 1C). Nur77-GFP$^{high}$ cells isolated from the lung after LLC tumor transfer maintained expression of monocytic markers CD115 and CD11 b and were approximately 90% Ly6C⁻ (FIG. 5A, FIG. 1D). Changes in Ly6C or Nur77-GFP expression were also not observed in isolated monocyte populations co-cultured with tumor in vitro (FIG. 5D). Furthermore, Nur77-GFP$^{high}$ cells isolated from lung after 7 days of LLC tumor growth did not express high levels of MHC2 or F4/80 implying that the cells remain monocyte-like and are not converting to classically defined macrophage populations (FIG. 5A). Tumor associated MHC2⁺ CD11b⁺ macrophage populations expressed relatively low levels of Nur77 (FIG. 5B). Nur77-GFP$^{high}$ monocytes sensed and were recruited to tumor cell clusters less than 30 minutes after IV tumor injection, and continued to be recruited to tumor sites for at least 7 days (FIG. 1E-F). Nur77-GFP$^{high}$ cell recruited to lung tumor sites 24 hrs post injection did not stain for Ly6G/C⁺(GR-1+) in vivo, confirming that the Nur77-GFP$^{high}$ cells are Ly6G/C⁻ patrolling monocytes and not Ly6G⁺ granulocytes or Ly6C⁺ classical monocytes. Elevated frequencies of Ly6C⁻ monocytes in the lung were sustained for at least 24 hrs post tumor injection, in contrast to Ly6C⁺ monocyte populations, which rapidly increased at 4 hrs and recovered to normal levels by 24 hrs (FIG. 6A).

Nur77-GFP$^{high}$ monocytes still patrolling the vasculature after tumor inoculation were observed chasing down and preventing attachment of tumor cells or tumor material within the lung microvasculature at 4 hrs. Intravenous injection of anti-CD45 fluorescent antibody was used to label cells within the vasculature in order to identify and compare labeled immune cells found within the vasculature with unlabeled extravascular cells. By 4 hrs post-tumor injection, 10-20% of CD45⁻Nur77-GFP$^{high}$ monocytes had extravagated outside the vasculature at tumor sites (FIG. 6B-C). By 7 days post-tumor injection, approximately 40-50% of CD45⁻Nur77-GFP$^{high}$ monocytes could be found outside the vasculature at tumor sites, implying an extravascular function for these cells within the tumor environment (FIG. 6C). At 7 days of tumor growth, there were significantly higher numbers of Nur77-GFP$^{high}$ Ly6C⁻ patrolling monocytes (~24/100 µm³) associated with tumor areas, confirming active recruitment of patrolling monocytes to the tumor environment (FIG. 1E-F, FIG. 5A). Together, these findings confirm that patrolling monocytes establish early immune interactions with tumor cells and can accumulate at tumor sites.

In order to determine if patrolling monocytes have a role in regulating tumor invasion, metastasis and growth in the lungs in vivo, we used Nur77-knockout (Nur77⁻/⁻) mice, which have a specific ablation of patrolling monocytes. We confirmed that Nur77⁻/⁻ mice have a specific reduction of Ly6C⁻CD11b⁺CD115⁺CX3CR1$^{high}$ (SSQ$^{low}$MHC2⁻CD11c$^{low}$F4/80$^{low}$) patrolling monocytes (FIG. 7A), and no differences in other immune cell numbers or percentages in the lung hematopoietic compartment (FIG. 7B-D), similar to our observations of Nur77 functioning as a master transcriptional regulator of patrolling monocytes in blood and other tissues. The mice were IV injected with either syngeneic B16F10 melanoma expressing a luciferase reporter or LLC-RFP cells (FIG. 2A-B, FIGS. 8-9). As early as 24 hrs after IV injection of B16F10 melanoma, we observed increased tumor invasion in the lungs of Nur77⁻/⁻ mice compared to control mice, suggesting a very early and rapid innate immune response is important for the regulation of initial tumor invasion (FIG. 2A). Increased tumor numbers and size were continually observed in lungs of Nur77⁻/⁻ mice at 7 days (FIG. 2B) and 21 days after B16F10 tumor transfer (FIG. 8B-C). A selective absence of Ly6C⁻ patrolling monocytes in the lungs was maintained in Nur77⁻/⁻ mice at 7 days after tumor inoculation, and there were no observed differences in Ly6C⁺ monocyte or Ly6G⁺ granulocyte populations (FIG. 8A). A similar early and sustained increase in lung metastasis in Nur77⁻/⁻ mice was also observed with intravenous LLC tumor transfer (FIG. 9). Increased B16F10 tumor invasion appeared specific for the lung, as increased tumor metastasis was not observed in the liver (FIG. 8B-C), or other organs (data not shown). We also did not detect differences in subcutaneous (SubQ) tumor growth of B16F10 or LLC tumors (data not shown), or in vascular permeability in the lung between Nur77⁻/⁻ and control mice (FIG. 10). However, increased spontaneous metastases to the lung were observed in Nur77⁻/⁻ mice after SubQ injection of B16F10 melanoma, suggesting that Nur77 expression is important for suppressing primary tumor metastasis to the lung (FIG. 2C).

To further confirm that hematopoietic Nur77 expression regulates spontaneous tumor metastasis to the lung, Nur77⁻/⁻ or WT bone marrow was reconstituted into MMTV-PyMT female mice that spontaneously develop palpable mammary tumors which metastasize to the lung (1). MMTV-PyMT mice receiving Nur77⁻/⁻ bone marrow developed a significantly higher number of spontaneous metastases to the lung, but no differences in primary mammary tumor growth compared to mice receiving WT bone marrow (FIG. 2D-E).

In humans, single nucleotide polymorphisms in Nur77 have been associated with an increased risk of developing lung cancer, and low expression of Nur77 in lung tumor biopsies is associated with poor prognosis and decreased survival of lung cancer patients. However little is known about the expression of Nur77 in immune cells found within the tumor environment. To test if changes in hematopoietic cells were mediating the increase in lung metastasis that we observed in Nur77$^{-/-}$ mice, bone marrow chimeric mice were generated and subsequently challenged with B16F10 luciferase-expressing tumor cells. Wild-Type (WT) or Nur77$^{-/-}$ bone marrow was reconstituted alone or as a 1:1 (WT: Nur77$^{-/-}$) mixed chimera into WT recipient mice on differing CD45 congenic backgrounds (FIG. 2F-H). Mice receiving Nur77$^{-/-}$ bone marrow had increased tumor metastases, confirming that Nur77 expression in hematopoietic cells regulated tumor cell metastasis in the lung (FIG. 2F-G). Interestingly, mixed chimera mice did not show any significant increases in tumor metastases compared to WT chimera mice, demonstrating that even partial reconstitution of hematopoietic cells with WT, Nur77-proficient cells could rescue and prevent the tumor phenotype. Analysis of immune cells from the lung tumors verified a specific loss in Ly6C$^-$ monocytes in the Nur77$^{-/-}$ bone marrow chimera mice, which was restored by WT bone marrow reconstitution in the mixed chimeras (FIG. 2H). Further, in the 1:1 chimera mice, equal reconstitution of most CD45+ immune cell populations from each donor was observed (FIG. 11). However, Ly6C$^-$ monocytes were derived almost exclusively from WT bone marrow, suggesting that the restoration of the Ly6C$^-$ monocyte population prevented the metastasis. Thus, in multiple cancer models, including spontaneous MMTV-PyMT mice, absence of Nur77 in hematopoietic cells promoted tumor metastasis to lung.

In view of the above, we wanted to confirm if Nur77 expressed in myeloid cells was regulating tumor metastasis to the lung. Thus, we examined tumor lung metastasis in mice with myeloid-specific Nur77 deletion using two different conditional knockout mice (CSF1R-Cre$^+$Nur77$^{fl/fl}$ and LysM-Cre$^+$Nur77$^{fl/fl}$). Myeloid-selective deletion of Nur77 using both conditional knockout mouse models reduced Ly6C$^-$ monocytes in circulation (FIGS. 12A-D), and increased tumor lung metastasis (FIG. 3A-B, FIG. 13), similar to that observed in total Nur77$^{-/-}$ knockout and bone marrow-transplanted Nur77$^{-/-}$ mice (FIG. 2). CSF1R-Cre$^+$Nur77$^{fl/fl}$ mice exhibited an almost complete loss of Ly6C$^-$ patrolling monocytes (FIG. 12A-B). Reduced expression of Nur77 in myeloid cells of LysM-Cre$^+$Nur77$^{fl/fl}$ mice correlated positively with reductions in Ly6C$^-$ monocyte, but not Ly6C$^+$ monocyte, populations (FIG. 12E). Deletion of Nur77 in myeloid cells using CSF1R-Cre or LysM-Cre also targets macrophages and Ly6C$^+$ monocytes, so we cannot completely rule out a potential effect of Nur77 in these cells in our model, though expression of Nur77 in these cells is relatively low, suggesting limited Nur77 function in these cell types. No differences in tumor metastasis were observed in studies of conditional knockout mice with T lymphocyte-specific Nur77 deletion (FIG. 14). Taken together, these studies illustrate increased tumor incidence in the absence of Nur77 in myeloid cells in multiple lung cancer models, and further 5 indicate that Nur77-dependent patrolling monocytes play an important role in regulation of tumor metastasis.

To confirm a direct role for Ly6C$^-$ patrolling monocytes in regulating tumor metastasis, WT Ly6C$^+$ CX3CR1-GFP$^{low}$ or Ly6C$^-$ CX3CR1-GFP$^{high}$ monocytes were transferred into recipient Nur77$^{-/-}$ mice prior to tumor injection (FIG. 3C). WT Ly6C$^+$ CX3CR1-GFP$^{low}$ or Ly6C-CX3CR1-GFP$^{high}$ monocytes were transferred at a cell number of $5 \times 10^5$ per recipient, which is the approximate number of each monocyte subset found in normal mouse circulation. At 8-10 days after transfer, a significant number of transferred monocytes could be found in the lung (FIG. 15A-B). Importantly, reconstitution of Ly6C$^-$ monocytes into Nur77-deficient mice suppressed the increased tumor metastasis that occurs in Nur77-deficient mice, indicating that Ly6C$^-$ patrolling monocytes have a direct role in protection against tumor metastasis in the lung (FIG. 3D-E). In contrast, transfer of Ly6C$^+$ monocytes into Nur77$^{-/-}$ mice actually promoted tumor metastasis in vivo. The increased metastasis observed with Ly6C$^+$ monocyte transfer is consistent with protumoral properties of this subset of monocytes. The majority (80-90%) of transferred Ly6C$^+$ monocytes in circulation did not lose Ly6C$^-$ expression for at least 8 days after in vivo transfer and 7 days after B16F10 tumor transfer, implying that Ly6C$^+$ monocytes do not transition to Ly6C$^-$ monocytes in this tumor model of early metastasis (FIG. 15C). Transfer of WT lung resident macrophages or bone marrow-derived macrophages had no significant effect on tumor metastasis in Nur77$^{-/-}$ mice (data not shown). Reconstitution of Ly6C$^-$ monocytes 24 hrs after tumor injection did not suppress tumor metastasis in Nur77-deficient mice (FIG. 15D), suggesting that patrolling Ly6C$^-$ monocytes need to already be in the vasculature and active in order to prevent tumor metastasis and growth. These are the first data to directly show that patrolling monocytes play an important role in inhibiting tumor metastasis in the lung.

We used high-resolution confocal imaging to verify if patrolling monocytes could engulf and remove tumor material from the lung vasculature. A sizable number of Nur77-GFP patrolling monocytes containing large amounts of LLC-RFP tumor material were observed near tumor sites in the lung 24 hrs after IV tumor transfer (FIG. 3F; note that Nur77-GFP expression is primarily nuclear so monocyte cell membranes are not visible in images). Ex vivo and in vitro culture data confirmed that the tumor material was inside the patrolling monocytes. Co-culture assays of mouse CX3CR1-GFP$^{high}$ patrolling monocytes with fluorescent-labeled tumors showed complete engulfment of large amounts of tumor material (FIG. 3G). Further analysis of monocyte populations isolated from the lung 24 hrs after IV LLCRFP injection indicated that Ly6C$^-$ patrolling monocytes preferentially took up tumor material; taking up ~5-fold more tumor material than did Ly6C$^+$ classical monocytes (FIG. 3H). Ly6C$^-$ patrolling monocytes also preferentially took up significantly more B16F10-YFP tumor material in circulation as detected by ImageStream flow cytometry (FIG. 16A-C). The average size of tumor material taken up by patrolling monocytes was quantified as 1.39 µm$^2$ and the average total amount of tumor material per cell was 1.92 µm$^2$. The homologous human CD14$^{dim}$CD16$^+$ population of patrolling monocytes also has high Nur77 expression, and likely common function. In a co-culture assay of human CD14$^{dim}$CD16$^+$ patrolling monocytes with fluorescent labeled A549 human lung carcinoma cells, we observed that the human CD14$^{dim}$CD16$^+$ patrolling monocytes also engulfed a large quantity of tumor material, suggesting analogous tumor engulfment function (FIG. 16D). To determine if patrolling monocytes actively take up tumor material, LLC tumors were labeled with a pH-reactive pHrodo dye that increases fluorescence when taken into low pH endocytic vesicles. The ratio of the fluorescence of pHrodo-labeled tumor material engulfed by Ly6C$^-$ patrolling monocytes to the fluorescence of pHrodo-labeled whole tumor increased compared to control tumor material labeled with a non-pH sensitive dye (CellTrace Violet), indicating that patrolling monocytes actively engulf tumor material into lower pH endocytic vesicles (FIG. 4A). Collectively, these results demonstrate that Nur77-dependent patrolling monocytes are rapidly recruited to lung tumor sites, where they preferentially endocytose tumor material, and function to suppress tumor invasion and metastasis.

We then examined the mechanism by which patrolling monocytes respond to tumor cells to prevent metastasis in the lung. The chemokine receptor CX3CR1 is highly expressed on Ly6C⁻ patrolling monocytes and may be important for their arrest at inflammatory sites. Interestingly, CX3CR1-deficient (CX3CR1$^{-/-}$) mice, which also have a significant reduction in Ly6C⁻CX3CR1$^{high}$ patrolling monocytes, exhibit a similar phenotype to Nur77$^{-/-}$ mice of increased tumor burden and metastasis in the lung. Though Ly6C⁻ monocytes were reduced in numbers in the lung vasculature of CX3CR1-deficient mice (about 30-50% reduction, FIG. 17A), a major proportion of the CX3CR1-deficient Ly6C⁻ monocytes remaining were observed patrolling the vasculature. Importantly, we found that CX3CR1-deficient Ly6C⁻ patrolling monocytes were unable to sense and respond to tumor in the lung (FIG. 4B-C). Unlike CX3CR1$^{-/+}$ or WT patrolling monocytes, CX3CR1$^{-/-}$ monocytes did not respond to tumor cells and did not arrest in the lung vasculature at 24 hrs post-injection of LLC tumor cells, and instead remained patrolling the vasculature (FIG. 4B-C). CX3CR1$^{-/-}$ Ly6C⁻ patrolling monocytes were also not actively recruited to the lung 24 hrs after LLC tumor challenge, while Ly6C+ recruitment was unaffected by CX3CR1 expression (FIG. 17A). In addition, the remaining CX3CR1$^{-/-}$ Ly6C⁻ monocytes in the lung were also deficient in their ability to engulf tumor material, indicating that CX3CR1 expression on patrolling monocytes is critical for mediating sensing and uptake of tumor material (FIG. 4D).

CX3CL1, the only known ligand for CX3CR1, was specifically expressed on CD31+ endothelial cells in the lung microvasculature as measured by flow cytometry and confocal imaging using a CX3CL1-mCherry reporter mouse (FIG. 4E-F). Membrane-anchored CX3CL1, rather than shed CX3CL1, may be important for promoting patrolling monocyte survival. CX3CL1 expression was most prevalent in lung endothelial cells compared to endothelial cells of other tissues examined, which may partially explain the enrichment and preferential function of patrolling monocytes in the lung (FIG. 17B). Importantly, CX3CL1 expression increased on CD31⁺ endothelial cells in response to tumor challenge in the lung (FIG. 4E), and significant upregulation of CX3CL1 could be observed by endothelial cells at sites of tumor metastasis in the lung (FIG. 4F).

TLR7 expression was not found to play a role in either the recruitment of patrolling monocytes to the lung in response to tumor (FIG. 17A), or in the uptake of tumor material by patrolling monocytes (FIG. 4D). Thus, we conclude that CX3CR1 expression on monocytes and CX3CL1 expression by endothelial cells are critical for recruitment of patrolling monocytes to sites of tumor extravasation to mediate the removal of tumor material from the lung.

Finally, we examined whether patrolling monocytes can directly kill tumor cells. Analysis of monocyte subsets isolated from the lung by flow cytometry 24 hrs after in vivo interactions with tumor determined that Ly6C⁻ patrolling monocytes make significant amounts of the antitumoral chemokine TNFα in response to tumor (FIG. 18A). Nevertheless, after multiple attempts with various conditions, direct killing of tumor cells by Ly6C patrolling monocytes was not observed (FIG. 18B). It is a possibility that patrolling monocytes may be important for antibody-dependent cell-mediated cytotoxicity of tumor or suppressive immune cells. In response to IV injected B16F10 tumor, patrolling monocytes isolated from the lung produced significantly higher amounts of natural killer (NK) cell activation and recruitment-related chemokines CCL3, CCL4, and CCL5 compared to their classical Ly6C⁺ monocyte counterparts (FIG. 4G). In the absence of Nur77 expression in myeloid cells (CSF1R-Cre⁺Nur77$^{fl/fl}$), reduced NK cell recruitment was observed to the lung in response to tumor (FIG. 4H), suggesting that Ly6C⁻ patrolling monocytes are recruiting NK cells to the tumor sites. A similar reduction in NK cell recruitment (FIG. 19A), and activation (FIG. 19B) was found in the lungs of PyMT mice receiving Nur77-deficient bone marrow. We found no differences in neutrophil or Ly6C⁺ classical monocyte recruitment to these sites (data not shown), suggesting that neutrophils and classical monocytes are not playing a major role in tumor clearance in these models. Nur77 also does not appear to regulate NK cell development since there are no differences in NK cell developmental stages in the lungs of the PyMT model (FIG. 19C). Uptake of tumor material by patrolling monocytes does not require the presence of NK cells, as uptake of tumor material is unaffected by NK cell depletion.

In summary, we demonstrate that patrolling monocytes are actively recruited to metastasis sites in the lung in a CX3CR1-dependent manner. Patrolling monocytes function to engulf tumor material and recruit and activate NK cells, together which lead to the prevention of tumor cell metastasis in the lung (FIG. 21). Metastasis of tumors to the lung is a very common and often lethal event. Targeting patrolling monocyte antitumoral immunosurveillance activities and their regulation by Nur77 represents a novel therapy for preventing cancer metastasis to the lung. Further studies to identify possible specific ligands for enhancing Nur77 mediated patrolling monocyte activities could be important for targeted therapies in lung cancers.

REFERENCE (FOR ABOVE)

1. C. T. Guy, R. D. Cardiff, W. J. Muller, Induction of mammary tumors by expression of polyomavirus middle T oncogene: a transgenic mouse model for metastatic disease. *Mol Cell Biol* 12, 954-961 (1992).

Methods

Mice and Cell Lines

C57BL/6J wild-type mice (000664), and Nur77$^{-/-}$ mice (1) (006187), CX3CR1-GFP mice (008451), CX3CL1-mCherry mice (025525), TLR7$^{-/-}$ mice (008380), LysM-Cre mice (004781), Rag1$^{-/-}$ mice (00216), and MMTV-PyMT mice (022974) on a congenic C57BL/6J background were from The Jackson Laboratory. Csf1r-cre mice (021024) (2) were obtained from The Jackson Laboratories and littermate controls were used in experiments. B6.SJLPtprca/BoyAiTac mice (004007) were obtained from Taconic Farms. Mice were fed a standard rodent chow diet and were housed in microisolator cages in a special pathogen-free facility. The Nur77-GFP reporter mice were generated as described (3) and were a kind gift of Dr. Kristin Hogquist (University of Minnesota). Nur77$^{fl/fl}$ mice were generated as described (4). All experiments followed guidelines of the La Jolla Institute for Allergy and Immunology Animal Care and Use Committee, and approval for use of rodents was obtained from the La Jolla Institute for Allergy and Immunology according to criteria outlined in the Guide for the Care and Use of Laboratory Animals from the National Institutes of Health. Mice were euthanized by CO$_2$ inhalation.

Animals were randomly assigned to groups from available mice bred in our facility or ordered from distributer. Animals were unbiasedly assessed for tumor growth and metastasis. Automatic quantification of tumor and immune cell imaging was used if possible to avoid experimenter bias. Various alternative models were examined with respect to effect size, type 1 error, and power using nQuery Advisor 6.0 software. Via this analysis, we found that 90% power with 1% type 1 error can be achieved with 12 mice per group. Most experiments in this study used Male animals 8-12 weeks of age in good health. If animals were observed with non-experiment related health conditions (i.e. malocclusion, injuries from fighting, etc.) animals were removed from study groups Lewis lung carcinoma (LLC) cells, B16F10 melanoma, and RAW cells were obtained from ATCC. LLC cells stably expressing red fluorescent protein (RFP) were obtained from AntiCancer Incorporated. B16F10-luciferase expressing cells were kindly provided by the Kronenberg lab (LIAI), and B16F10 melanoma expressing yellow fluorescent protein (YFP) were obtained from Dr. Tomasz Zal at M.D. Anderson Cancer Center at Houston, Tex. Cell lines were tested for being pathogen free. Cell lines were maintained in DMEM medium containing 10% heat-inactivated FBS, 2 mmol/L l-glutamine, 1 mmol/L sodium pyruvate, 50 U/mL penicillin, 50 µg/mL streptomycin.

Imaging of Tumors and Patrolling Monocyte Interactions

Lewis lung carcinoma or B16F10 melanoma cells expressing luciferase were injected IV ($3 \times 10^5$ per mouse) through the tail vain. Luciferase activity was measured using an IVIS 200 Bioluminescence Imager (Caliper Life Sciences) after IV injection of 1 mg D-Luciferin (Caliper Life Sciences) in 100 µL PBS. After measuring luciferase activity lungs were removed, photographed and weighted to validate luciferase activity correlates with lung tumor mass. LLC-RFP tumors were observed by confocal imaging. Live imaging of the lung was conducted as previously described (5). In brief, mice were injected intraperitoneally with ketamine hydrochloride/xylazine hydrochloride anesthesia that was maintained during image acquisition for up to 3 hrs at 37° C. using a heated stage. Mice were put on a ventilator with tidal volumes of 8 to 10 µl/g body weight (room air or higher fractions of oxygen) and respiratory rates of approximately 120 breaths per minute. The thoracic cavity was exposed and three anterior ribs overlying the left lung lobe were removed. To stabilize the lung for imaging, a thoracic suction window with a sealed 12 mm glass coverslip and 20 to 25 mmHg of suction was applied to the left lung. To further identify immune cells in the tumor, 20 µg of AF647 conjugated anti-CD45, Ly6C or Ly6G was IV injected just before imaging. Images were acquired on a Leica SP5 Multiphoton/Confocal microscopy system with a resonant scanner.

Images were smoothed by median filtering at kernel size 3×3 pixels. Three dimensional reconstructions and drift correction of lung images were performed using Imaris software (version 7.1.1×64; Bitplane AG). When needed, motion artifacts caused by breathing were corrected with rigid body registration using an ImageJ plug-in (6, 7). Imaris software was also used to automatically process 3D video data by detecting cells in each fluorescence channel, then creating tracks by linking the detected cells over time. Tracks were manually edited to improve accuracy. For analysis of CX3CR1-GFP$^{high}$ patrolling monocytes, tracks of spherical mononuclear cells were carefully analyzed in 3 dimensions to avoid interference by CX3CR1-GFP$^{high}$ dendritic cells present on the surface of the lung. The software calculated cell velocities. Quantification of GFP$^{high}$ monocytes patrolling was performed in a 350×350 µm$^2$ field of view from 3 representative 20 min movies.

For analysis of Nur77GFP$^{high}$ patrolling monocytes per µl of blood volume, blood vessels were fitted with "isovolumes" using Imaris software to calculate the imaged blood vessel volume. The number of patrolling monocytes within this volume was quantified at multiple time points, then the number of crawling monocytes per time point was divided by the calculated volume in µl.

After live imaging, the lungs were extracted and large regions of the lungs were scanned by an Olympus FluoView FV10i microscope to create mosaics of the lung/tumor area. These mosaics were then scored manually for free (>100 µm from tumor site) and tumor-associated (<50 µm from tumor site) Nur77-GFP$^{high}$ monocytes in the lung at various time points after tumor injection. Five areas of at least 3 separate lungs per time point were analyzed. The total number of tumor metastases and Nur77-GFP$^{high}$ monocytes in the lung were also calculated from these images.

For analysis of spontaneous tumor metastasis to the lung, $1 \times 10^5$ B16F10-YFP expressing cells were injected SubQ in the rear flank of mice. Tumors were allowed to grow for 4 weeks or until tumors began effecting mouse movement or health. The lungs were then extracted and large regions of the lungs were scanned by an Olympus FluoView FV10i microscope to create mosaics of the lung/tumor area. Images were then quantified manually for the number of metastases per lung surface area. The numbers of metastases were quantified per 5000 µm$^2$ (the approximate surface area of the left lobe of the lung).

Flow Cytometry

Lungs were lavaged with Dulbecco's PBS (DPBS) (Gibco) containing 2 mM EDTA, excised, and smashed through a 70 µm strainer to disperse cells. Blood was obtained by cardiac puncture with an EDTA-coated syringe. All samples were collected in DPBS with 2 mM EDTA to prevent cation-dependent cell-cell adhesion, and were stored on ice during staining and analysis. Red blood cells were lysed in RBC Lysis Buffer according to the manufacturer's protocol (BioLegend). Cells ($2 \times 10^6$ to $4 \times 10^6$) were resuspended in 100 µl flow staining buffer (1% BSA (wt/vol) and 0.1% (wt/vol) sodium azide in PBS). Fcγ receptors were blocked for 15 min and surface antigens on cells were stained for 30 min at 4° C. with directly conjugated fluorescent antibodies (flow cytometry antibody list, FIG. S18). LIVE/DEAD Fixable Dead Cell Stain (Invitrogen) was used for analysis of viability, and forward- and side-scatter parameters were used for exclusion of doublets from analysis.

Calculations of percentages of CD45$^+$ immune cells were based on live cells as determined by forward and side scatter and viability analysis. Cell fluorescence was assessed with a LSRII (BD Biosciences) and was analyzed with FlowJo software (version 9.2). Mean fluorescence intensity was quantified, and expression was calculated relative to that of the WT control. Lung immune cell were sorted using a FACSAria (BD Biosciences) and washed 2 times in DPBS.

Bone Marrow Transplantation

Recipient mice (WT or Nur77$^{-/-}$) were irradiated in two doses of 550 rads each (for a total of 1,100 rads) 4 hrs apart. Bone marrow cells from both femurs and tibias of donor mice (WT or Nur77$^{-/-}$) were collected under sterile conditions. Bones were centrifuged for the collection of marrow, then cells were washed and resuspended in DPBS for injection. Approximately $5 \times 10^6$ unfractionated bone marrow cells in 200 µl media were delivered retroorbitally into each recipient mouse. Recipient mice were housed in a barrier facility under pathogen-free conditions before and after bone marrow transplantation. After bone marrow transplantation, mice were provided autoclaved acidified water with antibiotics (trimethoprimsulfamethoxazole) and were fed autoclaved food. Mice were used for experiments after 6 weeks of bone marrow reconstitution. For mixed bone marrow chimeras mice on differing CD45 (CD45.1 or CD45.2) congenic backgrounds were used donors to track transferred cells in recipient mice. CD45.1$^+$ B6.SJLPtprca/BoyAiTac (WT CD45.1) and CD45.2$^+$ Nur77$^{-/-}$ (Nur77$^{-/-}$ CD45.2) mouse donor bone marrow was transferred into CD45.2+ C57BL/6 (WT CD45.2) or CD45.1$^+$ B6.SJLPtprca/BoyAiTac (WT CD45.1) recipient mice. For this transplantation, $2.5 \times 10^6$ cells from Nur77$^{-/-}$ mice (Nur77$^{-/-}$ CD45.2+) and $2.5 \times 10^6$ cells from B6.SJL-Ptprca/BoyAiTac mice (WT CD45.1$^+$) were mixed at a ratio of 1:1 for reconstitution of recipients as described above.

MMTV-PyMT Mouse Tumor Analysis

Six-Eight week old MMTV-PyMT mice were reconstituted WT or Nur77$^{-/-}$ bone marrow as described above. Primary mammary tumors could begin to be observed at ~14 weeks of life or 6-8 weeks after bone marrow transplant. Primary mammary tumors were measured by digital calipers and calculated as height×width$^2$/2. Mice were taken down and analyzed for lung metastasis when the primary mammary tumors reached 1000 mm$^3$. Lungs were then fixed in buffered zinc formalin, embedded in paraffin, sectioned, and then hematoxylin and eosin stained. The number of metastases per area of lung was quantified by microscopy.

T Cell Transfer

Total T cells were isolated from thymus of WT and Nur77$^{-/-}$ mice using a negative selection kit (Pan T Cell Isolation Kit II, Miltenyi Biotec). Approximately $5 \times 10^6$ nave T cells from either WT or Nur77$^{-/-}$ mice were transferred IV into Rag$^{-/-}$ mice. Mice were rested for 20 days to allow complete T cell reconstitution and then challenged by IV injection of $3 \times 10^5$ B16F10-Luciferase cells. Tumors were allowed to develop of 7 days and then imaged.

Vascular Permeability

Pulmonary vascular permeability was evaluated by measurement of Evans blue dye (EBD) extravasation. EBD (30 mg/kg body weight, 200 µL) was injected intravenously in mice anesthetized with ketamine/xylazine and allowed to circulate for 30 minutes. The chest was opened, the inferior vena cava transected, and the pulmonary vasculature flushed with 10 mL saline via the right ventricle to remove excess intravascular dye. The lung was homogenized and incubated in 100% formamide at 37° C. for 24 hours to extract EBD. The concentration of EBD extracted was analyzed by spectophotometry. Correction of optical densities (E) for contaminating heme pigments was performed as previously described, using the equation: E620(corrected)=E620−(1.426×E740+0.03) (8). Data were calculated as micrograms EBD per gram lung.

Monocyte Transfer

CX3CR1-GFP expression from heterozygous CX3CR1-GFP reporter mice were used to isolate monocyte populations without labeling for CD115 (CSF1R), and thus avoiding any deleterious changes to M-CSF signaling in monocytes (9). CX3CR1-GFP mice have EGFP knocked into the CX3CR1 locus, and previous studies have demonstrated that heterozygous CX3CR1-GFP expression does not affect monocyte function (10). Wild-type Ly6C$^-$CX3CR1-GFP$^{high}$ monocytes, and Ly6C$^+$CX3CR1-GFP$^{low}$Lin$^-$ (NK1.1, Ly6G, CD3, CD19) monocytes were sorted from CX3CR1-GFP$^{-/+}$ blood and spleen by flow cytometry. Approximately $5 \times 10^5$ immune cells were transferred by retro-orbital IV injection to Nur77$^{-/-}$ mice. The following day (or 24 hrs prior to monocyte transfer for other experiments) $3 \times 10^5$ B16F10-luciferase cells were transferred by IV tail vein injection. The data for the transfer experiments are from 5 separate experiment with n=2 per group. Tumors were grown in mice for 1 week and then imaged in vivo for luciferase activity. In separate experiments monocyte subsets were isolated from CD45.2$^+$DsRed$^+$ mice and transferred into CD45.1$^+$ recipients to better track the fate of transferred cells.

Quantification of Tumor Material Uptake

For analysis of monocyte uptake of tumor in vivo, $5 \times 10^5$ LLC-RFP or B16F10-YFP cells were IV injected. Three hrs or 24 hrs after IV tumor injections, lungs and blood were prepped for flow cytometry as described above, and the amount of RFP$^+$ or YFP$^+$ tumor material in monocyte populations was quantified by flow cytometry. Non-fluorescent LLC or B16F10 tumor cells were also labeled with CellTrace Violet (Life Technologies) following the manufacturers directions, and monocyte uptake was quantified in some experiments. For in vivo depletion of NK cells, 200 µg anti-NK1.1 (PK136) antibody was injected IV one day before transfer of LLCRFP tumors. Cell depletion from lung was verified by flow cytometry. The Amnis ImageStreamX MarkII Imaging Cytometer was also used to visualize Ly6C$^-$ patrolling monocytes uptake of B16F10-YFP tumor material in circulation. The average size, and total amount of B16F10-YFP tumor material taken up by patrolling monocytes was quantified from fluorescent cell images using ImageJ analysis software.

In Vitro uptake of tumor material was also measured in culture for mouse CX3CR1-GFP$^{high}$ and human CD14$^{dim}$CD16$^+$ patrolling monocytes. CX3CR1-GFP$^{high}$ patrolling monocytes were isolated by flow sorting and plated in co-culture with LLC-RFP cells. CD14$^{dim}$CD16$^+$ human monocytes were isolated from healthy donors by flow cytometry as previously described (11), and plated in co-culture with A549 tumor cells labeled with CellTracker Green dye according to the manufacturer's instructions (Life Technologies). Fifty thousand monocytes were cultured with 10,000 tumor cells per well on 8 well chamber cover slips. A 5:1 ratio of monocytes to tumor cells was used since a similar ratio of monocytes to tumor cells was observed at early time points in the lung in vivo. High-resolution confocal images were taken 24 hrs after co-culture at 37° C. to identify RFP tumor material uptake by monocytes.

To determine if patrolling monocytes actively uptake tumor material, LLC tumors were labeled with a pH-reactive pHrodo dye (Life Technologies) that increases fluorescence when taken into low pH endocytic vesicles. For this assay LLC tumor cells were labeled either with the pH-sensitive pHrodo dye or the pH insensitive CellTrace Violet dye. Tumor cells were then injected in a 1:1 ratio of $2.5 \times 10^5$ LLC-pHrodo labeled: $2.5 \times 10^5$ LLC-CellTrace Violet labeled cells into a recipient mouse. To compensate for the loss of fluorescent intensity due to the smaller size of tumor material taken up by monocytes compared to fluorescent intensity of whole tumor, the average mean fluorescence of tumor material uptake per monocyte population was then compared to the total mean fluorescence of the tumor cells for each dye and expressed as a ratio (mean fluorescent intensity of tumor material taken up by monocyte to the total fluorescent intensity of the tumor). Comparing the ratio of taken up tumor material to the whole tumor for pH insensitive CellTrace Violet dye, to the ratio for the pH sensitive pHrodo dye can then asses any change in pHrodo fluorescence of tumor material taken up by monocytes, and can be used as an indicator of pH changes associated with endocytosis.

Analysis of CX3CL1 Expression in Lung

CX3CL1-mCherry mice, which express mCherry transgene under expression of the CX3CL1 promoter, were used to identify CX3CL1 expression in the lung. CX3CL1-mCherry mice were IV injected with $3\times10^5$ B16F10-YFP tumor cells and then the lung imaged 24 hrs or 7 days after IV injections as described above. For isolation and analysis of CX3CL1 expression in endothelial cells, lung spleen, liver and kidney were chopped with scissors into small pieces, and digested with 125 U/mL collagenase type XI, 60 U/mL hyaluronidase type 1-s, 60 U/mL DNAse1, and 450 U/mL collagenase type I (all enzymes, Sigma) in PBS containing 20 mmol/L HEPES at 37° C. for 1 hour. A cell suspension was obtained by mashing the tissue through a 70-μm strainer. Cells were then stained for flow cytometry as described above. Endothelial cells were identified as $CD31^+CD45^-$ cells.

In Vitro Tumor Cytotoxicity Assay

FACS isolated $Ly6C^+$ and $Ly6C^-$ monocytes were plated in round well 96-well plates at $4\times10^5$ cells/well in 200 μl R5 (RPMI+5% FBS) and stimulated with IFNγ (20 ng/ml) and LPS (100 ng/ml) for 24 hrs. The cells were washed with R5 twice and co-cultured with tumor cells in 40:1, 20:1 or 10:1 ratio of effector (monocytes):target cells (tumor cells). After 24 hrs later, the cells were washed with PBS and treated with Accutase™ cell detachment solution (BD Biosciences). Tumor cell viability was determined with Live/Dead Aqua (Life Technologies) staining by flow cytometry. Tumor cytotoxicity was calculated as % of Live/Dead $Aqua^+$ tumor cells.

Quantitative Real-Time PCR

Monocyte were isolated from the lung by FACS 24 hrs after IV injection of $3\times10^5$ B16F10 tumor cells, and total cellular RNA was collected with an RNeasy Plus Micro Kit according to the manufacturer's protocol (Qiagen). RNA purity and quantity was measured with a nanodrop spectrophotometer (Thermo Scientific). Approximately 100 ng RNA was used for synthesis of cDNA with an Iscript cDNA Synthesis Kit (Bio-Rad). Total cDNA was diluted 1:20 in $H_2O$, and a volume of 9 μl was used for each real-time condition with a MyIQ Single-Color Real-Time PCR Detection System (Bio-Rad) and TaqMan Gene Expression Mastermix and TaqMan primers (FIG. 13). Data were analyzed and presented on the basis of the relative expression method. The formula for this calculation was as follows: relative expression=$2(S\Delta CT-C\Delta CT)$, where $\Delta CT$ is the change in cycling threshold between the gene of interest and the 'housekeeping' gene Gapdh (encoding glyceraldehyde phosphate dehydrogenase), S is the result obtained with $Nur77^{-/-}$ cells, and C is the result obtained with C57BL/6J control cells. The expression of each wild-type transcript was calculated relative to the mean wild-type transcript expression to show variability in wild-type samples. The mean $Ly6C^+$ transcript expression was then compared with that of transcripts from each $Ly6C^-$ sample to determine the change relative to $Ly6C^+$ expression.

Statistical Analysis

Data for all experiments were analyzed with Prism software (GraphPad). Unpaired t-tests and two-way analysis of variance were used for comparison of experimental groups. P values of less than 0.05 were considered significant. The data appeared to be normally distributed with similar standard deviation and error observed between and within experimental groups.

REFERENCES (METHODS SECTION)

1. S. Lee et al., Unimpaired thymic and peripheral T cell death in mice lacking the nuclear receptor NGFI-B (Nur77). *Science* 269, 532-535 (1995).
2. L. Deng et al., A novel mouse model of inflammatory bowel disease links mammalian target of rapamycin-dependent hyperproliferation of colonic epithelium to inflammation associated tumorigenesis. *Am J Pathol* 176, 952-967 (2010).
3. A. E. Moran et al., T cell receptor signal strength in Treg and iNKT cell development demonstrated by a novel fluorescent reporter mouse. *J Exp Med*, (2011).
4. T. Sekiya et al., The nuclear orphan receptor Nr4a2 induces Foxp3 and regulates differentiation of CD4+ T cells. *Nat Commun* 2, 269 (2011).
5. E. E. Thornton, M. F. Krummel, M. R. Looney, Live imaging of the lung. *Curr Protoc Cytom* Chapter 12, Unit12.28 (2012).
6. M. S, A. S, L. K, R. N, in IEEE International Conference on Image Processing. (2014).
7. S. McArdle, G. Chodaczek, N. Ray, K. Ley, Intravital live cell triggered imaging system reveals monocyte patrolling and macrophage migration in atherosclerotic arteries. *J Biomed Opt* 20, 26005 (2015).
8. K. L. Wallace, J. Linden, Adenosine A2A receptors induced on iNKT and NK cells reduce pulmonary inflammation and injury in mice with sickle cell disease. *Blood* 116, 5010-5020 (2010).
9. S. Jung et al., Analysis of fractalkine receptor CX(3)CR1 function by targeted deletion and green fluorescent protein reporter gene insertion. *Mol Cell Biol* 20, 4106-4114 (2000).
10. L. Landsman et al., CX3CR1 is required for monocyte homeostasis and atherogenesis by promoting cell survival. *Blood* 113, 963-972 (2009).
11. R. N. Hanna et al., NR4A1 (Nur77) deletion polarizes macrophages toward an inflammatory phenotype and increases atherosclerosis. *Circ Res* 110, 416-427 (2012).

TABLE 2

Antibody Clones Used for Flow Cytometry

| Antibody | Company | Clone |
| --- | --- | --- |
| CD3e | BD Pharmingen | 145-2C11 |
| CD11c | eBioscience | N418 |
| CD115 | Biolegend | AFS98 |
| CD11b | BD Pharmingen | M1/70 |
| CD19 | eBioscience | 1D3 |
| CD27 | Biolegend | LG.3A10 |
| CD31 | Biolegend | 390 |
| CD44 | Biolegend | IM7 |
| CD49b | eBioscience | DX5 |
| CD45 | Biolegend | 30-F11 |
| Ly6C | Biolegend | HK1.4 |
| Ly6G | Biolegend | 1A8 |
| Ly6G/C (GR-1) | Biolegend | RB6-8C5 |
| MHC2 | eBioscience | M5/114.15.2 |
| F4/80 | Biolegend | BM8 |
| Siglec-F | BD Biosciences | E50-2440 |
| NK1.1 | Biolegend | PK136 |
| CD14 (anti-Human) | Biolegend | M5E2 |
| CD16 (anti-Human) | Biolegend | 3G8 |
| HLA-DR (anti-Human) | Biolegend | L243 |
| CD86 (anti-Human) | Biolegend | 1T2.2 |
| CD19 (anti-Human) | Biolegend | HIB |
| CD3 (anti-Human) | Biolegend | UCHT1 |
| CD66B (anti-Human) | Biolegend | G10F5 |

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method of controlling, limiting, or decreasing metastasis of a tumor or cancer in a subject, comprising administering CD14$^+$ CD16$^+$ monocytes and/or CD14$^{dim}$CD16$^+$ (CD115$^+$CD11b$^+$GR1$^-$ (Ly6C–)) monocytes to a subject having or at risk of having a cancer or tumor, wherein the metastasis of the tumor or cancer in the subject is controlled, limited or decreased.

2. The method of claim 1, wherein the method decreases, reduces, inhibits, suppresses, limits or controls metastasis of the cancer or tumor, or decreases, reduces, inhibits, suppresses, limits or controls establishment of a tumor or cancer metastasis at one or more sites other than the original site of the tumor or cancer in the subject.

3. The method of claim 1, wherein the method decreases, reduces, inhibits, suppresses, limits or controls growth or proliferation of a tumor or cancer metastasis at one or more sites other than the original site of the tumor or cancer in the subject.

4. The method of claim 1, wherein the method decreases or reduces tumor or cancer metastasis at one or more sites other than the original site of the tumor or cancer in the subject.

5. The method of claim 1, wherein the tumor or cancer metastasis is in a lung in the subject.

6. The method of claim 1, wherein the site(s) other than the original site of the tumor or cancer is a lung.

7. The method of claim 1, wherein the method stimulates, promotes, increases or induces CD14$^+$ CD16$^+$ or CD14$^{dim}$ CD16$^+$ monocyte cell production, development, survival, proliferation, differentiation or activity.

8. The method of claim 1, wherein the subject is in need of treatment for a tumor or cancer.

9. The method of any of claim 1, wherein the subject has been treated or is in remission from a tumor or cancer.

10. The method of claim 1, wherein the cancer or tumor comprises a carcinoma, sarcoma, lymphoma, leukemia, adenoma, adenocarcinoma, melanoma, glioma, glioblastoma, meningioma, neuroblastoma, retinoblastoma, astrocytoma, oligodendrocytoma, mesothelioma, reticuloendothelial, lymphatic, lung or haematopoietic cancer or tumor.

11. The method of claim 1, wherein the cancer or tumor comprises a myeloma, lymphoma or leukemia.

12. The method of claim 1, wherein the cancer or tumor comprises leukemia or melanoma.

* * * * *

SEQUENCE LISTING

```
<160> NUMBER OF SEQ ID NOS: 2

<210> SEQ ID NO 1
<211> LENGTH: 611
<212> TYPE: PRT
<213> ORGANISM: Homo sapiens

<400> SEQUENCE: 1

Met Trp Leu Ala Lys Ala Cys Trp Ser Ile Gln Ser Glu Met Pro Cys
1               5                   10                  15

Ile Gln Ala Gln Tyr Gly Thr Pro Ala Pro Ser Pro Gly Pro Arg Asp
                20                  25                  30

His Leu Ala Ser Asp Pro Leu Thr Pro Glu Phe Ile Lys Pro Thr Met
            35                  40                  45

Asp Leu Ala Ser Pro Glu Ala Ala Pro Ala Ala Pro Thr Ala Leu Pro
        50                  55                  60

Ser Phe Ser Thr Phe Met Asp Gly Tyr Thr Gly Glu Phe Asp Thr Phe
65                  70                  75                  80

Leu Tyr Gln Leu Pro Gly Thr Val Gln Pro Cys Ser Ser Ala Ser Ser
                85                  90                  95

Ser Ala Ser Ser Thr Ser Ser Ser Ala Thr Ser Pro Ala Ser Ala
                100                 105                 110

Ser Phe Lys Phe Glu Asp Phe Gln Val Tyr Gly Cys Tyr Pro Gly Pro
            115                 120                 125

Leu Ser Gly Pro Val Asp Glu Ala Leu Ser Ser Ser Gly Ser Asp Tyr
        130                 135                 140

Tyr Gly Ser Pro Cys Ser Ala Pro Ser Pro Ser Thr Pro Ser Phe Gln
145                 150                 155                 160

Pro Pro Gln Leu Ser Pro Trp Asp Gly Ser Phe Gly His Phe Ser Pro
                165                 170                 175

Ser Gln Thr Tyr Glu Gly Leu Arg Ala Trp Thr Glu Gln Leu Pro Lys
            180                 185                 190

Ala Ser Gly Pro Pro Gln Pro Ala Phe Phe Ser Phe Ser Pro Pro
        195                 200                 205

Thr Gly Pro Ser Pro Ser Leu Ala Gln Ser Pro Leu Lys Leu Phe Pro
210                 215                 220
```

```
Ser Gln Ala Thr His Gln Leu Gly Glu Gly Ser Tyr Ser Met Pro
225                 230                 235                 240

Thr Ala Phe Pro Gly Leu Ala Pro Thr Ser Pro His Leu Glu Gly Ser
            245                 250                 255

Gly Ile Leu Asp Thr Pro Val Thr Ser Thr Lys Ala Arg Ser Gly Ala
        260                 265                 270

Pro Gly Gly Ser Glu Gly Arg Cys Ala Val Cys Gly Asp Asn Ala Ser
    275                 280                 285

Cys Gln His Tyr Gly Val Arg Thr Cys Glu Gly Cys Lys Gly Phe Phe
290                 295                 300

Lys Arg Thr Val Gln Lys Asn Ala Lys Tyr Ile Cys Leu Ala Asn Lys
305                 310                 315                 320

Asp Cys Pro Val Asp Lys Arg Arg Asn Arg Cys Gln Phe Cys Arg
            325                 330                 335

Phe Gln Lys Cys Leu Ala Val Gly Met Val Lys Glu Val Val Arg Thr
            340                 345                 350

Asp Ser Leu Lys Gly Arg Arg Gly Arg Leu Pro Ser Lys Pro Lys Gln
            355                 360                 365

Pro Pro Asp Ala Ser Pro Ala Asn Leu Leu Thr Ser Leu Val Arg Ala
370                 375                 380

His Leu Asp Ser Gly Pro Ser Thr Ala Lys Leu Asp Tyr Ser Lys Phe
385                 390                 395                 400

Gln Glu Leu Val Leu Pro His Phe Gly Lys Glu Asp Ala Gly Asp Val
                405                 410                 415

Gln Gln Phe Tyr Asp Leu Leu Ser Gly Ser Leu Glu Val Ile Arg Lys
            420                 425                 430

Trp Ala Glu Lys Ile Pro Gly Phe Ala Glu Leu Ser Pro Ala Asp Gln
            435                 440                 445

Asp Leu Leu Leu Glu Ser Ala Phe Leu Glu Leu Phe Ile Leu Arg Leu
        450                 455                 460

Ala Tyr Arg Ser Lys Pro Gly Glu Gly Lys Leu Ile Phe Cys Ser Gly
465                 470                 475                 480

Leu Val Leu His Arg Leu Gln Cys Ala Arg Gly Phe Gly Asp Trp Ile
            485                 490                 495

Asp Ser Ile Leu Ala Phe Ser Arg Ser Leu His Ser Leu Leu Val Asp
        500                 505                 510

Val Pro Ala Phe Ala Cys Leu Ser Ala Leu Val Leu Ile Thr Asp Arg
    515                 520                 525

His Gly Leu Gln Glu Pro Arg Arg Val Glu Glu Leu Gln Asn Arg Ile
530                 535                 540

Ala Ser Cys Leu Lys Glu His Val Ala Ala Val Ala Gly Glu Pro Gln
545                 550                 555                 560

Pro Ala Ser Cys Leu Ser Arg Leu Leu Gly Lys Leu Pro Glu Leu Arg
            565                 570                 575

Thr Leu Cys Thr Gln Gly Leu Gln Arg Ile Phe Tyr Leu Lys Leu Glu
            580                 585                 590

Asp Leu Val Pro Pro Pro Ile Ile Asp Lys Ile Phe Met Asp Thr
            595                 600                 605

Leu Pro Phe
    610

<210> SEQ ID NO 2
<211> LENGTH: 598
<212> TYPE: PRT
```

<213> ORGANISM: Homo sapiens

<400> SEQUENCE: 2

Met Pro Cys Ile Gln Ala Gln Tyr Gly Thr Pro Ala Pro Ser Pro Gly
1               5                   10                  15

Pro Arg Asp His Leu Ala Ser Asp Pro Leu Thr Pro Glu Phe Ile Lys
            20                  25                  30

Pro Thr Met Asp Leu Ala Ser Pro Glu Ala Ala Pro Ala Ala Pro Thr
        35                  40                  45

Ala Leu Pro Ser Phe Ser Thr Phe Met Asp Gly Tyr Thr Gly Glu Phe
    50                  55                  60

Asp Thr Phe Leu Tyr Gln Leu Pro Gly Thr Val Gln Pro Cys Ser Ser
65                  70                  75                  80

Ala Ser Ser Ser Ala Ser Ser Thr Ser Ser Ser Ala Thr Ser Pro
                85                  90                  95

Ala Ser Ala Ser Phe Lys Phe Glu Asp Phe Gln Val Tyr Gly Cys Tyr
                100                 105                 110

Pro Gly Pro Leu Ser Gly Pro Val Asp Glu Ala Leu Ser Ser Ser Gly
            115                 120                 125

Ser Asp Tyr Tyr Gly Ser Pro Cys Ser Ala Pro Ser Pro Ser Thr Pro
    130                 135                 140

Ser Phe Gln Pro Pro Gln Leu Ser Pro Trp Asp Gly Ser Phe Gly His
145                 150                 155                 160

Phe Ser Pro Ser Gln Thr Tyr Glu Gly Leu Arg Ala Trp Thr Glu Gln
                165                 170                 175

Leu Pro Lys Ala Ser Gly Pro Pro Gln Pro Pro Ala Phe Phe Ser Phe
            180                 185                 190

Ser Pro Pro Thr Gly Pro Ser Pro Ser Leu Ala Gln Ser Pro Leu Lys
            195                 200                 205

Leu Phe Pro Ser Gln Ala Thr His Gln Leu Gly Glu Gly Glu Ser Tyr
    210                 215                 220

Ser Met Pro Thr Ala Phe Pro Gly Leu Ala Pro Thr Ser Pro His Leu
225                 230                 235                 240

Glu Gly Ser Gly Ile Leu Asp Thr Pro Val Thr Ser Thr Lys Ala Arg
                245                 250                 255

Ser Gly Ala Pro Gly Gly Ser Glu Gly Arg Cys Ala Val Cys Gly Asp
            260                 265                 270

Asn Ala Ser Cys Gln His Tyr Gly Val Arg Thr Cys Glu Gly Cys Lys
            275                 280                 285

Gly Phe Phe Lys Arg Thr Val Gln Lys Asn Ala Lys Tyr Ile Cys Leu
290                 295                 300

Ala Asn Lys Asp Cys Pro Val Asp Lys Arg Arg Arg Asn Arg Cys Gln
305                 310                 315                 320

Phe Cys Arg Phe Gln Lys Cys Leu Ala Val Gly Met Val Lys Glu Val
                325                 330                 335

Val Arg Thr Asp Ser Leu Lys Gly Arg Arg Gly Arg Leu Pro Ser Lys
            340                 345                 350

Pro Lys Gln Pro Pro Asp Ala Ser Pro Ala Asn Leu Leu Thr Ser Leu
            355                 360                 365

Val Arg Ala His Leu Asp Ser Gly Pro Ser Thr Ala Lys Leu Asp Tyr
    370                 375                 380

Ser Lys Phe Gln Glu Leu Val Leu Pro His Phe Gly Lys Glu Asp Ala
385                 390                 395                 400

-continued

```
Gly Asp Val Gln Gln Phe Tyr Asp Leu Leu Ser Gly Ser Leu Glu Val
                405                 410                 415

Ile Arg Lys Trp Ala Glu Lys Ile Pro Gly Phe Ala Glu Leu Ser Pro
            420                 425                 430

Ala Asp Gln Asp Leu Leu Leu Glu Ser Ala Phe Leu Glu Leu Phe Ile
            435                 440                 445

Leu Arg Leu Ala Tyr Arg Ser Lys Pro Gly Glu Gly Lys Leu Ile Phe
    450                 455                 460

Cys Ser Gly Leu Val Leu His Arg Leu Gln Cys Ala Arg Gly Phe Gly
465                 470                 475                 480

Asp Trp Ile Asp Ser Ile Leu Ala Phe Ser Arg Ser Leu His Ser Leu
            485                 490                 495

Leu Val Asp Val Pro Ala Phe Ala Cys Leu Ser Ala Leu Val Leu Ile
            500                 505                 510

Thr Asp Arg His Gly Leu Gln Glu Pro Arg Arg Val Glu Glu Leu Gln
            515                 520                 525

Asn Arg Ile Ala Ser Cys Leu Lys Glu His Val Ala Ala Val Ala Gly
    530                 535                 540

Glu Pro Gln Pro Ala Ser Cys Leu Ser Arg Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Pro Ile Ile Asp Lys Ile Phe
            580                 585                 590

Met Asp Thr Leu Pro Phe
            595
```